United States Patent
Brown (12)

(10) Patent No.: US 6,180,391 B1
(45) Date of Patent: Jan. 30, 2001

(54) HIGHLY EFFICIENT CONTROLLED EXPRESSION OF EXOGENOUS GENES IN E. COLI

(75) Inventor: William C. Brown, Woodland Hills, CA (US)

(73) Assignee: Amgen Inc., Thousands Oaks, CA (US)

(*) Notice: Under 35 U.S.C. 154(b), the term of this patent shall be extended for 0 days.

(21) Appl. No.: 09/237,712

(22) Filed: Jan. 26, 1999

Related U.S. Application Data

(60) Provisional application No. 60/072,794, filed on Jan. 28, 1998.

(51) Int. Cl.⁷ .......................... C07H 21/04; C12N 15/63; C12N 1/21
(52) U.S. Cl. ................................. 435/252.3; 435/320.1; 536/23.1; 536/24.1
(58) Field of Search .................................. 435/69.1, 69.2, 435/91.4, 471, 375, 252.33, 320.1; 536/23.1, 23.72, 24.1, 24.5

(56) References Cited

U.S. PATENT DOCUMENTS

| | | | |
|---|---|---|---|
| 4,503,142 | 3/1985 | Berman et al. | 435/6 |
| 4,578,355 | 3/1986 | Rosenberg et al. | 435/320.1 |
| 4,767,708 | 8/1988 | Minkley et al. | 435/194 |

FOREIGN PATENT DOCUMENTS

WO 97/04110    2/1997    (WO).

OTHER PUBLICATIONS

Studier et al., "Use of Bacteriophage T7 RNA Polymerase to Direct Selective High–Level Expression of Cloned Genes", *Journal of Molecular Biology* 189 pp. 113–130 (1996).

Dietrich et al., "Expression of Mammalian tyrosine aminotransferase in Saccharomyces Cerevisiae and *Escherichia coli*" *Eur. Journal of Biochemistry*, 201 pp. 399–407 (1991).

Lathrop et al., "Expression of a Group II Phospholipase A2 from the Venom of Agkistrodon piscivorus piscivorus in *Escherichia coli*: Recovery and Renaturation from Bacterial Inclusion Bodies" *Protein Expression and Purification*, 3 pp. 512–517 (1992).

Aukhil et al., "Cell–and Heparin–binding Domains of the Hexabrachion Arm identified by Tenascin Expression Protiens" *The Journal of Biological Chemistry*, 268 (4) pp. 2542–2553 (1993).

Studier, W., "Use of Bacteriophage T7 Lysozyme to Improve an Inducible T7 Expression System" *Journal of Molecular Biology*, 219 pp. 37–44 (1991).

Dubendorff, et al., "Controlling Basal Expression in an Inducible T7 Expression System by Blocking the Target T7 Promoter with Iac Repressor" *Journal of Molecular Biology*, 219 pp. 45–59 (1991).

Brown, et al., "A new cloning vector and expression strategy for genes encoding proteins toxic to *Escherichia coli*" Gene, 127 pp. 99–103 (1993).

Van Duin, J., "Single–Stranded RNA Bacteriophages" Dept. of Biochemistry, University of Leiden, Leiden, The Netherlands, Chapter 4, 117–167, Plenum Press, New York (1988).

Fiers et al., "Complete nucleotide sequence of bacteriophage MS2 RNA: primary and secondary structure of the replicase gene" *Nature*, 260 pp. 500–507 (1976).

Peabody, et al., "Control of translation repression by protein—protein interactions" *Nucleic Acids Research*, 20 (7) pp. 1649–1655 (1992).

Peabody, D., "Translational Repression by Bacteriophage MS2 Coat Protein Expressed from a Plasmid" *Journal of Biological Chemistry*, 265 (10) pp. 5684–5689 (1990).

Brody et al., "Old phage, new insights: Two recently recognized mechanisms of transcriptional regulation in bacteriophage T4 development" *FEMS Microbiology Letters*, 128 pp. 1–8 (1995).

Ouhammouch et al., "Bacteriophage T4 MotA and AsiA proteins suffice to direct *Escherichia coli* RNA polymerase to initiate transcription at T4 middle promoters" *Proc. National Academy of Science. USA*, 92: pp. 1451–1455 (1995).

Daniels, et al., "Promoter Mutations Affecting Divergent Transcription in the Tn10 Tetracycline Resistance Determinant" *Journal of Molecular Biology*, 184(4) pp. 599–610, (1985).

Martin, et al., "Total synthesis and expression in *Escherichia coli* of a gene encoding human tropoelastin" Gene, 154 (2) pp. 159–166 (1995).

Peabody, "The RNA binding site of bacteriophage MS2 coat protein " *EMBO Journal*, 12 (2), pp. 595–600 (1993).

Studier, et al., "Use of 7 RNA Polymerase to Direct Expression fo Cloned Genes" *Methods of Enzymology*, 185 pp. 60–89, (1990).

Stripecke et al., "Bacteriophage and spliceosomal protiens function as position–dependent cis/trans repressors of mRNA translation in vitro" *Nucleic Acids Research*, 20(21) pp. 5555–5564 (1992).

Lim et al., "Altering the RNA Binding Specificity of a Translational Repressor" *Journal of Biological Chemistry*, 269 pp. 9006–9010 (1994).

Skerra, A., "Use of the tetracycline promoter for the tightly regulated production of a murine antibody fragment in *Escherichia coli* " GENE, 151 (1) pp. 131–135 (1994).

(List continued on next page.)

*Primary Examiner*—Robert A. Schwartzman
(74) *Attorney, Agent, or Firm*—Craig A. Crandall; Ron K. Levy; Steven M. Odre

(57) ABSTRACT

The invention relates generally to recombinant methods and materials for effecting the microbial production of useful polypeptides. More particularly, the invention relates to expression vector systems which utilize a translational repressor system, and transcriptional control proteins to provide a highly efficient, tightly regulated, staged inducible promoter system capable of expressing exogenous genes, including toxic genes, in *E. coli*.

22 Claims, 39 Drawing Sheets

OTHER PUBLICATIONS

Harley et al., "Transcription initiation at the tet promoter and effect of mutants" *Nucleic Acids Research*, 16 (15) pp. 7269–7285 (1988).

Dunn et al., "Nucleotide Sequence from the Genetic Left End of Bacteriophage T7 DNA to the Beginning of Gene 4" *Journal of Molecular Biology*, 148 (4) pp. 303–330 (1981).

Stripecke, et al., "Proteins Binding to 5 ' Untranslated Region Sites: a General Mechanism for Translational Regulation of mRNAs in Human and Yeast Cells" *Molecular and Cellular Biology*, 14 (9) pp. 5898–5909 (1994).

```
ATGGCTTCTA ACCTTCACTC AGTTCGTACT GGTTGACAAC GGCGGTACCG
GCGATGTAAC TGTTGCACCG TCCAACTTCG CAAATGGCGT TGCTGAATGG
ATTTCTTCCA ACTCTCGCAG CCAGGCTTAC AAAGTAACTT GCAGCGTTCG
CCAGTCCTCT GCACAAAACC GAAAATACAC CATCAAGGTA GAAGTCCCGA
AAGTTGCGAC CCAGACTGTA GGCGGTGTCG AACTGCCGGT TGCTGCATGG
CGCAGCTACC TGAACATGGA ACTGACTATC CCGATTTTCG CAACCAACTC
TGACTGTGAA CTGATCGTAA AAGCTATGCA GGGTCTGCTA AAAGATGGCA
ATCCAATTCC GTCCGCAATC GCTGCAAACT CTGGTATCTA CTAATAG
```

FIG. 1

```
TCTAGAAAAC ATGAGGATTA CCCATGGCTA TGTCTAATCT CACATATAAC
AACGTTTTCG ACCACGCTTA CGAAATGCTG AAAGAAAACA TCCGTTATGA
TGACATCCGT GACACTGATG ACCTGCACGA TGCTATTCAC ATGGCTGCCG
ATAATGCAGT TCCGCACTAC TACGCTGACA TCTTTAGCGT AATGGCAAGT
GAGGGCATTG ACCTTGAGTT CGAAGACTCT GGTCTGATGC CTGACACCAA
GGACGTAATC CGCATCCTGC AAGCGCGTAT CTATGAGCAA TTAACGATTG
ACCTCTGGGA AGACGCAGAA GACTTGCTCA ATGAATACTT GGAGGAAGTC
GAGGAGTACG AGGAGGATGA AGAGTAAAAA CATGAGGATT ACCCATGTCT
AATACCAACG TGCAATACGG TCTGACCGCT CAAACTGTAC TTTTCTATAG
CGACATGGTG CGCTGTGGCT TTAACTGGTC ACTCGCAATG CACAGCTCA
AAGAACTGTA CGAAAACAAC AAGGCAATAG CTTTAGAACC TGCTGAGTGA
TAGACTCAAA CATGAGGATT ACCCATGTAT ATGCTTACTA TCGGTCTACT
CACCGCTCTA GGTCTGGCTG TAGGTGCATC CTTTGGGAAG CTTTAGGTG
TAGCTGTAGG TTCCTACTTT ACCGCTTGCA TCATCATAGG AATCATCAAA
GGGGCACTAC GCAAATGATG AAAACATGAG GATTACCCAT GCGGCATTAC
GTTATGCCAA TCCACACGTC AACGGGGCA ACCGTATGTA CACCTGATGG
GTTCGCAATG AAACAACGAA TCGAACGCCT TGAGCGTGAA CTCCGCATTA
ACCGCAAGAT TAACAAGATA GGTTCCGGCT ATGACAGAAC GCACTGATGG
```

FIG.17 A

```
CTTAAAGAAA GGTTATATGC CCAATGGCAC ACTATACGCT GCAAATCGGC
GAATAGTGAG AACTTGGCGA GAGAACAACC TCGAACGCCG CAAGGAACAA
GAGAGGGCGG TGTGGCATAG ACGAAAGGAA AAGGTTAAAG CCAAGAAACT
CGCCGCACTT GAACAGGCAC TAGCCAACAC ACTGAACGCT ATCTCATAAA
AACATGAGGA TTACCCATGA ACATTACCGA CATATCAAAC GCTATCGACG
CAATCAAAGC ACTGCCAATC TGTGAACTTG ACAAGCGTCA AGGTATGCTT
ATCGACTTAC TGGTCGAGAT GGTCAACAGC GAGACGTGTG ATGGCGAGCT
AACCGAACTA ATCAGGCAC TTGAGCATCA AGATTGGTGG ACTACCTTGA
AGTGTCTCAC GGCTGACGCA GGGTTCAAGA TGCTCGGTGA TGGTCACTTC
TCGGCTGCTT ATAGTCACCC GCTGCTACCT AACAGAGTGA TTAAGGTGGG
CTTTAAGAAA GAGGATTCAG GCGCAGCCTA TACCGCATTC TGCCGCATGT
ATCAGGGTCG TCCTGGTATC CCTAACGTCT ACGATGTACA GCGCCACGCT
GGATGCTATA CGGTGGTACT TGACGCACTT AAGGATTGCG AGCGTTTCAA
CAATGATGCT CATTATAAAT ACGCTGAGAT TGCAAGCGAC ATCATTGATT
GCAATTCGGA TGAGCATGAT GAGTTAACTG GATGGGATGG TGAGTTTGTT
GAAACTTGTA AACTAATCCG CAAGTTCTTT GAGGGCATCG CCTCATTCGA
CATGCATAGC GGGAACATCA TGTTCTCAAA TGGAGACGTA CCATACATCA
CCGACCCGGT ATCATTCTCG CAGAAGAAAG ACGGTGGCGC ATTCAGCATC
GACCCTGAGG AACTCATCAA GGAAGTCGAG AAGTCGCAT GATAGCTCGA
G
```

FIG. 17 B

GGCAAAAAGC AGTCAGAAGA AACTAAAGCA AAACGAAAAG AAGCTTTGCT
TAATAATCCA TATGGTTATA ATAGAAATAA ACCATCA

FIG.22

TGATAGAGTC AATGAGTTAA AACACAGTGA TGTTTTGCGT AAAGAGATGC
TTTCTATTCA ACATGATATT TTAAATAAAA CCCGTGC

FIG.23

SEQUENCE LISTING

<160> NUMBER OF SEQ ID NOS: 98

<210> SEQ ID NO 1
<211> LENGTH: 397
<212> TYPE: DNA
<213> ORGANISM: MS2 bacteriophage

<400> SEQUENCE: 1

```
atggcttcta accttcactc agttcgtact ggttgacaac ggcggtaccg gcgatgtaac      60
tgttgcaccg tccaacttcg caaatggcgt tgctgaatgg atttcttcca actctcgcag     120
ccaggcttac aaagtaactt gcagcgttcg ccagtcctct gcacaaaacc gaaaatacac     180
catcaaggta gaagtcccga aagttgcgac ccagactgta ggcggtgtcg aactgccggt     240
tgctgcatgg cgcagctacc tgaacatgga actgactatc ccgattttcg caaccaactc     300
tgactgtgaa ctgatcgtaa aagctatgca gggtctgcta aaagatggca atccaattcc     360
gtccgcaatc gctgcaaact ctggtatcta ctaatag                              397
```

<210> SEQ ID NO 2
<211> LENGTH: 1851
<212> TYPE: DNA
<213> ORGANISM: T7 bacteriophage

<400> SEQUENCE: 2

```
tctagaaaac atgaggatta cccatggcta tgtctaatct cacatataac aacgttttcg      60
accacgctta cgaaatgctg aaagaaaaca tccgttatga tgacatccgt gacactgatg     120
acctgcacga tgctattcac atggctgccg ataatgcagt tccgcactac tacgctgaca     180
tctttagcgt aatggcaagt gagggcattg accttgagtt cgaagactct ggtctgatgc     240
ctgacaccaa ggacgtaatc cgcatcctgc aagcgcgtat ctatgagcaa ttaacgattg     300
acctctggga agacgcagaa gacttgctca atgaatactt ggaggaagtc gaggagtacg     360
aggaggatga agagtaaaaa catgaggatt acccatgtct aataccaacg tgcaatacgg     420
tctgaccgct caaactgtac ttttctatag cgacatggtg cgctgtggct ttaactggtc     480
actcgcaatg gcacagctca aagaactgta cgaaaacaac aaggcaatag ctttagaacc     540
tgctgagtga tagactcaaa catgaggatt acccatgtat atgcttacta tcggtctact     600
```

```
caccgctcta ggtctggctg taggtgcatc ctttgggaag gctttaggtg tagctgtagg      660
ttcctacttt accgcttgca tcatcatagg aatcatcaaa ggggcactac gcaaatgatg      720
aaaacatgag gattacccat gcggcattac gttatgccaa tccacacgtc aacggggca      780 accgtatgta cacctgatgg gttcgcaatg aaacaacgaa tcgaacgcct tgagcgtgaa      840
ctccgcatta accgcaagat taacaagata ggttccggct atgacagaac gcactgatgg      900
cttaaagaaa ggttatatgc ccaatggcac actatacgct gcaaatcggc gaatagtgag      960
aacttggcga gagaacaacc tcgaacgccg caaggaacaa gagagggcgg tgtggcatag     1020
acgaaaggaa aaggttaaag ccaagaaact cgccgcactt gaacaggcac tagccaacac     1080
actgaacgct atctcataaa aacatgagga ttacccatga acattaccga catatcaaac     1140
gctatcgacg caatcaaagc actgccaatc tgtgaacttg acaagcgtca aggtatgctt     1200
atcgacttac tggtcgagat ggtcaacagc gagacgtgtg atggcgagct aaccgaacta     1260
aatcaggcac ttgagcatca agattggtgg actaccttga agtgtctcac ggctgacgca     1320
gggttcaaga tgctcggtga tggtcacttc tcggctgctt atagtcaccc gctgctacct     1380
aacagagtga ttaaggtggg ctttaagaaa gaggattcag gcgcagccta taccgcattc     1440
tgccgcatgt atcagggtcg tcctggtatc cctaacgtct acgatgtaca cgccacgct     1500 ggatgctata cggtggtact tgacgcactt aaggattgcg agcgtttcaa caatgatgct     1560
cattataaat acgctgagat tgcaagcgac atcattgatt gcaattcgga tgagcatgat     1620
gagttaactg gatgggatgg tgagtttgtt gaaacttgta aactaatccg caagttcttt     1680
gagggcatcg cctcattcga catgcatagc gggaacatca tgttctcaaa tggagacgta     1740
ccatacatca ccgacccggt atcattctcg cagaagaaag acgtggcgc attcagcatc     1800 gaccctgagg aactcatcaa ggaagtcgag gaagtcgcat gatagctcga g             1851

<210> SEQ ID NO 3
<211> LENGTH: 87
<212> TYPE: DNA
<213> ORGANISM: T4 bacteriophage

<400> SEQUENCE: 3
ggcaaaaagc agtcagaaga aactaaagca aaacgaaaag aagctttgct taataatcca      60
tatggttata atagaaataa accatca                                          87

<210> SEQ ID NO 4
<211> LENGTH: 87
<212> TYPE: DNA
<213> ORGANISM: T4 bacteriophage

<400> SEQUENCE: 4
tgatagagtc aatgagttaa aacacagtga tgttttgcgt aaagagatgc tttctattca      60
acatgatatt ttaaataaaa cccgtgc                                          87

<210> SEQ ID NO 5
<211> LENGTH: 37
<212> TYPE: DNA
<213> ORGANISM: oligonucleotide

<400> SEQUENCE: 5
tatggcttct aacttcactc agttcgtact ggttgac                               37

<210> SEQ ID NO 6
```

```
<211> LENGTH: 40
<212> TYPE: DNA
<213> ORGANISM: oligonucleotide

<400> SEQUENCE: 6
gccttgtcaa ccagtacgaa ctgagtgaag ttagaagcca                              40

<210> SEQ ID NO 7
<211> LENGTH: 42
<212> TYPE: DNA
<213> ORGANISM: oligonucleotide

<400> SEQUENCE: 7
aacggcggta ccggcgatgt aactgttgca ccgtccaact tc                           42

<210> SEQ ID NO 8
<211> LENGTH: 42
<212> TYPE: DNA
<213> ORGANISM: oligonucleotide

<400> SEQUENCE: 8
atttgcgaag ttggacggtg caacagttac atcgccggta cc                           42

<210> SEQ ID NO 9
<211> LENGTH: 36
<212> TYPE: DNA
<213> ORGANISM: oligonucleotide

<400> SEQUENCE: 9
gcaaatggcg ttgctgaatg gatttcttcc aactct                                  36

<210> SEQ ID NO 10
<211> LENGTH: 36
<212> TYPE: DNA
<213> ORGANISM: oligonucleotide

<400> SEQUENCE: 10
gctgcgagag ttggaagaaa tccattcagc aacgcc                                  36

<210> SEQ ID NO 11
<211> LENGTH: 42
<212> TYPE: DNA
<213> ORGANISM: oligonucleotide

<400> SEQUENCE: 11
cgcagccagg cttacaaagt aacttgcagc gttcgccagt cc                           42

<210> SEQ ID NO 12
<211> LENGTH: 42
<212> TYPE: DNA
<213> ORGANISM: oligonucleotide

<400> SEQUENCE: 12
tgcagaggac tggcgaacgc tgcaagttac tttgtaagcc tg                           42

<210> SEQ ID NO 13
<211> LENGTH: 36
<212> TYPE: DNA
<213> ORGANISM: oligonucleotide

<400> SEQUENCE: 13
tctgcacaaa accgaaaata caccatcaag gtagaa                                  36
```

-continued

<210> SEQ ID NO 14
<211> LENGTH: 36
<212> TYPE: DNA
<213> ORGANISM: oligonucleotide

<400> SEQUENCE: 14
cgggacttct accttgatgg tgtattttcg gttttg                    36

<210> SEQ ID NO 15
<211> LENGTH: 42
<212> TYPE: DNA
<213> ORGANISM: oligonucleotide

<400> SEQUENCE: 15
gtcccgaaag ttgcgaccca gactgtaggc ggtgtcgaac tg             42

<210> SEQ ID NO 16
<211> LENGTH: 42
<212> TYPE: DNA
<213> ORGANISM: oligonucleotide

<400> SEQUENCE: 16
aaccggcagt tcgacaccgc ctaccgtctg ggtcgcaact tt             42

<210> SEQ ID NO 17
<211> LENGTH: 36
<212> TYPE: DNA
<213> ORGANISM: oligonucleotide

<400> SEQUENCE: 17
ccggttgctg catggcgcag ctacctgaac atggaa                    36

<210> SEQ ID NO 18
<211> LENGTH: 36
<212> TYPE: DNA
<213> ORGANISM: oligonucleotide

<400> SEQUENCE: 18
cgtcagttcc atgttcaggt agctgcgcca tgcagc                    36

<210> SEQ ID NO 19
<211> LENGTH: 42
<212> TYPE: DNA
<213> ORGANISM: oligonucleotide

<400> SEQUENCE: 19
ctgactatcc cgattttcgc aaccaactct gactgtgaac tg             42

<210> SEQ ID NO 20
<211> LENGTH: 42
<212> TYPE: DNA
<213> ORGANISM: oligonucleotide

<400> SEQUENCE: 20
tacgatcagt tcacagtcag agttggttgc gaaaatcggg at             42

<210> SEQ ID NO 21
<211> LENGTH: 33
<212> TYPE: DNA
<213> ORGANISM: oligonucleotide

<400> SEQUENCE: 21
atcgtaaaag ctatgcaggg tctgctaaaa gat                       33

<210> SEQ ID NO 22
<211> LENGTH: 33
<212> TYPE: DNA
<213> ORGANISM: oligonucleotide

<400> SEQUENCE: 22
attgccatct tttagcagac cctgcatagc ttt                           33

<210> SEQ ID NO 23
<211> LENGTH: 51
<212> TYPE: DNA
<213> ORGANISM: oligonucleotide

<400> SEQUENCE: 23
ggcaatccaa ttccgtccgc aatcgctgca aactctggta tctactaata g        51

<210> SEQ ID NO 24
<211> LENGTH: 49
<212> TYPE: DNA
<213> ORGANISM: oligonucleotide

<400> SEQUENCE: 24
gatcctatta gtagatacca gagtttgcag cgattgcgga cggaattgg           49

<210> SEQ ID NO 25
<211> LENGTH: 22
<212> TYPE: DNA
<213> ORGANISM: oligonucleotide

<400> SEQUENCE: 25
cgcaaatggc attgctgaat gg                                       22

<210> SEQ ID NO 26
<211> LENGTH: 22
<212> TYPE: DNA
<213> ORGANISM: oligonucleotide

<400> SEQUENCE: 26
ccattcagca atgccatttg cg                                       22

<210> SEQ ID NO 27
<211> LENGTH: 24
<212> TYPE: DNA
<213> ORGANISM: oligonucleotide

<400> SEQUENCE: 27
ccaactctga ccgtgaactg atcg                                     24

<210> SEQ ID NO 28
<211> LENGTH: 24
<212> TYPE: DNA
<213> ORGANISM: oligonucleotide

<400> SEQUENCE: 28
cgatcagttc acggtcagag ttgg                                     24

<210> SEQ ID NO 29
<211> LENGTH: 42
<212> TYPE: DNA
<213> ORGANISM: oligonucleotide

<400> SEQUENCE: 29
agctggtgag ctcgatcatt gggcatacgc atgctgcagc gc                 42

<210> SEQ ID NO 30
<211> LENGTH: 43
<212> TYPE: DNA
<213> ORGANISM: oligonucleotide

<400> SEQUENCE: 30
tctaggcgct gcagcatgcg tatgcccaat gatcgagctc acc          43

<210> SEQ ID NO 31
<211> LENGTH: 33
<212> TYPE: DNA
<213> ORGANISM: oligonucleotide

<400> SEQUENCE: 31
ggccaatcgc gaattgacgt cacgttcaga att                     33

<210> SEQ ID NO 32
<211> LENGTH: 33
<212> TYPE: DNA
<213> ORGANISM: oligonucleotide

<400> SEQUENCE: 32
ggccaattct gaacgtgacg tcaattcgcg att                     33

<210> SEQ ID NO 33
<211> LENGTH: 35
<212> TYPE: DNA
<213> ORGANISM: oligonucleotide

<400> SEQUENCE: 33
atgcatcgag ctcgattagg acatggggcc tcgct                   35

<210> SEQ ID NO 34
<211> LENGTH: 69
<212> TYPE: DNA
<213> ORGANISM: oligonucleotide

<400> SEQUENCE: 34
gcccgcgcga gctcgttgta attctcatgt ttgacagctt atcatcgata agctttaatg   60
cggtagttt                                                           69

<210> SEQ ID NO 35
<211> LENGTH: 66
<212> TYPE: DNA
<213> ORGANISM: oligonucleotide

<400> SEQUENCE: 35
gggaattcca tatgcggtgc ctgactgcgt tagcaattta actgtgataa actaccgcat   60
taaagc                                                              66

<210> SEQ ID NO 36
<211> LENGTH: 42
<212> TYPE: DNA
<213> ORGANISM: oligonucleotide

<400> SEQUENCE: 36
gattcccccg ggcaaataaa acgaaaggct cagtcgaaag ac            42

<210> SEQ ID NO 37
<211> LENGTH: 44
<212> TYPE: DNA

<213> ORGANISM: oligonucleotide

<400> SEQUENCE: 37
ctgatcgcga cgtcttgtag aaacgcaaaa aggccatccg tcag            44

<210> SEQ ID NO 38
<211> LENGTH: 63
<212> TYPE: DNA
<213> ORGANISM: oligonucleotide

<400> SEQUENCE: 38
gctctagaaa catgaggatt acccatgaac acgattaaca tcgctaagaa cgacttctct   60
gac                                                        63

<210> SEQ ID NO 39
<211> LENGTH: 36
<212> TYPE: DNA
<213> ORGANISM: oligonucleotide

<400> SEQUENCE: 39
cgggatccgt cattacgcga acgcgaagtc cgactc                    36

<210> SEQ ID NO 40
<211> LENGTH: 71
<212> TYPE: DNA
<213> ORGANISM: oligonucleotide

<400> SEQUENCE: 40
gcgcgctcta gaaaacatga ggattaccca tgaataccat caatatcgct aagaacgact   60
tctctgacat c                                               71

<210> SEQ ID NO 41
<211> LENGTH: 33
<212> TYPE: DNA
<213> ORGANISM: oligonucleotide

<400> SEQUENCE: 41
ggcccagtgc atgcctacgt gggtcctagt cgc                       33

<210> SEQ ID NO 42
<211> LENGTH: 33
<212> TYPE: DNA
<213> ORGANISM: oligonucleotide

<400> SEQUENCE: 42
gatcgcgact aggacccacg taggcatgca ctg                       33

<210> SEQ ID NO 43
<211> LENGTH: 18
<212> TYPE: DNA
<213> ORGANISM: oligonucleotide

<400> SEQUENCE: 43
ctgaatacgc tgaggcta                                        18

<210> SEQ ID NO 44
<211> LENGTH: 18
<212> TYPE: DNA
<213> ORGANISM: oligonucleotide

<400> SEQUENCE: 44
tcagccagta gtaacctt                                        18

<210> SEQ ID NO 45
<211> LENGTH: 48
<212> TYPE: DNA
<213> ORGANISM: oligonucleotide

<400> SEQUENCE: 45
gcgcgcgaat tctttcgatc tactaccaac gtgcaatacg gtctgacc          48

<210> SEQ ID NO 46
<211> LENGTH: 48
<212> TYPE: DNA
<213> ORGANISM: oligonucleotide

<400> SEQUENCE: 46
gcgcgcgaat tctttcgaat gaagcactac gttatgccaa tccacacg          48

<210> SEQ ID NO 47
<211> LENGTH: 61
<212> TYPE: DNA
<213> ORGANISM: oligonucleotide

<400> SEQUENCE: 47
ctagagcaaa catgaggatt acccatgaaa catcaccatc accatcacca taccggtggc    60
g                                                                    61

<210> SEQ ID NO 48
<211> LENGTH: 61
<212> TYPE: DNA
<213> ORGANISM: oligonucleotide

<400> SEQUENCE: 48
aattcgccac cggtatggtg atggtgatgg tgatgtttca tgggtaatcc tcatgtttgc    60
t                                                                    61

<210> SEQ ID NO 49
<211> LENGTH: 62
<212> TYPE: DNA
<213> ORGANISM: oligonucleotide

<400> SEQUENCE: 49
gcgcgctcta gaaaacatga ggattaccca tgtctactac caacgtgcaa tacggtctga    60
cc                                                                   62

<210> SEQ ID NO 50
<211> LENGTH: 36
<212> TYPE: DNA
<213> ORGANISM: oligonucleotide

<400> SEQUENCE: 50
gcgcgcggat ccgagtctat cactcagcag attcta                      36

<210> SEQ ID NO 51
<211> LENGTH: 42
<212> TYPE: DNA
<213> ORGANISM: oligonucleotide

<400> SEQUENCE: 51
gcgcgcggat ccctattatg agatagcgtt cagtgtgttg gc                42

<210> SEQ ID NO 52

```
<211> LENGTH: 69
<212> TYPE: DNA
<213> ORGANISM: oligonucleotide

<400> SEQUENCE: 52
gcgcgcctca gaaaacatga ggattaccca tgaacattac cgacatcatg aacgctatcg    60
acgcaatca                                                            69

<210> SEQ ID NO 53
<211> LENGTH: 36
<212> TYPE: DNA
<213> ORGANISM: oligonucleotide

<400> SEQUENCE: 53
gcgcgcggat ccctatcagc ccattaacat tgcgtc                              36

<210> SEQ ID NO 54
<211> LENGTH: 36
<212> TYPE: DNA
<213> ORGANISM: oligonucleotide

<400> SEQUENCE: 54
gcgcgcggat ccctatcatg cgacttcctc gacttc                              36

<210> SEQ ID NO 55
<211> LENGTH: 68
<212> TYPE: DNA
<213> ORGANISM: oligonucleotide

<400> SEQUENCE: 55
gcgcgctcta gaaaacatga ggattaccca tggctatgtc taatctcaca tataacaacg    60
ttttcgac                                                             68

<210> SEQ ID NO 56
<211> LENGTH: 60
<212> TYPE: DNA
<213> ORGANISM: oligonucleotide

<400> SEQUENCE: 56
cacgttggta gtagacatgg gtaatcctca tgttttact cttcatcctc ctcgtactcc     60

<210> SEQ ID NO 57
<211> LENGTH: 58
<212> TYPE: DNA
<213> ORGANISM: oligonucleotide

<400> SEQUENCE: 57
gtcggtaatg ttcatgggta atcctcatgt ttttatgaga tagcgttcag tgtgttgg      58

<210> SEQ ID NO 58
<211> LENGTH: 56
<212> TYPE: DNA
<213> ORGANISM: oligonucleotide

<400> SEQUENCE: 58
agcatataca tgggtaatcc tcatgtttga gtctatcact cagcagattc taaagc        56

<210> SEQ ID NO 59
<211> LENGTH: 45
<212> TYPE: DNA
<213> ORGANISM: oligonucleotide

<400> SEQUENCE: 59
```
ctgctgagtg atagactcaa acatgaggat tacccatgta tatgc    45

<210> SEQ ID NO 60
<211> LENGTH: 63
<212> TYPE: DNA
<213> ORGANISM: oligonucleotide

<400> SEQUENCE: 60
cataacgtaa tgccgcatgg gtaatcctca tgttttcatc atttgcgtag tgcccctttg    60
atg    63

<210> SEQ ID NO 61
<211> LENGTH: 63
<212> TYPE: DNA
<213> ORGANISM: oligonucleotide

<400> SEQUENCE: 61
catcaaaggg gcactacgca aatgatgaaa acatgaggat tacccatgcg gcattacgtt    60
atg    63

<210> SEQ ID NO 62
<211> LENGTH: 48
<212> TYPE: DNA
<213> ORGANISM: oligonucleotide

<400> SEQUENCE: 62
gaacgctatc tcataacgaa acatgaggat tacccatgaa cattaccg    48

<210> SEQ ID NO 63
<211> LENGTH: 25
<212> TYPE: DNA
<213> ORGANISM: oligonucleotide

<400> SEQUENCE: 63
gcgcggatcc ctatcatgcg acttc    25

<210> SEQ ID NO 64
<211> LENGTH: 66
<212> TYPE: DNA
<213> ORGANISM: oligonucleotide

<400> SEQUENCE: 64
gcgcgcgacg tcggcaaaaa gcagtcagaa gaaactaaag cagcaaaacg aaaagaagct    60
ttgctt    66

<210> SEQ ID NO 65
<211> LENGTH: 63
<212> TYPE: DNA
<213> ORGANISM: oligonucleotide

<400> SEQUENCE: 65
gcgcgcatcg attgatggtt tatttctatt ataaccatat ggattattaa gcaaagcttc    60
ttt    63

<210> SEQ ID NO 66
<211> LENGTH: 60
<212> TYPE: DNA
<213> ORGANISM: oligonucleotide

<400> SEQUENCE: 66

```
gcgcgcgacg tctgatagag tcaatgagtt aaaacacagt gatgttttgc gtaaagagat    60
```

<210> SEQ ID NO 67
<211> LENGTH: 63
<212> TYPE: DNA
<213> ORGANISM: oligonucleotide

<400> SEQUENCE: 67

```
gcgcgcatcg atgcacgggt tttatttaaa atatcatgtt gaatagaaag catctcttta    60
cgc                                                                 63
```

<210> SEQ ID NO 68
<211> LENGTH: 63
<212> TYPE: DNA
<213> ORGANISM: oligonucleotide

<400> SEQUENCE: 68

```
gcgcgcgacg tcggcaaaaa gcagtcagaa gaaactaaag caaaacgaaa agaagctttg    60
ctt                                                                 63
```

<210> SEQ ID NO 69
<211> LENGTH: 63
<212> TYPE: DNA
<213> ORGANISM: oligonucleotide

<400> SEQUENCE: 69

```
gcgcgcatcg attgatggtt tatttctatt ataacgatat agattattaa gcaaagcttc    60
ttt                                                                 63
```

<210> SEQ ID NO 70
<211> LENGTH: 63
<212> TYPE: DNA
<213> ORGANISM: oligonucleotide

<400> SEQUENCE: 70

```
gcgcgctcta gaaaacatga ggattaccca tgtctaaagt aacttacatc atcaaagctt    60
cta                                                                 63
```

<210> SEQ ID NO 71
<211> LENGTH: 32
<212> TYPE: DNA
<213> ORGANISM: oligonucleotide

<400> SEQUENCE: 71

```
tgtatcaatg ttttattca tgggtgatcc tc                                  32
```

<210> SEQ ID NO 72
<211> LENGTH: 28
<212> TYPE: DNA
<213> ORGANISM: oligonucleotide

<400> SEQUENCE: 72

```
atgaataaaa acattgatac agttcgtg                                      28
```

<210> SEQ ID NO 73
<211> LENGTH: 48
<212> TYPE: DNA
<213> ORGANISM: oligonucleotide

<400> SEQUENCE: 73

```
gcgcgcctcg agctattatt tgttcgtata catctccagg tatcgata                48
```

<210> SEQ ID NO 74
<211> LENGTH: 21
<212> TYPE: DNA
<213> ORGANISM: oligonucleotide

<400> SEQUENCE: 74
ggatggcctt tttgcgtttc t                                        21

<210> SEQ ID NO 75
<211> LENGTH: 48
<212> TYPE: DNA
<213> ORGANISM: oligonucleotide

<400> SEQUENCE: 75
gcgcgcagat ctgaagatct tattaatcag ataaaatatt tctaggcg           48

<210> SEQ ID NO 76
<211> LENGTH: 63
<212> TYPE: DNA
<213> ORGANISM: oligonucleotide

<400> SEQUENCE: 76
gcgcgcctcg agaaacatga ggattaccca tgtctaaagt aacttacatc atcaaagctt   60
cta                                                            63

<210> SEQ ID NO 77
<211> LENGTH: 48
<212> TYPE: DNA
<213> ORGANISM: oligonucleotide

<400> SEQUENCE: 77
gcgcgcggat ccctattatt tgttcgtata catctccagg tatcgata           48

<210> SEQ ID NO 78
<211> LENGTH: 65
<212> TYPE: DNA
<213> ORGANISM: oligonucleotide

<400> SEQUENCE: 78
gcgcgctcta gaaaacatga ggattaccca tgatgaagca ctacgttatg ccaatccaca   60
cgtcc                                                          65

<210> SEQ ID NO 79
<211> LENGTH: 33
<212> TYPE: DNA
<213> ORGANISM: oligonucleotide

<400> SEQUENCE: 79
gcgcgcctcg agctattatg agatagcgtt cag                           33

<210> SEQ ID NO 80
<211> LENGTH: 50
<212> TYPE: DNA
<213> ORGANISM: oligonucleotide

<400> SEQUENCE: 80
gcgcgcgcat gcagatctgt atgcccaatg atcgagctgt tgtaattctc         50

<210> SEQ ID NO 81
<211> LENGTH: 42
<212> TYPE: DNA

<213> ORGANISM: oligonucleotide

<400> SEQUENCE: 81
gcgcgcctcg agccgcggct attagtagat accagagttt gc     42

<210> SEQ ID NO 82
<211> LENGTH: 39
<212> TYPE: DNA
<213> ORGANISM: oligonucleotide

<400> SEQUENCE: 82
caacacccag cggccgctgc gtatcaatga tcgagctgt     39

<210> SEQ ID NO 83
<211> LENGTH: 38
<212> TYPE: DNA
<213> ORGANISM: oligonucleotide

<400> SEQUENCE: 83
aagcttactc gaggatccct attagtagat accagagt     38

<210> SEQ ID NO 84
<211> LENGTH: 24
<212> TYPE: DNA
<213> ORGANISM: oligonucleotide

<400> SEQUENCE: 84
gctgccgctg ttagtcttcg ttcc     24

<210> SEQ ID NO 85
<211> LENGTH: 31
<212> TYPE: DNA
<213> ORGANISM: oligonucleotide

<400> SEQUENCE: 85
ctaccgcatt atagcttatc gatgataagc t     31

<210> SEQ ID NO 86
<211> LENGTH: 33
<212> TYPE: DNA
<213> ORGANISM: oligonucleotide

<400> SEQUENCE: 86
cgataagcta taatgcggta gtttacagtt aaa     33

<210> SEQ ID NO 87
<211> LENGTH: 58
<212> TYPE: DNA
<213> ORGANISM: oligonucleotide

<400> SEQUENCE: 87
ttattcctcc ttgcgttagc aatttaactg tgataaacta ccgcattata gcttatcg     58

<210> SEQ ID NO 88
<211> LENGTH: 79
<212> TYPE: DNA
<213> ORGANISM: oligonucleotide

<400> SEQUENCE: 88
cgataagcta taatgcggta gtttatcaca gttaaattgc taacgcaagg aataacatat     60
ggcttctaac ttcactcag     79

-continued

```
<210> SEQ ID NO 89
<211> LENGTH: 39
<212> TYPE: DNA
<213> ORGANISM: oligonucleotide

<400> SEQUENCE: 89
ccaccaccgg gtaccgtcgt tttacaacgt cgtgactgg                                    39

<210> SEQ ID NO 90
<211> LENGTH: 38
<212> TYPE: DNA
<213> ORGANISM: oligonucleotide

<400> SEQUENCE: 90
ccaccacacg gatccttatt tttgacacca gaccaact                                     38

<210> SEQ ID NO 91
<211> LENGTH: 88
<212> TYPE: DNA
<213> ORGANISM: oligonucleotide

<400> SEQUENCE: 91
ccaccacacg gatccttatt tttgacacca gacagttaaa ttgctaacgc aagagagagg             60
gcaccgcata tgcttctaac ttcactca                                                88

<210> SEQ ID NO 92
<211> LENGTH: 50
<212> TYPE: DNA
<213> ORGANISM: oligonucleotide

<400> SEQUENCE: 92
gttcgtactg gttgacaacg gcggtaccca cagtgactat atgggtggca                        50

<210> SEQ ID NO 93
<211> LENGTH: 30
<212> TYPE: DNA
<213> ORGANISM: oligonucleotide

<400> SEQUENCE: 93
atcgatgata agctgtcaat aatgagaatt                                              30

<210> SEQ ID NO 94
<211> LENGTH: 30
<212> TYPE: DNA
<213> ORGANISM: oligonucleotide

<400> SEQUENCE: 94
gttagcaatt taactgtgat aaactaccgc                                              30

<210> SEQ ID NO 95
<211> LENGTH: 30
<212> TYPE: DNA
<213> ORGANISM: oligonucleotide

<400> SEQUENCE: 95
tcaaccagta cgaactgagt gaagttagaa                                              30

<210> SEQ ID NO 96
<211> LENGTH: 40
<212> TYPE: DNA
<213> ORGANISM: oligonucleotide

<400> SEQUENCE: 96
```

```
                                                -continued cagcttatca tcgataagct ataatgcggt agttaatcac                                    40

<210> SEQ ID NO 97
<211> LENGTH: 21
<212> TYPE: DNA
<213> ORGANISM: oligonucleotide

<400> SEQUENCE: 97
tgacacacgg tcaatggttg g                                                        21

<210> SEQ ID NO 98
<211> LENGTH: 23
<212> TYPE: DNA
<213> ORGANISM: oligonucleotide

<400> SEQUENCE: 98
tgccacccat atagtcactg tgg                                                      23
```

HIGHLY EFFICIENT CONTROLLED EXPRESSION OF EXOGENOUS GENES IN E. COLI

This application claims the benefit of U.S. Provisional Application No. 60/072,794, filed Jan. 28, 1998, which is hereby incorporated by reference.

FIELD OF THE INVENTION

The present invention relates to new and improved expression vector systems capable of expressing exogenous genes, including toxic genes, in *E. coli* and other host cells. More specifically, the invention relates to highly efficient, tightly regulated expression vector systems which utilize the bacteriophage MS2 coat protein (MS2CP) and MS2 recognition site to control translation of the mRNA for any cloned gene in a host cell. In addition, the invention relates to expression vector systems which utilize transcriptional control proteins, e.g., motA and asiA of bacteriophage T4, to regulate transcription and provide a staged inducible promoter system which is much less complicated and much more versatile than the non-staged systems previously described.

BACKGROUND OF THE INVENTION

Prokaryotic cells have become the system of choice for expression of cloned genes encoding eukaryotic and prokaryotic polypeptides, and numerous expression systems exist for expression of gene products in bacteria. The expression of genes in *E. coli* has become established as a key technique in the understanding of molecular processes and *E. coli* expression systems have become a standard and popular method for the production and large-scale purification of exogenous proteins. Importantly, the technology has provided a source of proteins in a quantity and quality that was previously difficult, or impossible, to achieve through isolation from natural sources.

A number of patented expression systems for use in bacterial hosts have been described. In some instances, the expression systems described relate to generalized expression systems, while in other instances, the patented expression system is designed to allow relatively tight regulation, or is individually tailored for expression of a particular protein. Examples of such patents include U.S. Pat. No. 4,767,708 (construction of recombinant vector containing a cloned bacterial DNA polymerase I under the control of a positively regulated foreign promoter); U.S. Pat. No. 4,503,142 (construction of a class of cloning and expression vectors based on the use of the lac promoter/operator of *E. coli*); and U.S. Pat. No. 4,578,355 (use of the $P_L$ promoter of bacteriophage lambda to construct high level expression vectors).

Another widely used expression system, referred to as the pET vector expression system, makes use of the powerful T7 RNA polymerase to transcribe genes of interest; Studier et al., *J. Mol. Biol.*, 189:113–130 (1986). T7 RNA polymerase is highly selective for it own promoters, and no T7 promoters are known to be present in the DNA of *E. coli*. T7 uses its highly selective polymerase to direct transcription to its own DNA rather than to host DNA during infection, and a relatively small amount of T7 RNA polymerase provided from a cloned copy of T7 gene 1 is sufficient to direct high-level transcription from a T7 promoter in a multicopy plasmid. Moreover, T7 RNA polymerase is at least 5 times more active than *E. coli* polymerases; Id. Many heterologous proteins have been successfully expressed in high yields using the pET system; see, e.g. Dietrich et al., *Eur. J. Biochem*, 201:399–407 (1991); Lathrop et al., *Protein Expr. Purif.*, 3:512–517 (1992); Aukhil et al., *J. Biol. Chem.*, 268:2542–2553 (1993).

Unfortunately, these and other reported expression systems still suffer, to a greater or lesser degree, from such things as: 1) uninduced expression resulting from promoter leakiness; 2) inability to control expression to the extent necessary when the gene product will kill or otherwise seriously damage the host cell if expressed (more typically associated with expression of eukaryotic genes in bacteria); 3) the need to rely for induction of expression on either the host's biochemical responses or expensive or otherwise inadequate induction mechanisms; 4) inability to express gene of interest at sufficient levels; and 5) plasmid instability. Until such problems are adequately addressed and successfully overcome, the full potential of such expression systems will not be fully appreciated or utilized.

All known inducible promoter systems have a residual level of activity or "leakiness" which leads to the inappropriate transcription and expression of the gene being cloned under the control of the promoter. In most cases, this is not a problem because the gene product being produced is well tolerated by the cell, i.e., the gene product is non-toxic. However, in instances where the gene product being produced is toxic or even lethal to the cell, even these small amounts of expression can be detrimental. In fact, there are certain toxic genes that have been characterized as "unclonable" because they are unstable in any cloning vector.

Studier, F. W., *J. Mol. Biol.*, 219:37–44 (1991) addressed the problem of leaky expression in the pET vectors by developing the Lys series of vectors. These vectors harbor the gene for T7 lysozyme, which binds the T7 RNA polymerase present in the uninduced cell and prevents it from transcribing target genes. Dubendorff and Studier, *J. Mol. Biol.*, 219:45–59 (1991) addressed the problem by providing additional copies of lac operon control elements in the pET plasmids. Brown et al., *Gene*, 127:99–103 (1993) used induction by infection with a mutant T7 phage to successfully clone the toxic POL3 gene. Unfortunately, these and other reported systems fail to completely alleviate the leakage problem or suffer from the problems of plasmid instability and cell lysis associated with high levels of lysozyme and/or phage infection.

The present invention addresses and overcomes the problem of promoter leakiness by utilizing the translational repression capabilities of the bacteriophage MS2 coat protein. Bacteriophage MS2 is an RNA-containing phage with a fairly simple life cycle; Van Duin, J., *Single-Stranded RNA Bacteriophages in The Bacteriophages*, Chapter 4, pgs. 117–167, Plenum Press, New York (1988). The RNA encodes four genes, one of which is a replicase gene that copies the genome, another of which is the multifunctional coat protein gene. As the concentration of the coat protein increases in the cell, it forms a dimer and binds to a hairpin structure consisting of the ribosome binding site and ATG of the replicase gene. This binding then inhibits further translation from the replicase gene and effectively shifts the life cycle to the packaging of the genome.

The sequence of the MS2 coat protein has been published; Fiers et al., *Nature*, 260:500–507 (1976), mutants of the coat protein have been isolated and characterized; Peabody & Ely, *Nucleic Acids Research*, 20(7):1649–1655 (1992), and construction of a two-plasmid system for genetic analysis of the translational repressor activity of coat protein has been described; Peabody, D., *Journ. of Biol. Chem.*, 265(10):5684–5689 (1990).

Bacteriophage MS2 is not the only phage known to have proteins that bind messenger RNA and inhibit translation. For example, the RegA protein of bacteriophage T4 and the gene V protein of M13 are two other such proteins. However, a key difference between the RegA protein, gene V protein, and the MS2 coat protein relates to the placement of their recognition sites relative to the start site of the gene. For example, the RegA protein's recognition site is comprised of sequences in the coding region of the gene, thus limiting the genes that may be controlled by it. The gene V protein recognizes a sequence upstream of the ribosome binding sequence and thus may still allow a low level of translational initiation. For MS2, the binding site does not cover coding regions of the gene but does include the ribosome binding sequence and initiation codon. The MS2 system thus allows for the tightest possible repression, while still allowing for the site to be used universally.

The specific use of the MS2CP and MS2 recognition site will be described in more detail in the examples provided herein. As demonstrated by those examples, this unique use of the MS2 system allows one of ordinary skill in the art to effectively solve the problem of promoter leakage normally associated with the expression of heterologous genes in bacteria. From a commercial production standpoint, this is particularly useful because it is generally not favorable to be leaking product prior to the induction point. And, as relates to the ability to effectively express toxic genes, this can be of tremendous value to those working in the field, as some of these genes, if expressed in limited quantities, can have beneficial uses.

Another important aspect of bacterial expression system design is regulation of transcription. It is known that for many organisms the timing of gene expression is regulated by the production of specific transcription control proteins. This is particularly true for a number of different bacteriophage, as the progression through their life cycle is regulated by the appearance of different transcription proteins that lead to expression of whole classes of genes corresponding to that stage of their development. For example, it has been known for a long time that bacteriophage T4 moved through its life cycle in this way, and the actual mechanisms have recently been elucidated; Brody et al., *FEMS Micro. Letters,* 128:1–8 (1995). This lytic phage has three gene classes: early; middle; and late. The early gene promoters are very similar to strong *E. coli* promoters and are recognized immediately after infection by the host RNA polymerase. The accumulation of two early gene products, motA and asiA, shifts transcription to the middle mode.

The motA protein is a 23.5 kDa protein which guides the RNA polymerase to the T4 middle promoters by recognizing a sequence at the −30 region of the promoters. The asiA protein is a 10.5 kDa protein originally thought to be an anti-sigma factor protein, i.e., that it bound the sigma 70 of *E. coli* and rendered it non-functional. It is now thought, however, that binding of asiA to sigma 70 actually causes a conformational change that abolishes recognition of the −35 region of *E. coli* promoters, and the asiA protein may act as a bridge between the motA protein and the sigma 70 subunit. Moreover, asiA protein also inhibits recognition of T4 early promoters. motA and asiA are necessary and sufficient to specify transcription from T4 middle promoters. These details have been determined by in vitro transcription assays using purified motA and asiA and unmodified *E. coli* RNA polymerase; Ouhammouch et al., *Proc. Natl. Acad. Sci. USA,* 92:1451–1455 (1995).

The present invention provides a novel and new use of the T4 middle promoters to regulate transcription of any cloned gene in a prokaryotic host cell. The major advantages of this promoter system is that it directs transcription from specific promoters while inhibiting transcription from *E. coli* promoters, which thus minimizes competition for translational apparatus and inhibits the cell from responding to target protein production by inducing transcription of protease genes. Using the T4 middle promoter system described herein, it is also possible to express certain accessory proteins prior to target protein induction in a "staged" expression cycle that can be induced by a single signal, thus reducing the complicated nature of current expression protocols which generally require multiple induction events to accomplish such expression. The specifics of the T4 middle promoter system are described in the examples provided herein.

The present invention, through its utilization of the MS2 system to tightly regulate translation, and its utilization of T4 middle promoters to regulate transcription, provides highly efficient, tightly regulated expression vector systems capable of expressing exogenous genes, including toxic genes, in *E. coli*, and other host cells. The systems described herein, in addition to addressing the problems associated with other known systems, provide, for the first time, staged promoter systems which are much more versatile than the previously described systems. These systems will be of tremendous value to those working in the area of bacterial expression system design.

SUMMARY OF THE INVENTION

The present invention provides a translational repression system for use in cloning or expressing a heterologous gene in host cells, said system comprising a translational repressor operably linked to a constitutive promoter. In a preferred embodiment, the translational repressor is MS2 coat protein.

The invention further provides an improved process for cloning or expressing a heterologous gene, said process comprising culturing, under suitable conditions, host cells transformed with a plasmid vector, said vector comprising a DNA sequence encoding an inducible promoter, a DNA sequence encoding said heterologous gene linked to a translational repressor recognition site, and a DNA sequence encoding a translational repressor operably linked to a constitutive promoter; wherein said translational repressor controls expression of said heterologous gene. In a preferred embodiment, the translational repressor is MS2 coat protein. In one embodiment, the vector further comprises DNA sequence encoding 0.3–0.7 early genes of bacteriophage T7 (SEQ ID NO:2).

The invention further provides an improved process for cloning or expressing a heterologous gene, said process comprising culturing, under suitable conditions, host cells which have been co-transformed with a first plasmid vector comprising a DNA sequence encoding an inducible promoter and said heterologous gene linked to a translational repressor recognition site, and a second plasmid vector comprising a DNA sequence encoding a translational repressor operably linked to a constitutive promoter; wherein said translational repressor controls expression of said heterologous gene. In a preferred embodiment, the translational repressor is MS2 coat protein.

The invention further provides an improved process for cloning or expressing a heterologous gene, said process comprising culturing, under suitable conditions, host cells harboring a DNA sequence encoding a translational repressor operably linked to a constitutive promoter, transformed with a plasmid vector, said vector comprising a DNA sequence encoding an inducible promoter, and a DNA sequence encoding said heterologous gene linked to a translational repressor recognition site; wherein said translational repressor controls expression of said heterologous gene. In a preferred embodiment, the translational repressor is MS2 coat protein.

The invention further provides an improved process for cloning or expressing a heterologous gene, said process comprising culturing, under suitable conditions, host cells harboring a DNA sequence encoding an inducible promoter, a DNA sequence encoding said heterologous gene linked to a translational repressor recognition site, and a DNA sequence encoding a translational repressor operably linked to a constitutive promoter; wherein said translational repressor controls expression of said heterologous gene. In a preferred embodiment, the translational repressor is MS2 coat protein.

The invention further provides an "MS2 controlled T7 gene 1 cassette", said cassette comprising a DNA sequence encoding an inducible promoter, the MS2 recognition site linked to T7 gene 1, and the MS2 coat protein gene under the control of a weak constitutive promoter.

The invention further provides host cells capable of expressing a heterologous gene and harboring an "MS2 controlled T7 gene 1 cassette".

The invention further provides an improved process for expressing a heterologous gene, said process comprising culturing, under suitable conditions, host cells harboring an "MS2 controlled T7 gene 1 cassette" and transformed with an expression vector containing a DNA sequence encoding said heterologous gene under the control of a T7 promoter.

The invention further provides a series of host cells capable of cloning or expressing a heterologous gene, said host cells engineered to produce different concentrations of MS2CP.

The invention further provides a staged inducible promoter system for cloning or expressing a heterologous gene, said system comprising regulated transcriptional control proteins that direct transcription from specific promoters, while inhibiting general transcription from bacterial host promoters. In a preferred embodiment, the transcriptional control proteins are motA and asiA, and said proteins are regulated by MS2CP.

The invention further provides an improved process for cloning or expressing a heterologous gene, said process comprising culturing, under suitable conditions, host cells which have been co-transformed with a first plasmid vector comprising a DNA sequence encoding said heterologous gene under the control of T4 middle promoter, and a second plasmid vector comprising a DNA sequence encoding an inducible promoter, motA and asiA gene sequences each linked to a translational repressor recognition site, and a translational repressor operably linked to a constitutive promoter; wherein said translational repressor controls expression of said motA and asiA genes, and wherein said motA and asiA genes direct transcription from the T4 middle promoter while inhibiting transcription from said inducible promoter. In a preferred embodiment, the translational repressor is MS2 coat protein. In one embodiment, the second plasmid vector further comprises a DNA sequence encoding an accessory protein.

The invention further provides an improved process for cloning or expressing a heterologous gene, said process comprising culturing, under suitable conditions, host cells harboring a DNA sequence encoding an inducible promoter, motA and asiA gene sequences each linked to a translational repressor recognition site, and a translational repressor operably linked to a constitutive promoter, transformed with a plasmid vector comprising a DNA sequence encoding said heterologous gene linked under the control of T4 middle promoter; wherein said translational repressor controls expression of said motA and asiA genes, and wherein said motA and asiA genes direct transcription from the T4 middle promoter while inhibiting transcription from said inducible promoter. In a preferred embodiment, the translational repressor is MS2 coat protein.

The invention further provides an "MS2-based T4 cassette", said cassette comprising a DNA sequence encoding an inducible promoter, motA and asiA gene sequences each linked to an MS2 recognition sequence, and the MS2 coat protein gene under the control of a constitutive promoter.

The invention further provides a prokaryotic host cell capable of expressing a heterologous gene and harboring an "MS2-based T4 cassettes".

The invention further provides an improved process for cloning or expressing a heterologous gene, said process comprising culturing, under suitable conditions, host cells harboring an "MS2-based cassette" and transformed with an expression vector containing a DNA sequence encoding said heterologous gene under the control of a T4 promoter.

The invention further provides the DNA sequence of SEQ ID NO:1 and the DNA sequence of SEQ ID NO:2.

BRIEF DESCRIPTION OF THE DRAWINGS

FIG. 1 is the complete gene sequence (SEQ ID NO:1) of the wildtype MS2 coat protein used in the systems of the present invention. The gene has a NdeI site at the 5' end, and a BamHI site at the 3' end.

FIG. 17 is the complete gene sequence (SEQ ID NO:2) of the 3-7t operon constructed to contain the early genes (0.3–0.7) of T7.

FIG. 22 is the complete DNA sequence (SEQ ID NO:3) of the T4 PuvsX middle promoter used in the systems of the present invention. The gene has a AatII site at the 5' end, and a ClaI site at the 3' end.

FIG. 23 is the complete DNA sequence (SEQ ID NO:4) of the T4 PX middle promoter used in the systems of the present invention. The gene has a AatII site at the 5' end, and a ClaI site at the 3' end.

DETAILED DESCRIPTION OF THE INVENTION

Figure 2:
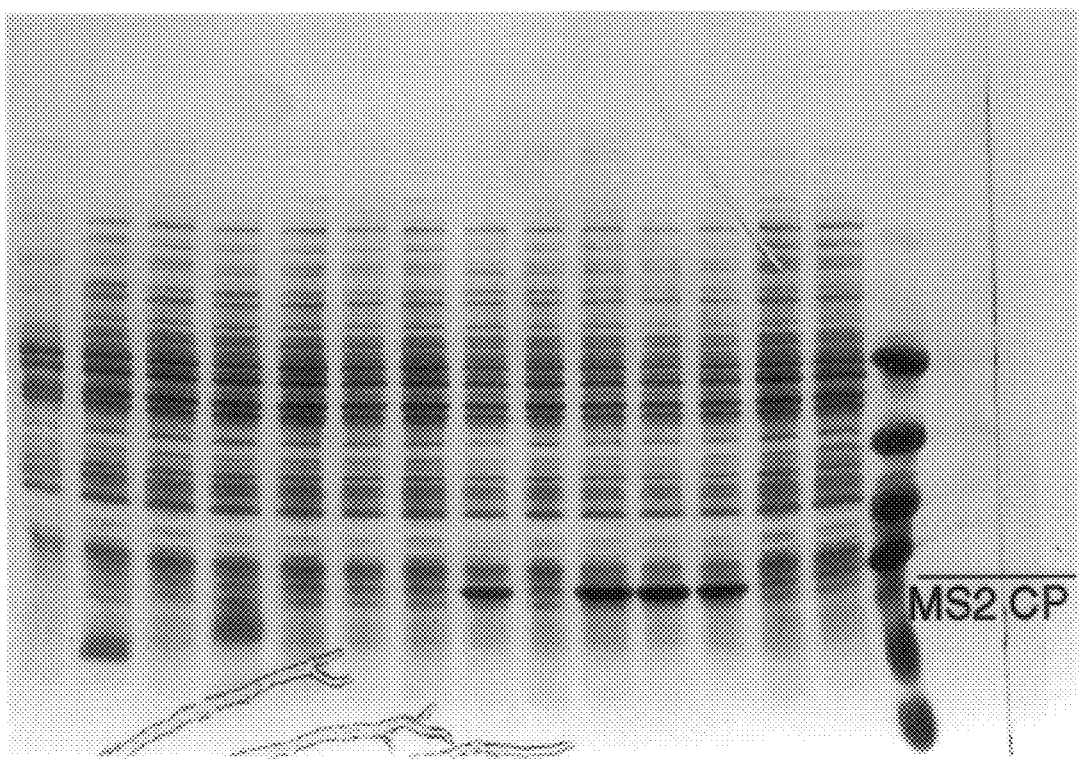
FIG. 2 is a photograph of an SDS gel showing the results of the wtMS2CP expression experiments. Lane 1 is an uninduced putative positive clone from BL21(DE3) host cells (containing the wtMS2CP gene in pT7-7) grown to an O.D. of 0.6; Lanes 2–14 are various putative positive clones from BL21(DE3) host cells (containing the wtMS2CP gene in pT7-7) after 4 hours of induction at 37° C. Lane 15 is the low range Amersham rainbow markers.

For purposes of the present invention, a "translational repressor" is defined as protein capable of specifically binding a recognition site on a piece of RNA and inhibiting translation. In the present invention, the MS2 coat protein and MS2 recognition site are used to provide a translational repressor system. Briefly, the published sequence of the MS2CP was used to generate oligonucleotides from which the intact gene was constructed. Then, after determining that MS2CP was tolerated at very high levels in *E. coli* without any apparent effect on cell growth, MS2CP was placed under the control of a weak constitutive promoter in plasmids of varying copy number. The idea was to continuously produce low levels of MS2CP so that any cloned genes which have an MS2 recognition site may be kept completely silent until it is useful to express them.

Using this approach, it was demonstrated that this MS2-based system could be used to provide an improved, tightly controlled system involving, e.g., the T7 RNA polymerase gene. Cloned T7 gene 1 provides a source of T7 RNA polymerase for directing selective, high-level expression of target genes under the control of a T7 promoter. However, because T7 RNA polymerase is so active and selective, it is important to control basal levels of active T7 RNA polymerase, i.e. shut off T7 gene 1 in the uninduced state, so as to prevent premature expression of the target gene.

The strategy utilized in the present invention thus involved the cloning of the T7 gene 1 with an MS2 recognition site linked to its coding sequence, and the insertion of this construct into the chromosome along with a copy of the MS2 coat protein under the control of a weak constitutive promoter. The two genes were cloned tail to tail such that the promoters for each were oriented in opposing directions. It was then demonstrated that host cells containing a chromosomal copy of this "MS2 controlled T7 gene 1" construct allowed for effective production of T7 RNA polymerase which could then be used to drive expression of a target gene.

Target genes successfully tested in the system of the present invention included T7 gene 1, neurotrophic factor-3 (NT-3), brain-derived neurotrophic factor (BDNF), serine protease inhibitor (SPI) and osteoprotegrin (OPG), neu differentiation factor (NDF) alpha/beta, hepatitis C polymerase, human telomerase, and analogs, derivatives and variants thereof. It is contemplated that the various MS2 controlled systems can provide improved control for any cloned gene, toxic or nontoxic, in a prokaryotic host cell.

It was further demonstrated that the MS2-based system could be used to stably clone and express certain toxic genes. As used herein, a toxic gene is any gene whose expression in the host cell will prevent the host cell in culture from achieving the normal logarithmic growth it would have achieved but for the expression of the toxic gene. As examples in the present invention, the early genes of bacteriophage T7 were cloned and expressed, as were motA and asiA. Several of the early genes of bacteriophage T7 are known to be toxic; Studier and Rosenberg, *J. Mol. Biol.*, 153:503–525 (1981). The 0.7 gene, in particular, is lethal as it encodes a function that inhibits *E. coli* RNA polymerase. motA and asiA are also now known to be toxic; Hinton et al., *Methods in Enzymol.*, 274:43–57 (1996). The ability to express such genes is of significant value because some of these genes have also been shown to have a positive effect on heterologous gene expression in *E. coli* by phage infection. In other words, there are times when it is useful to have a cloned copy of these genes present in the cell for expression just prior to the expression of the target gene.

In the examples provided herein, the T7 gene 1 was under the control of the UV5 lac promoter; Fuller, F., *Gene*, 19:43–54 (1982), the PS4 promoter; WO 95/267246 (Bartley et al.), published Oct. 12, 1995, and the lux promoter; U.S. Pat. No. 5,196,318 (Baldwin et al.), issued Mar. 23, 1993. Importantly, however, the T7 gene 1 could have been under the control of any inducible promoter, including bacterial promoters such as trp-, or lpp-; phage promoters such as a lambda $P_L$ or $P_R$; or synthetic promoters such as tac or trc.

Also developed and described herein as effective in the system of the present invention are mutant forms of the MS2CP. For example, a mutant version of the MS2CP in which the codon for the valine residue at position 29 has been changed to a codon for isoleucine was constructed. This mutation effects the ability of coat protein dimers to associate into capsid size aggregates; Peabody, D. S. and Ely, R., *Nuc. Acid Res.*, 20(7):1649–1655 (1992). Because the coat protein binds to its mRNA target as a dimer and multimerization of diners is thought to inhibit association with the mRNA, this mutation would thus be expected to increase the effective concentration of translational repressors present without increasing the actual protein concentration by keeping more coat protein in dimers rather than multimers. It would be understood by those of ordinary skill in the art that other mutant forms of the MS2CP would be effective in the systems of the present invention.

Although the examples provided herein specifically utilize the bacteriophage MS2 system, it would not be unexpected that other similar systems, e.g., Qβ, GA, SP, R17, f2 and fr, could be used as translational repressor systems in a similar manner.

Host cells used and evaluated in the present invention included the *E. coli* B strain BL21(DE3)±pLysS and the *E. coli* K strain EE1120±pLysS. It would clearly be understood by one of ordinary skill in the art that other commonly used *E. coli* B strains and K strains would be effective in the practice of the present invention. It would also be understood that various eukaryotic host cells could be utilized in the practice of the present invention.

Strong transcriptional terminators are also utilized in the systems of the present invention. By inserting such terminators upstream of the promoter of interest (e.g. the promoter directing expression of the T7 gene 1), read-through transcription from cryptic promoter sequences is eliminated, thus providing a more tightly regulated system. T1T2 terminators; Amman et al., *Gene*, 25:167–178 (1983) were used in the examples of the present invention; however, there are other strong terminators, e.g., $t_{HP}$; Nohno et al., *Mol. Gen. Genet.*, 205:260–269 (1986) that would clearly be expected to work effectively in the system of the present invention.

Although T7 RNA polymerase was used in the examples of the present invention, equivalent RNA polymerases from T7-like phages would also work. Such phages are described in detail in the art; see e.g., Hausmann, R., *The T7 Group in The Bacteriophages*, Chapter 8, pgs. 259–283, Plenum Press, New York (1988).

Also described in the present invention is the construction of a system for the activation of a cloned T4 middle promoter in vivo using a specially constructed operon consisting of motA and asiA genes under the control of an inducible promoter. The major advantage of this promoter system is that it directs transcription from specific promoters while inhibiting transcription from *E. coli* promoters, which minimizes competition for translational apparatus and inhibits the cell from responding to target protein production by inducing transcription of protease genes. It was also demonstrated that the system would provide a "staged" expression cycle that could be useful for, inter alia, expressing certain accessory proteins that may be helpful to the production of the target protein.

More specifically, the idea was that the accessory proteins could be cloned under a promoter that is induced in the same way as the motA and asiA promoter, or they could all be under the control of the same promoter in a single operon conformation. When the induction signal is given these accessory proteins and motA and asiA would be produced simultaneously. When motA and asiA reached saturating levels (equal to or somewhat higher then the number of RNA polymerase molecules present) then transcription from *E. coli* promoters would be inhibited, ending that stage of the expression cycle. The RNA polymerase would then be directed solely to T4 middle promoters which would lead to the expression of the target protein. There is currently no system available which can do this in *E. coli*.

The ability to express such accessory proteins in this manner can be of great benefit in improving expression of proteins in prokaryotic systems. For example, Yasukawa et al., *The Journ. of Biol. Chem.*, 270(432):25328–25331 (1995) reported that coproduction of the *E. coli* thioredoxin (Trx) or *E. coli* chaperones GroESL, increased the solubilities of various vertebrate proteins being produced in *E. coli* (Trx was most effective). This is an important and useful finding because eukaryotic proteins are frequently produced in *E. coli* as insoluble aggregates, and this is one of the barriers to studies of macromolecular structure.

In the present invention, the motA and asiA genes have been cloned under the lambda $P_L$ promoter and also cloned under a lac derived promoter. Importantly, however, any inducible promoter would work, including bacterial promoters such as trp-, or lpp-; phage promoters such as lambda $P_L$ or $P_R$; or synthetic promoters such as tac or trc.

Because the T4 middle promoters were found to be "leaky", and, more importantly, because the toxic genes motA and asiA need to be carefully controlled, the features of the MS2 system and the T4 middle promoter system were combined. motA/asiA operons were found to be unclonable unless both genes were linked to an MS2 recognition site. Optimal "MS2-based T4 cassettes" to be inserted into the host cell chromosome thus contain a motA-asiA inducible promoter with motA and asiA gene sequences (±accessory protein sequence) linked to an MS2 coat protein recognition sequence, and a MS2 coat protein gene operably linked to a weak constitutive promoter.

Utilizing this system, the low level production of MS2CP prevents T4 middle promoter leakage and motA/asiA production until an induction event occurs which then drives motA/asiA production (and accessory protein production, if intended) and shuts down *E. coli* transcription, followed by production of the target gene driven by T4 middle promoters.

Also developed and described herein are a series of *E. coli* strains which have been engineered to produce different concentrations of MS2CP. These strains have had the MS2 coat protein under the control of modified TET promoter sequences integrated into their chromosomal DNA at specific sites. The TET promoter sequences were modified by changing bases in the −10 and −35 regions to make them homologous with consensus sequence for these regions in strong *E. coli* promoters. They have also been altered by using oligonucleotides to randomize the sequence of the ribosome binding site. These changes allowed for the identification of a number of forms that produce higher levels of MS2 coat protein as determined by western analysis.

The various MS2-containing strains of the present invention can be utilized to clone toxic and other genes which cannot be cloned using conventional technology. For example, it has been determined that, when working with toxic genes, the establishment of the initial ligation is the step most sensitive to the toxicity and thus the most difficult step in the cloning process. Once a stable clone has been isolated however, it can then be transformed into other cell lines without incident. Using GM350, one could couple the toxic or "unclonable" gene to an MS2 recognition site and then use the ligation to transform GM350. Because GM350 has the highest production of MS2 coat protein; in fact, so much MS2CP is produced that expression upon induction is effectively eliminated, GM350 can be used to identify and obtain a stable clone. Once the stable clone has been obtained and sequence confirmed, the recombinant plasmid can be used to transform the other MS2 strains which produce decreasing amount of coat protein. The stability of the clone in each strain could be determined and the protein ultimately expressed in one such strain. In cases where toxicity persists subsequent to obtaining the initial clone, the low level MS2CP producers, e.g., GM315 and GM320 would be useful in stabilizing those constructs.

The following examples are offered to more fully illustrate the invention, but are not to be construed as limiting the scope thereof. Example 1 describes the construction of the wildtype MS2 coat (wtMS2CP) protein gene and then provides the results of testing of the wtMS2CP for its ability to be expressed in *E. coli*, and any effects that such expression had on cell growth. Example 2 describes the construction of two mutant versions of the MS2 coat protein gene. Example 3 describes the construction of the pRIN plasmid vectors containing wtMS2CP or MS2CP mutants for use in the development of the translational repression system. Example 4 describes the cloning of the T7 gene 1 into pRIN plasmid vectors, and the subsequent testing of the vectors for expression and system leakage. Example 5 describes the chromosomal insertion of "MS2 controlled T7 gene 1 cassettes" into the chromosome of a host cell, and then demonstrates the use of such host strains to express various target genes as well as providing the results of tests wherein the leakage and expression characteristics of the newly developed strains are compared to commercially available T7 RNA polymerase containing strains. Example 6 describes the large scale fermentation of the newly developed strains to high density. Example 7 describes the use of the MS2 system to clone various T7 early genes. Example 8 describes the testing of the T7 early genes in enhancing heterologous protein production. Example 9 describes the chromosomal insertion of the MS2 coat protein gene under the control of various altered TET promoters to produce strains engineered to produce different concentrations of MS2CP and the results of the testing of these strains for their ability to clone toxic genes. Example 10 describes the construction of the pAMGuvxs plasmid, the pAMGX plasmid, and the T4 operon pRIN systems used to develop the T4 middle promoter based system using multicopy plasmids. Example 11 describes the testing of the pAMGuvxs, pAMGX and T4 operon pRIN systems prepared and described in Example 10. Example 12 describes the cloning of the motA/asiA operon into single copy plasmids containing the MS2 system. Example 13 describes the testing of the single copy plasmids prepared and described in Example 12. Example 14 describes the use of the MS2/T4 based system to effectively express an accessory protein and thereby enhance expression of a target protein.

Materials and Methods

In the following examples, the following bacterial plasmids/expression vectors are utilized: pAMG13, pAMG21, pAMG22, pAMG25, pAMG33, and 3002 nahG (each of which has been previously deposited or is being deposited in connection with the filing of this application); pT7-7; Tabor and Richardson, *Proc. Natl. Acad. Sci. USA*, 82:1074–1078 (1985); pACYC184; Chang et al., *J. Bacteriol.*, 134:1141–1156 (1978); Rose, *Nucleic Acid Res.*, 16:355 (1988a); pKK223-3; Amman et al., *Gene*, 25:167–178 (1983); pGP1-2; Tabor and Richardson, *Proc. Natl. Acad. Sci. USA*, 82:1074–1078 (1985); and pSC101; Bernardi and Bernardi, *Nuc. Acids Res.*, 12:9415–9426.

In the following examples, the methods provided below were used unless otherwise noted.

1. Ligations

All ligations were carried out in a final volume of 40 μl. Approximately 50 ng to 500 ng of each vector was used and from 500 ng to 2 μg of each insert was used. T4 DNA ligase was added at 1 unit of activity and the reactions are incubated at 16° C. overnight. The reactions were then precipitated by the addition of ammonium acetate to 2.5M and 2.5 volumes of ethanol was added. The reaction mixture was then incubated at −80° C. for at least 1 hour and then spun at 15,000 rpm (at 4° C.) for 30 minutes. The pellet was resuspended in the original 40 μl and a 4 μl aliquot was used for electroporation.

2. Kinasing and Annealing Oligonucleotides

Oligonucleotides were resuspended in water at a concentration of 20 pmol/μl. A 12.5 μl aliquot of each oligonucleotide is used for the kinasing reaction. To this is added 2 μl of ATP, 2 μl of ligation buffer and 2.5 μl of water. The reaction is started by the addition of 1 μl of PNK and is incubated at 37° C. for 1 hour. The samples are then heated to 65° C. for 15 minutes. Complimentary pairs are then mixed and heated to 100° C. for 1 minute and allowed to slow cool to room temperature and then placed on ice. At this point the annealed oligonucleotides are ready to ligate. For particularly long sequences two oligonucleotides would be ordered that spanned the entire region and had 6–12 bases of complimentarity at the 3' ends. These would be used as both template and primer (at 1 pmol/μl final concentration) in 100 μl PCR reactions and after gel purification would be restriction digested prior to ligation.

3. PCR Reactions

Several standard programs were used routinely for PCR procedures. When amplifying genes or operon fragments the reaction volume was 100 μl. A 10 μl aliquot of each primer at 10 pmol/μl is added to each reaction and the template is added at between 50 ng to 250 ng. Reactions are run for 25 cycles. The first step is 94° C. for 30 seconds, then 50° C. for two minutes followed by 72° C. for three minutes. The amplified fragments were gel purified in SeaKem GTG (FMC) agarose gels. The DNA was recovered from the agarose using Qiaex II (Qioagen Inc.)

Colony screening reactions to identify positive clones are run in 20 μl volumes. The oligonucleotides are present at a final concentration of 0.25 pmol/μl. Colonies are picked using a pipette tip and dissolved into the reaction mixture. A 1 μl aliquot is removed and used to innoculate a 5 ml tube of LB containing the appropriate antibiotic. The PCR reactions are run for 30 cycles. The first step is 94° C. for 30 seconds followed by a 30 second annealing at 37° C. and a 30 second elongation at 72° C. For large inserts (>1000 bases) the elongation time is extended to 1 minute. The reactions are then loaded onto agarose gels (0.8–1.0%) and positives are identified by migration against standards and vector mock reactions.

EXAMPLE 1

This example describes the construction of the wildtype MS2 coat protein gene (wtMS2CP) and then provides the results of testing of the wtMS2CP for its ability to be expressed in *E. coli*, and any effects that such expression had on host cell growth.

The published protein sequence of the MS2 coat protein; Peabody, D., *EMBO J.*, 12(2):595–600 (1993) was used to design a gene using *E. coli* preferred usage codons. Oligonucleotides 909–34 through 909–53 (See Table 1) were designed and used to construct the gene, and the complete gene sequence is depicted in FIG. 1. The oligonucleotides were designed to include an NdeI site at the 5' end of the gene and a BamHI site at the 3' end. This gene was then restriction digested with BamHI and NdeI and cloned into plasmid pT7-7; Tabor and Richardson, *Proc. Natl. Acad. Sci. USA*, 82:1074–1078 (1985). Once a positive clone had been identified and the sequence confirmed, this gene was subcloned into plasmid 3002 nahG using the same restriction sites.

The commercially available BL21(DE3) strain (Novagen, Madison, Wis.) was used to test the ability of the wtMS2CP to be expressed in *E. coli*. BL21(DE3) is an *E. coli* B strain which contains a chromosomal copy of the T7 RNA polymerase gene under the control of the UV5 lac promoter. Colonies of BL21(DE3) containing the wtMS2CP gene in pT7-7 were picked from plates and used to inoculate a 5 ml aliquot of LB-amp in a 50 ml Falcon tube. This preparation was grown overnight at 28° C. with shaking. The overnight culture was used to inoculate fresh media at a 1:100 dilution (50 μl to 5 ml) in a 15 ml tube. These were grown at 28° C. with shaking to an approximate O.D. of 0.6.

Expression of the wtMS2CP gene was induced by the addition of IPTG to 0.4 mM. Incubation was continued at 37° C. with shaking for 4 hours. A 1 ml sample was removed and the cells were pelleted by centrifugation. The pellets were resuspended in cracking buffer at 0.01 OD unit/μl and samples were boiled for 5 minutes. A 6 μl aliquot of each sample was loaded onto a 4–20% SDS polyacrylamide gel (Novex). The gel was stained with coomassie blue to visualize the proteins. As depicted by the gel picture (FIG. 2), lanes 8, 10, 11 and 12 display production of the wtMS2CP. These producing cultures reached a higher optical density than those that did not contain functional versions of the MS2CP gene in pT7-7, thus demonstrating that MS2CP can be effectively expressed with no apparent affect on host cell growth.

EXAMPLE 2

This example describes the construction of two mutant versions of the MS2 coat protein gene.

A mutant version of the MS2 coat protein gene in which the codon for the valine residue at position 29 has been changed to a codon for isoleucine was constructed by overlapping PCR using oligonucleotides 1456–55 and 1456–56 (See Table 1). This particular mutant will hereinafter be referred to as MS2CP-11.

A mutant version of the MS2 coat protein gene in which the codon for the cysteine residue at position 101 has been changed to a codon for arginine was constructed by overlapping PCR using oligonucleotides 1456–61 and 1456–62 (See Table 1). This particular mutant will hereinafter be referred to as MS2CP-14.

EXAMPLE 3

This example describes the construction of the pRIN plasmid vectors containing wtMS2CP or MS2CP mutants for use in the development of the translational repression system. The pRIN vectors are multicopy vectors (15 copy) based on the plasmid pACYC184; Chang et al., *J. Bacteriol.*, 134:1141–1156 (1978); Rose, *Nucleic Acid Res.*, 16:355 (1988a).

The pACYC184 plasmid was digested with restriction enzymes XbaI and HindIII. Oligonucleotides 940–29 and 940–30 (See Table 1) were designed to ligate into these sites while introducing new unique sites for later use. Specifically, the annealed oligonucleotides were cloned into the cut pACYC184 vector, thus killing the XbaI and HindIII sites and introducing unique PstI and SacI sites as well as a second SphI site. This plasmid was then digested with restriction enzyme EagI and oligonucleotides 941–43 and 941–44 (See Table 1) were cloned into the vector which destroyed the EagI site and introduced a unique AatII restriction site.

The 1036–99 fragment (See Table 1) containing the wildtype MS2 coat protein gene linked to the nahG promoter was PCR constructed from the 3002 nahG clone described in Example 1, such that a SacI site was upstream of the promoter sequence and a BamHI site was at the terminus of the gene. This fragment was then cloned into the pACYC184-derived vector (described in the previous paragraph) from SacI to BamHI.

The nahG promoter sequence was then replaced with a TET promoter sequence as follows: a synthetic TET promoter was constructed using oligonucleotides 1016–20 and 1016–21 (See Table 1). The promoter was designed using the TET promoter sequence native to pACYC184 with the alteration of the introduction of an NdeI site at the natural start of the TET gene. The promoter was put into the construct from SacI to NdeI such that the wtMS2CP gene was operably linked to the TET promoter.

A DNA fragment containing the rrnB T1T2 terminator sequences was constructed by PCR using plasmid pKK223-3; Amman et al., *Gene*, 25:167–178 (1983) as a template and using oligonucleotides 1036–6 and 1053–71 (See Table 1). This fragment was constructed to have sites for restriction enzymes AatII and AvaI at the ends. The pACYC184-derived vector described above was cut with these enzymes and this fragment was ligated in.

Figure 3:
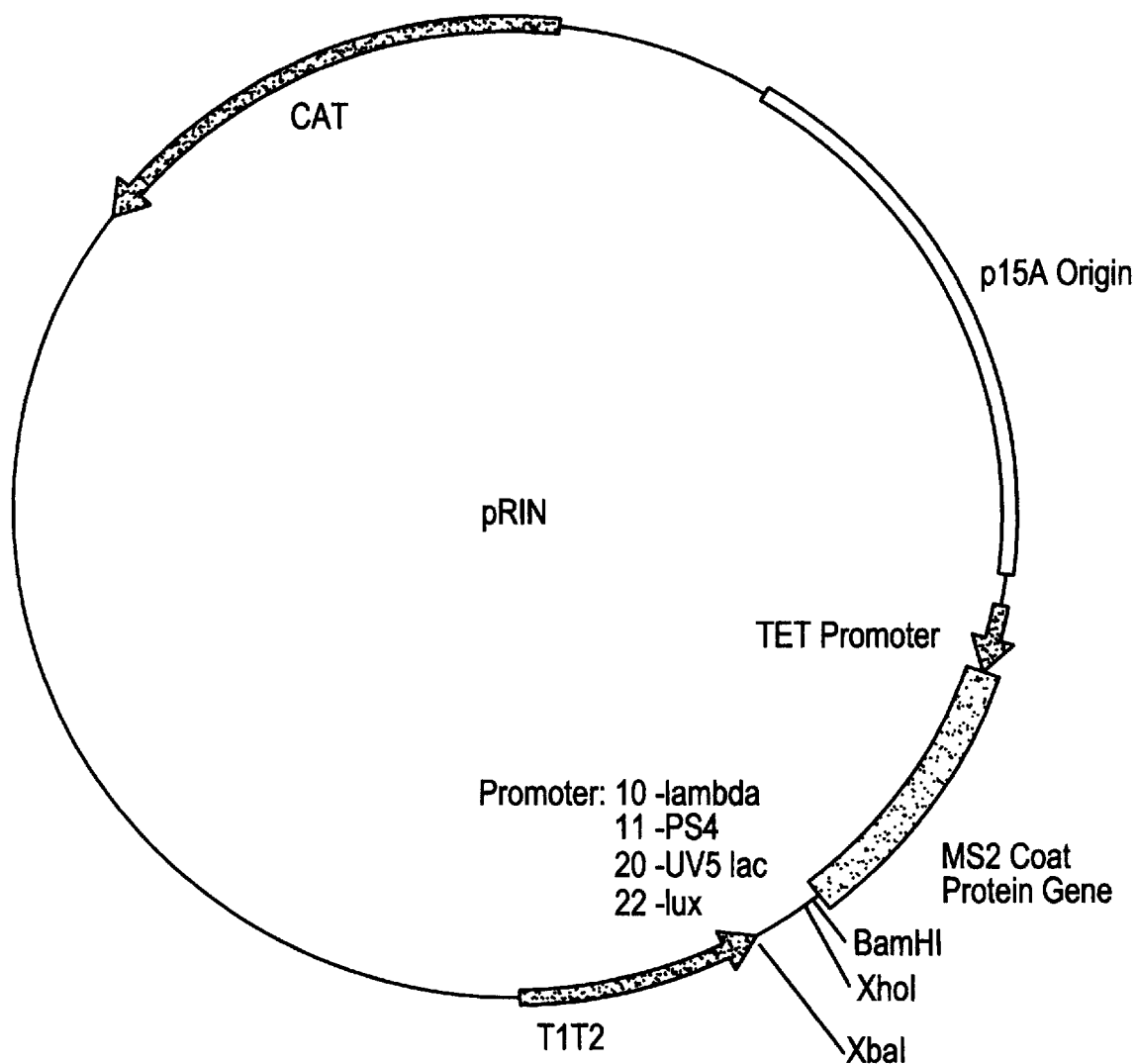
FIG. 3 is a schematic diagram of the pRIN plasmid vectors developed in the present invention.

A synthetic version of a lambda promoter and the multiple cloning site from vector pAMG13 were cut out from AatII to BamHI. The pACYC184-derived vector described was then cut with these enzymes and the fragment from pAMG13 ligated in. The resulting plasmid was named pRIN10(wt)(FIG. 3). Three similar pACYC184-derived plasmids, one containing the PS4 promoter instead of the lambda promoter (named pRIN11(wt)), one which contained the UV5 lac promoter instead of the lambda promoter (named pRIN20(wt)), and one which contained the lux promoter (named pRIN22(wt)) were also constructed (FIG. 3).

pRIN constructions containing the MS2CP-11 and MS2CP-14 mutants were also constructed. Fragments of the mutant forms, still linked with the TET promoter, were generated so as to have a SphI site at the promoter end, and a BamHI at the end of the MS2CP mutant gene. The pRIN plasmids described above were cut with BamHI and SphI and the plasmid portion was gel purified away from the wtMS2CP fragment. The mutant fragments were then ligated in using the SphI and BamHI sites. The constructions containing the MS2CP-11 mutant were named pRIN10(11), pRIN11(11), pRIN20(11), and pRIN22(11), and the constructions containing the MS2CP-14 mutant were named pRIN10(14), pRIN11(14), pRIN20(14) and pRIN22(14).

EXAMPLE 4

This example describes the cloning of the T7 gene 1 into various pRIN plasmid vectors, and the subsequent testing of the plasmid vectors for expression and system leakage.

The T7 gene 1 was cloned into the various pRIN plasmids described above. The T7 gene 1 gene was PCR constructed using oligonucleotides 949–1 and 949–2 (See Table 1) to have an MS2 coat protein recognition sequence linked to its coding sequence. The template used was plasmid pGP1-2; Tabor and Richardson, *Proc. Natl. Acad. Sci. USA*, 82:1074–1078 (1985). The gene was cloned into the various pRIN plasmids from XbaI to BamHI. The MS2CP mutants were tested for their ability to inhibit multimerization and thus lead to an increase in the effective concentration of translational repressor. Another parameter that was examined was the presence or absence of a downstream box sequence in gene 1 (oligonucleotide 1477–84)(See Table 1) (this sequence has been shown to enhance translation by increasing binding to the ribosome; Sprengart et al., *Nuc. Acids Res.*, 18(7):1719–1723 (1990)).

Overnight cultures of the various constructs were grown in 5 ml of LB-cam in 50 ml tubes at 28° C. These were used to inoculate fresh 5 ml portions of LB-cam in 15 ml tubes at 1:100 dilution. These were all returned to a 28° C. shaker. Samples were taken of the cultures just prior to induction, and the induction step in this case involved the addition of IPTG to a final concentration of 0.4 mM. Incubation of induced cultures was continued for 3 hours and 1 ml samples were taken. All samples were pelleted by centrifugation and the pellets were resuspended in cracking buffer. After boiling for 5 minutes, a 6 $\mu$l aliquot of each was run on a 4–20% SDS polyacrylamide gel (Novex).

Protein was then electrophoretically transferred to nitrocellulose. The blots were blocked overnight in blotto-tween with 2% non-fat dry milk; Harlow & Lane, *Immunoblotting in Antibodies, A Laboratory Manual*, Chapter 12, Cold Spring Harbor Laboratory Press, (1988). The blots were probed for 1 hour with a rabbit derived polyclonal antibody to T7 RNA polymerase. After washing the blots were probed with donkey anti-rabbit horse radish peroxidase conjugated antibody (Amersham) for 1 hour. This was washed and treated with ECL reagents (Amersham) and exposed to X-ray film. The exposure was for 15 minutes to maximize sensitivity. The film was developed using a Kodak film processor.

Figure 4:
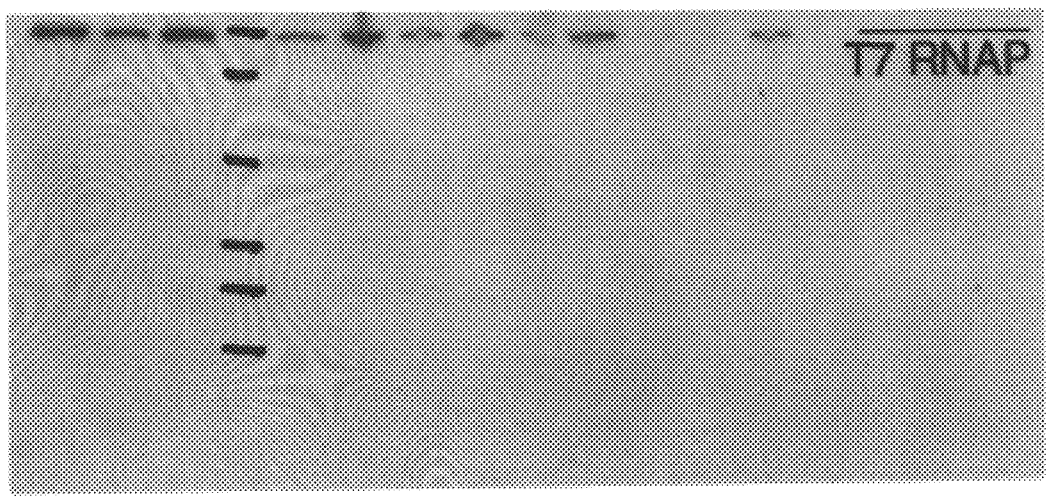
FIG. 4 is a photograph of a western blot showing the results of an expression and leakage experiment carried out with various pRIN plasmid vectors into which the T7 gene 1 had been cloned. This particular blot is of an overnight stationary culture, and each set of lanes is T7 gene 1, plus or minus (m) a downstream box, in the same vector. The first three sets of lanes use pRIN11 (PS4 promoter) with various MS2CPs. The last three sets of lanes use pRIN20 (UV5 lac promoter) with various MS2CPs. Lane 4 is the low range Biorad molecular weight marker.
Figure 5:
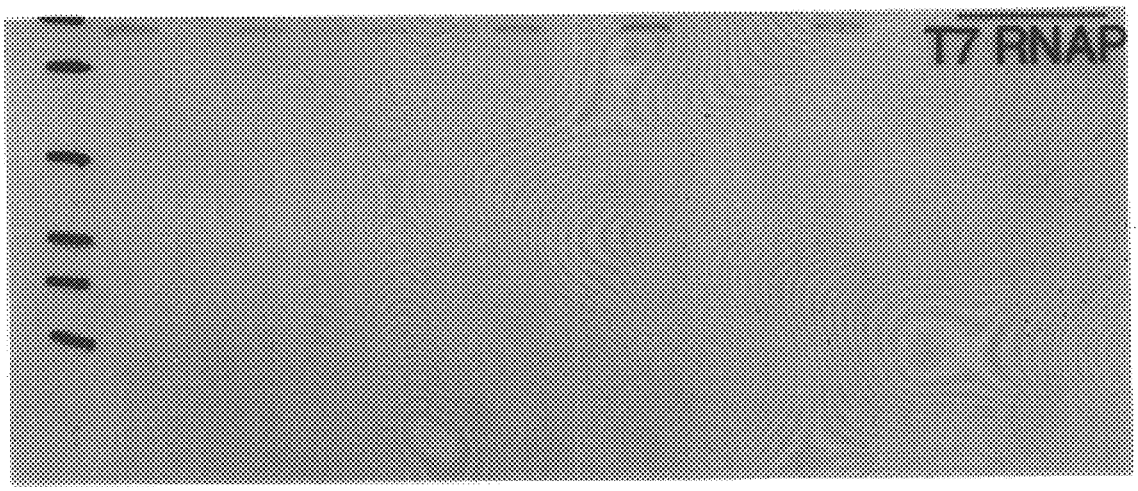
FIG. 5 is a photograph of a western blot showing the results of an expression and leakage experiment carried out with various pRIN plasmid vectors into which the T7 gene 1 had been cloned. This particular blot is of an exponentially growing preinduction culture (preI), and each set of lanes is T7 gene 1, plus or minus (m) a downstream box, in the same vector. The first three sets of lanes use pRIN11 (PS4 promoter) with various MS2CPs. The last three sets of lanes use pRIN20 (UV5 lac promoter) with various MS2CPs. Lane 1 is the low range Biorad molecular weight marker.
Figure 6:
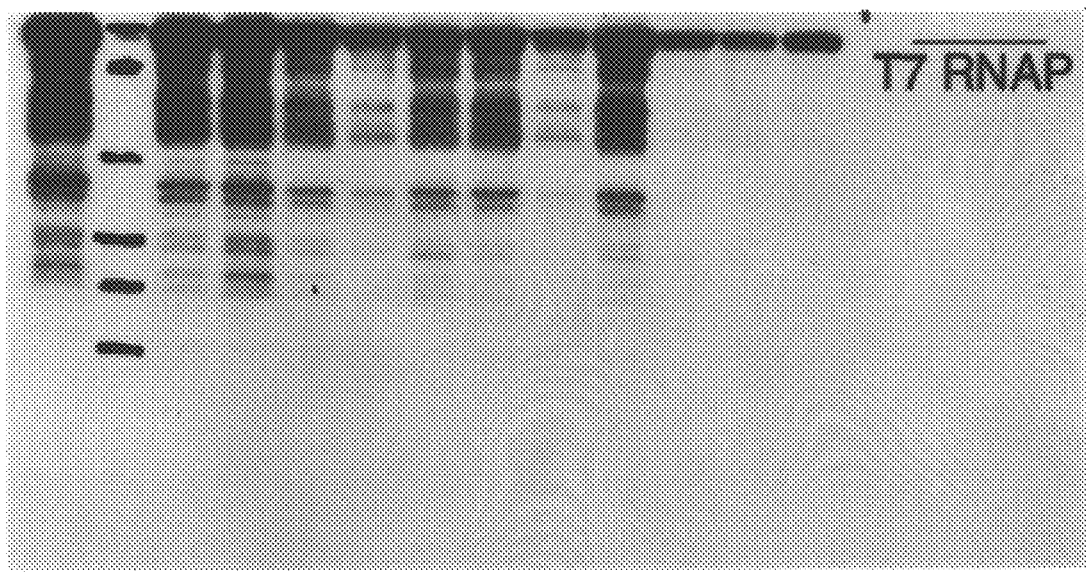
FIG. 6 is a photograph of a western blot showing the results of an expression and leakage experiment carried out with various pRIN plasmid vectors into which the T7 gene 1 had been cloned. This particular blot is of an IPTG induced culture grown at 28° C., and each set of lanes is a downstream box plus or minus (m) gene 1 in the same vector. The first three sets of lanes use pRIN11 (PS4 promoter) with various MS2CPs. The last three sets of lanes use pRIN20 (UV5 lac promoter) with various MS2CPs. Lane 2 is the low range Biorad molecular weight marker.

FIGS. 4–6 are photographs of western blots showing the results of leakage and expression experiments carried out with various constructs. FIG. 4 is a blot of an overnight stationary culture, FIG. 5 is a blot of an exponentially growing preinduction culture (preI) and FIG. 6 is a blot of an IPTG induced culture grown at 28° C. As evidenced by the pictures of the blots, it is clear the presence of the coat protein has a dramatic effect on overnight leakage (compare FIG. 4 and 5), and there is some reduction of the level of protein accumulation in the cells that show the greatest control of leakage. More specifically, the signal is stronger on the left side lanes of the blots and decreases in the right side lanes as a function of the tightness and degree of control exercised by the corresponding systems; the PS4 promoter is leakier than the UV5 lac promoter; the mutatation of the downstream box lowers leakage, but has little impact on induction level for the PS4 promoter; the MS2CP mutants display tighter control of T7 gene 1 leakage in overnight and exponential cultures than does wildtype; the mutants impact the level of accumulation upon induction, with the more tightly controlled overnight cultures (UV5 lac) displaying lower levels of RNA polymerase after induction; and the MS2CP14 mutant appears to have a greater effect then the MS2CP11 mutant, which is intermediate between wtMS2CP and MS2CP14.

EXAMPLE 5

This example describes the chromosomal insertion of "MS2 controlled T7 gene 1 cassettes" into the chromosome of a host cell, and then demonstrates the use of such host strains to express various target genes as well as providing the results of tests wherein the leakage and expression characteristics of the newly developed strains are compared to commercially available T7 RNA polymerase containing strains.

Figure 7:
FIG. 7 is a schematic diagram of a "MS2 controlled T7 gene 1 cassette".

A "MS2 controlled T7 gene 1 cassette" (contains the upstream terminator sequences, an inducible promoter sequence, the MS2 recognition site, the T7 gene 1, the MS2 coat protein gene (wtMS2CP, or MS2CP-11 or MS2CP-14) and a weak constitutive promoter, e.g., TET)(See FIG. 7) was cut out of the various pRIN plasmids using restriction enzymes SphI and PpuMI, and then cloned into a specially constructed M13 vector, MMEbg; Blum et al., *J. Bacteriology*, 171(1):538–546 (1889); Micheals, M. L., *Gene*, 93:1–7 (1990) for site specific integration into the host chromosome. Various cassettes containing either wtMS2CP, MS2CP-11, or MS2CP-14 were obtained.

The integration proceeds through a forced recombination mechanism. First, oligonucleotides 1553–73 and 1553–74 (See Table 1) were ligated into the BamHI and NotI sites of MMebg. These oligonucleotides introduce unique SphI and PpuMI sites into the vector. The "MS2 controlled T7 gene 1 cassette" was then ligated into the SphI and PpuMI sites. Ligations were then transformed into XL1 Blue cells by putting the cells into 1 ml SOC and plating 150 µl of MOCK ligation and 150 µl and 30 µl of insert ligations with 300 µl XL1 Blue overnight culture+3.5 ml LB+0.8% Top Agar. The mixture was poured over LB plates and incubated at 37° C. overnight. Plaques were picked into 100 µl of 1X TE.

Overnight cultures were started before PCR screening with 70 µl of resuspended phage from plaques and 200 µl XL1 Blue ON in 5 ml LB. These cultures were shaken at 37° C. overnight. Each plaque was screened by PCR. 2 µl of the resuspended plaque in a 20 µl PCR reaction was used. Oligonucleotides 305–3 and 305–14 (internal for T7 gene 1)(See Table 1) were used for this screening. Positive clones were identified by running reactions out on a 1.0% agarose gel. A 1 ml aliquot of each overnight culture was spun down and 800 µl of supernatant with phage saved in an Eppendorf tube. A 200 µl aliquot of each supernatant was then incubated at 70° C. for 20 min. 100 µl of the heat treated phage is then added to 500 µl of an autotrophic K strain of *E. coli* with a genotype of lac $i^Q$ (named F'tet/GM120 cells) from an overnight culture. (GM120 has ATCC Accession No. 55764). These samples were incubated at 37° C. for about 1 hour. 25 µl of control F'tet/GM120, 25 µl of heat treated phage alone, and 25 µl of 1:10 dilution of each cross were then plated on LB+Kn$^{40}$ plates. The plates were then incubated at 37° C. overnight. Purified colonies that resulted from the cross (or lysogenization) were streaked two times on LB+Kn$^{40}$ plates and incubated at 37° C. overnight. The colonies were then subcultured two times into 0.3% ox gall bile and LB, and then shaken at 37° C. overnight. Cells were then streaked on LB plates, along with a replica plating from LB to LB+Kn to identify the kanamycin sensitive colonies (the phage should no longer be present in the colonies that are kanamycin sensitive).

PCR screening was then performed to check for insertion into the chromosome as follows: a colony was picked from a plate and used to inoculate 20 µl of PCR mix (5 ml LB also inoculated, using the same tip, to be used for an overnight culture if a positive were identified). 15 µl of each PCR sample was run on a 1.0% agarose gel to check for positives. When positives were identified by size on the gel, the corresponding overnight cultures were started shaking at 37° C. These were then plated onto LB plates and incubated at 37° C. overnight.

To cure the cells of the F' factor, cultures from single colonies from the plate in 5 ml LB were started shaking at 37° C. for 4 hours. A published protocol for curing using acridine orange was then followed; Miller, *Experiments in molecular genetics*, Cold Spring Harbor Laboratory Press, pgs. 104–106 (1972). Basically, you plate cells to LB and replica plate to LB+tetracycline. The tetracycline sensitive cells will be isolated as F' minus. Overnight cultures of the colonies from these plates are started and then reinfected with M13 mp18 to ensure that the F' factor is no longer present in the cells. 300 µl of overnight cultures is then mixed with top agar and spotted with 2 µl of M13 mp18 phage stock. There should be no plaques present. Two strains constructed using this protocol were named EE11-11M (PS4 promoter) and E11-20 (UV5 lac promoter).

The leakage and expression characteristics of EE11-11M and EE11-20 were compared to the commercially available BL21(DE3) strain (described previously), using expression of product gene NT-3 or product gene BDNF as a marker. NT-3 (or BDNF) is present in the commercially available pET22b vector (Novagen, Madison, Wis.) which also has a lac i site between the T7 promoter and the gene of interest, and carries a lac $i^Q$ gene to reduce leakage. Also compared were BL21(DE3) containing pLysS as a secondary vector vs. EE11-11M containing pLysS as a secondary vector vs. EE11-20 containing pLysS as a secondary vector (as stated previously, pLysS carries the T7 lysozyme gene which inhibits T7 RNA polymerase and is a recommended way to reduce leakage). Finally, a pAMG25 plasmid which contained the BDNF gene was also used to compare BL21 (DE3) vs. EE11-20.

Specifically, overnight cultures (5 ml) of LB+antibiotic ($Kn^{40}$ or $Cm^{30}$) in 50 ml Falcon tubes were started and these cultures were shaken at 28° C. Fresh tubes of 5 ml LB+antibiotic in 14 ml glass tubes were inoculated with 1:100 dilution of the overnight culture. Tubes were shaken at 28° C. until they reached an $OD_{600}$=~0.8. overnight cultures continued to shake at 28° C. until the conclusion of the experiment. Aliquots of each sample were taken prior to induction. Cultures were induced by the addition of 20 $\mu l$ 100 mM IPTG (which gave 0.4 mM final concentration for IPTG). Induced cultures were incubated at 28° C. with shaking for 4 hours. A 1 ml sample of the culture was withdrawn and spun down in a 1.5 ml Eppendorf tube at 15,000 rpm (at 4° C.)(Tomy MTX-160) for 5 minutes. The supernatant was decanted and the pellet retained. Pellets were then resuspended in cracking buffer at 0.01 OD unit/$\mu l$. Samples were then heated to 100° C. in heat block for 5 minutes, then cooled for 2–3 minutes and then 6 $\mu l$ of each sample loaded on a 4–20% Tris-Glycine SDS polyacrylamide gel in 1X Tris-Glycine running buffer with 2% SDS added. The gel was run at 150V for 1.3 hours. The gel was stained with coomassie blue to visualize the protein.

Figure 8:
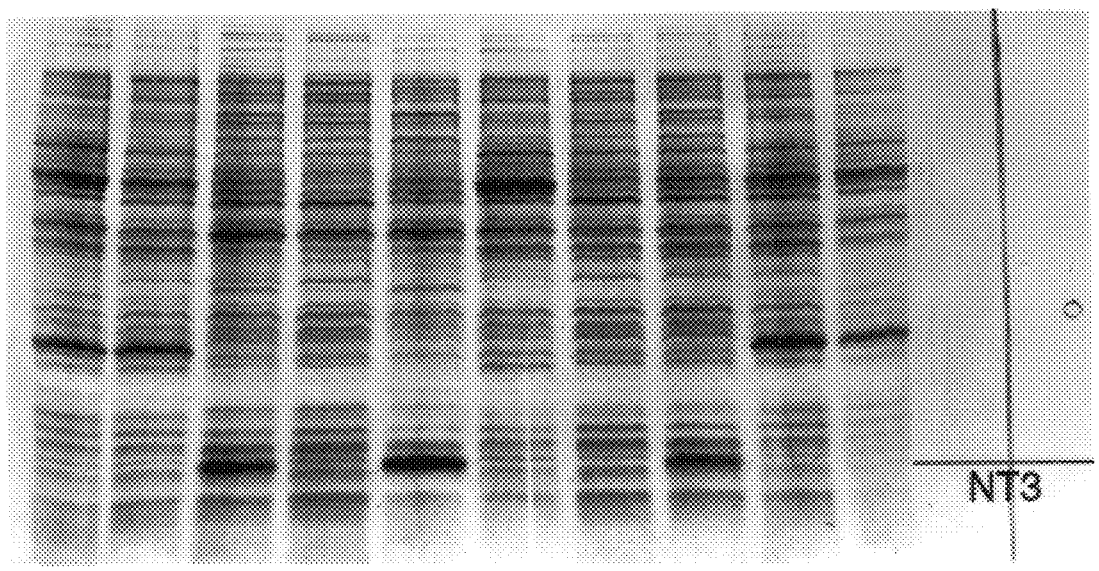
FIG. 8 is a picture of an SDS gel which compares the leakage and expression characteristics of the commercially available BL21(DE3) strain (lanes 3–5), the BL21(DE3) strain containing pLysS as a secondary vector (lanes 1–2), the EE11-20 strain (lanes 6–8), and the EE11-20 strain containing pLysS as a secondary vector (lanes 9–10). Comparisons were based on expression of NT-3 as the target product gene. Lanes 1, 5, 6 and 10 represent overnight (ON) cultures, lanes 4 and 7 represent preinduction (preI) cultures, and lanes 2, 3, 8 and 9 represent induction (using IPTG at 28° C.) (I-28) cultures.
Figure 9:
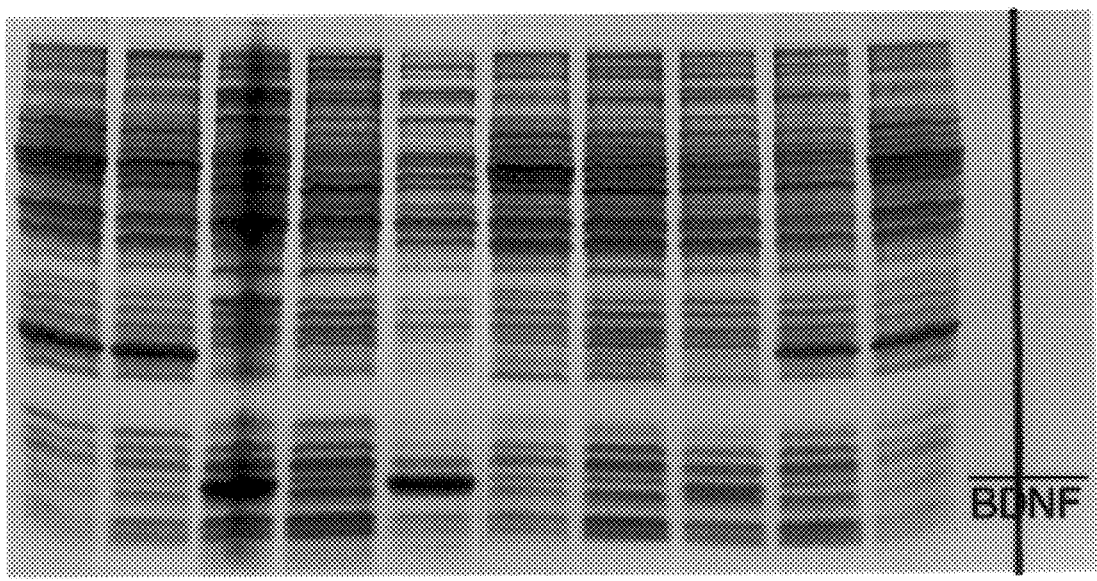
FIG. 9 is a picture of an SDS gel which compares the leakage and expression characteristics of the commercially available BL21(DE3) strain (lanes 3–5), the BL21(DE3) strain containing pLysS as a secondary vector (lanes 1–2), the EE11-20 strain (lanes 6–8), and the EE11-20 strain containing pLysS as a secondary vector (lanes 9–10). Comparisons were based on expression of BDNF as the target product gene. Lanes 1, 5, 6 and 10 represent overnight (ON) cultures, lanes 4 and 7 represent preinduction (preI) cultures, and lanes 2, 3, 8 and 9 represent induction (using IPTG at 28° C.) (I-28) cultures.
Figure 10:
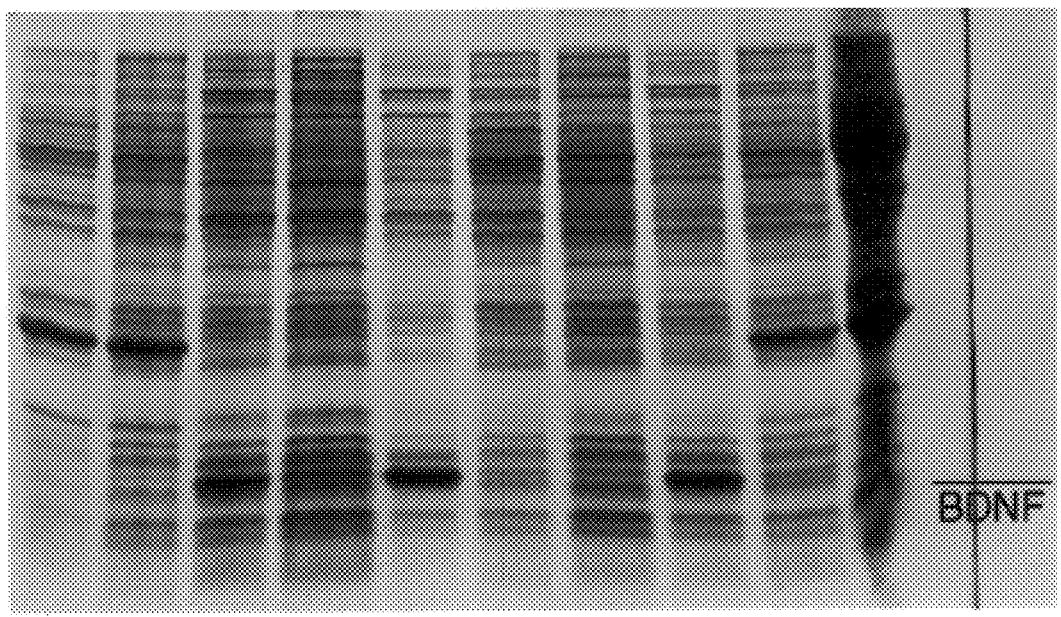
FIG. 10 is a picture of an SDS gel which compares the leakage and expression characteristics of the commercially available BL21(DE3) strain (lanes 3–5), the BL21(DE3) strain containing pLysS as a secondary vector (lanes 1–2), the EE11-20 strain (lanes 6–8), and the EE11-20 strain containing pLysS as a secondary vector (lanes 9–10). Comparisons were based on expression of BDNF as the target product gene. Lanes 1, 5, 6 and 10 represent overnight (ON) cultures, lanes 4 and 7 represent preinduction (preI) cultures, and lanes 2, 3, 8 and 9 represent induction (using IPTG at 28° C.) (I-28) cultures.
Figure 11:
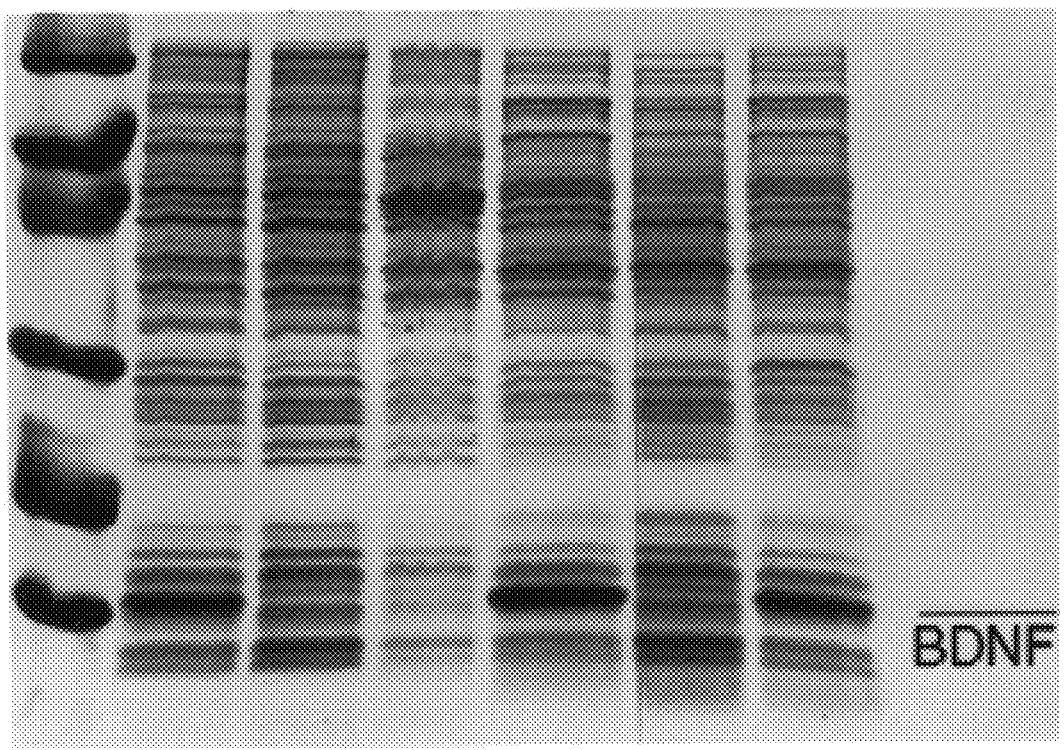
FIG. 11 is a picture of an SDS gel which compares the leakage and expression characteristics of the commercially available BL21(DE3) strain (lanes 5–7), and the EE11-11M strain (lanes 2–4). Comparisons were based on expression of BDNF as the target product gene. Lanes 4 and 5 represent overnight (ON) cultures, lanes 3 and 7 represent preinduction (preI) cultures, and lanes 2 and 6 represent induction (using IPTG at 28° C.)(I-28) cultures. Lane 1 is the low range Biorad molecular weight marker.
Figure 12:
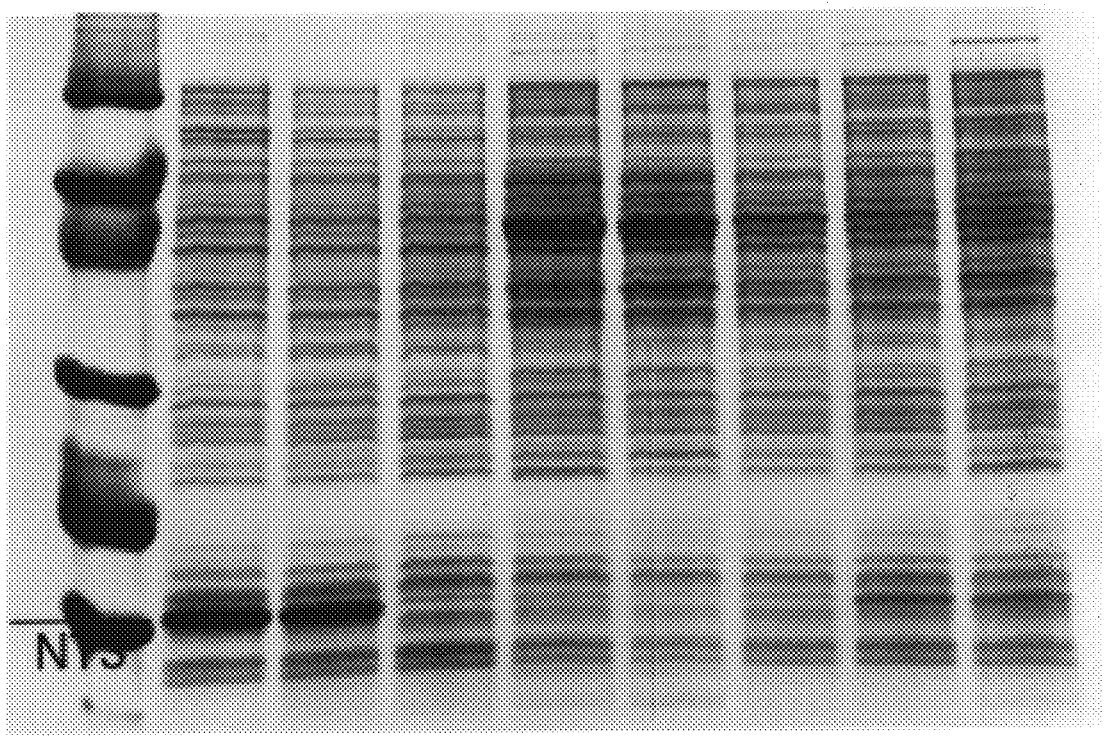
FIG. 12 is a picture of an SDS gel which shows the leakage and expression characteristics of the EE11-11M strain using expression of NT-3 as the target product gene. Lane 5 represents overnight (ON) culture, lane 4 represents preinduction (preI) cultures, and lanes 2 and 3 represent induction using IPTG at 28° C. (I-28) or IPTG at 37° C. (I-37) cultures. Lane 1 is the low range Biorad molecular weight marker.

As depicted in FIG. 8, which uses NT-3 as the target gene, the EE11-20 strain has no detectable leakage in either the overnight culture (ON) or prior to induction (preI), while BL21(DE3) clearly does. Induction levels for NT-3 are comparable between strains. Looking at FIG. 9, which uses BDNF as a target gene, EE11-20 again displays no product leakage prior to induction, although BL21(DE3) clearly does. EE11-20 does have reduced levels of BDNF in pET22b than does BL21(DE3). Looking at FIG. 10, levels of BDNF expressed using the pAMG25 vector were similar for EE11-20 and BL21(DE3). For each of the experiments depicted in FIGS. 8–10, the presence of pLysS reduced leakage, but also inhibited product expression (as had been previously reported in the literature). Finally, looking at FIGS. 11 and 12, it is shown that EE11-11M does not display overnight or preinduction leakage but does produce comparable levels of protein as compared to BL21(DE3). Moreover, the EE11-11M strain is superior to the EE11-20 strain in that the presence of lac i on the vector has no effect on protein accumulation, and in fact, may yield higher levels of some products (e.g. compare FIGS. 8 and 12).

It's clear from these results, that additional elements which have been introduced to control leakage in the commercially available strains are not necessary in the strains developed in the present invention, and the strain of the present invention display both greater control of leakage and comparable levels of product expression upon induction.

EXAMPLE 6

Figure 13:
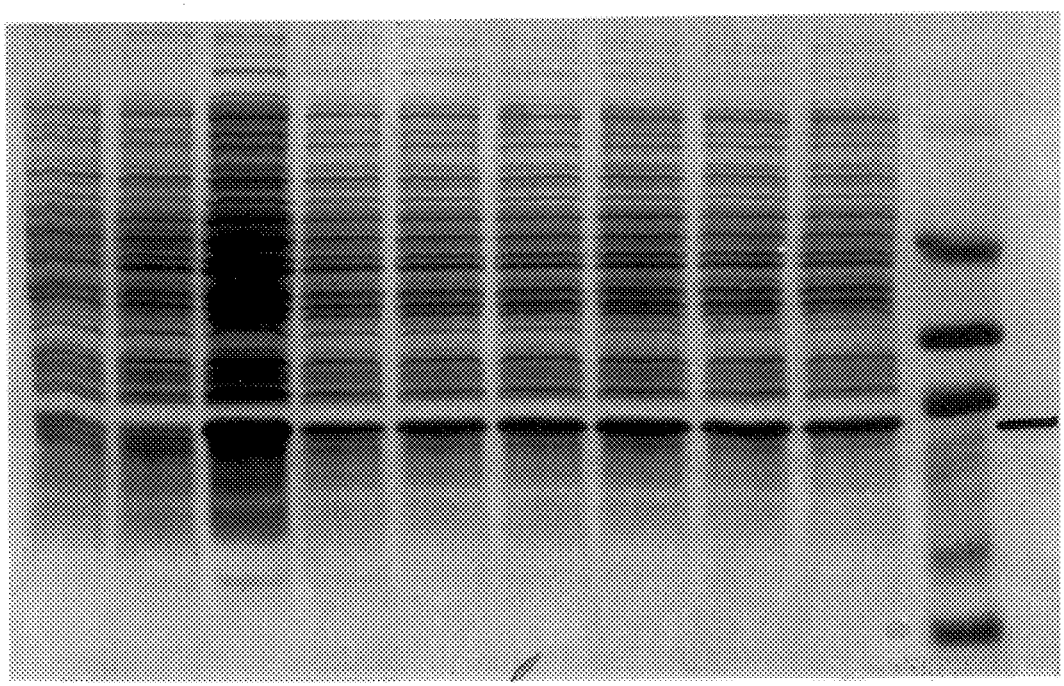
FIG. 13 is a picture of an SDS gel which shows a 10 liter fermentation induction time course of GCSF in pAMG25 in strain EE11-11M. Lane 1 is the culture at the time of induction. Lane 2 is the culture at the time of induction. Lanes 3–9 are the culture after additional hours of growth in the presence of inducer (IPTG), e.g., lane 3 is after 1 hour, lane 4 is after 2 hours, etc. Lane 10 is Amersham low molecular weight rainbow markers. The last lane is a GCSF marker.

To determine the impact that the presence of the MS2 coat protein may have on expression of a heterologous protein in high density fermentation several products were tested. Initially, the conditions reflected the conditions that were used for small scale shake flask, a low optical density induction. An exponential culture (optical density=1.4) of EE11-11M containing GCSF in pAMG25 was used to inoculate a 10 liter fermentor. This was grown at 28° C. to an optical density 0.8 and induced with the addition of IPTG. The culture was allowed to grow an additional 10 hours after induction reaching a final optical density of 12 and samples were taken every hour. As depicted in FIG. 13, there is no detectable preinduction leakage of the GCSF (lane 1) and the protein continues to be produced throughout the induction.

Figure 14:
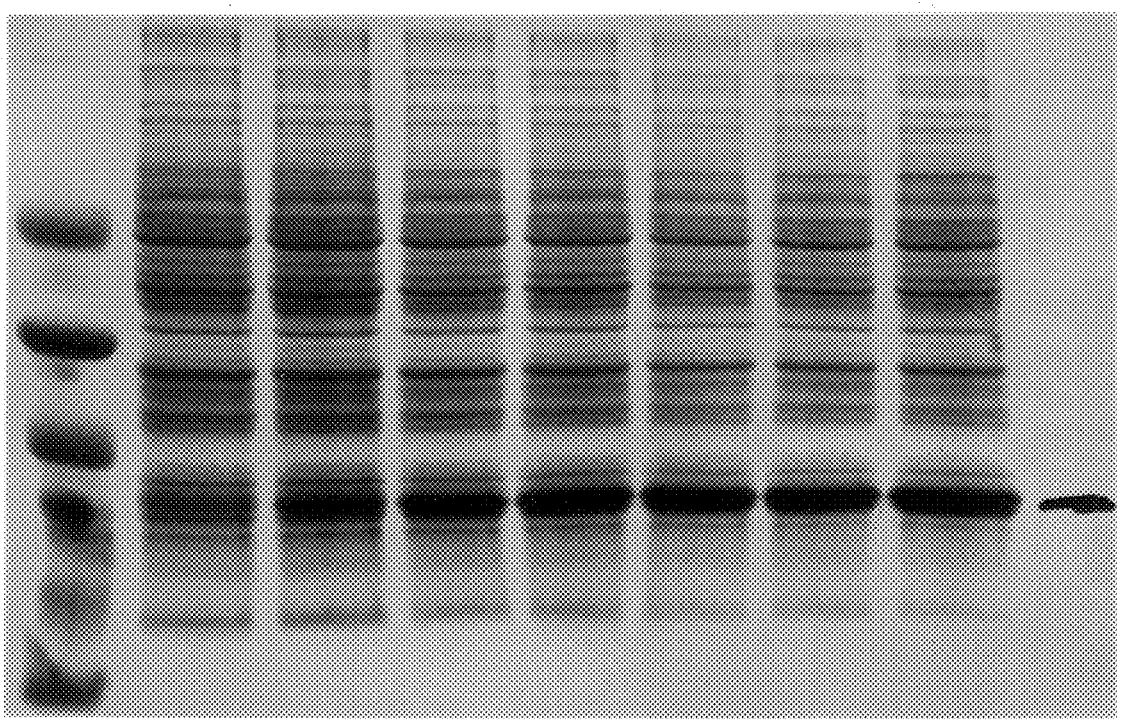
FIG. 14 is a picture of an SDS gel which shows a 10 liter fermentation induction time course of leptin in pAMG25 in strain EE11-11M. Lane 1 is Amersham low molecular weight rainbow markers. Lane 2 is the culture at the time of induction. Lanes 3–8 are the culture after additional hours of growth in the presence of inducer (IPTG), e.g., lane 3 is after 1 hour, lane 4 is after 2 hours, etc. Lane 9 is a leptin marker.

A second fermentation was done (using leptin in pAMG25) to test the EE11-11M strain performance at high density. An exponential inoculum (optical density=1.32) was used to start a 10 liter fermentation. This was grown to an optical density of 10 at 28° C. The culture was then induced by the addition of IPTG. Growth was continued for 6 hours and the culture reached a final optical density of 41. As depicted in FIG. 14, there is no apparent leakage prior to induction and leptin is produced well throughout the time of induction.

These experiments show that the presence of the MS2 coat protein has no negative impact on large scale or high density fermentation.

EXAMPLE 7

This example describes the use of the MS2 system to clone various T7 early genes. The T7 genes are cloned alone and as an operon.

The 0.4 and 0.6 early genes of bacteriophage T7 were PCR amplified using T7 356-DNA; Studier et al., *J. Mol. Biol.*, 135:917–937 (1979); Dunn & Studier, *J. Mol. Biol.*, 166:477–535 (1983) as a template. Each gene was PCR constructed to have an EcoRI site adjacent to the first codon of the gene (oligonucleotides 1049–5 and 1049–7)(See Table 1), and were cloned into pAMG13 which had been modified to contain an MS2 coat protein recognition site and a polyhistidine tag in frame with the multiple cloning region (oligonucleotides 1035–30 and 1035–31)(See Table 1). Oligonucleotides 1482–18 and 1266–69 (See Table 1) were used for the 0.4 gene and oligonucleotides 1266–71 and 1443–41 (See Table 1) for the 0.6 gene.

The MS2 coat protein was provided in trans from pRIN10. Electrocompetent cells containing pRIN10 were transformed by the early gene ligations with pAMG13. Positive clones were identified by PCR screening transformant colonies. Positive cultures were grown overnight as starters for expression experiments. Fresh tubes of LB Kan/Cam were inoculated at 1:100 dilution (50 $\mu l$ to 5 ml) and grown at 28° C. with shaking to an O.D. of approximately 0.7. These were induced by shifting to a 42° C. shaker and incubation was continued for 4 hours. Aliquots of 1 ml were removed and the cells were pelleted. Pellets were resuspended in cracking buffer at 0.01 OD unit/$\mu l$ and oiled for 5 minutes. These were cooled on ice and a 6 $\mu l$ aliquot of each was run on a 10–27% SDS polyacrylamide gel.

Figure 15:
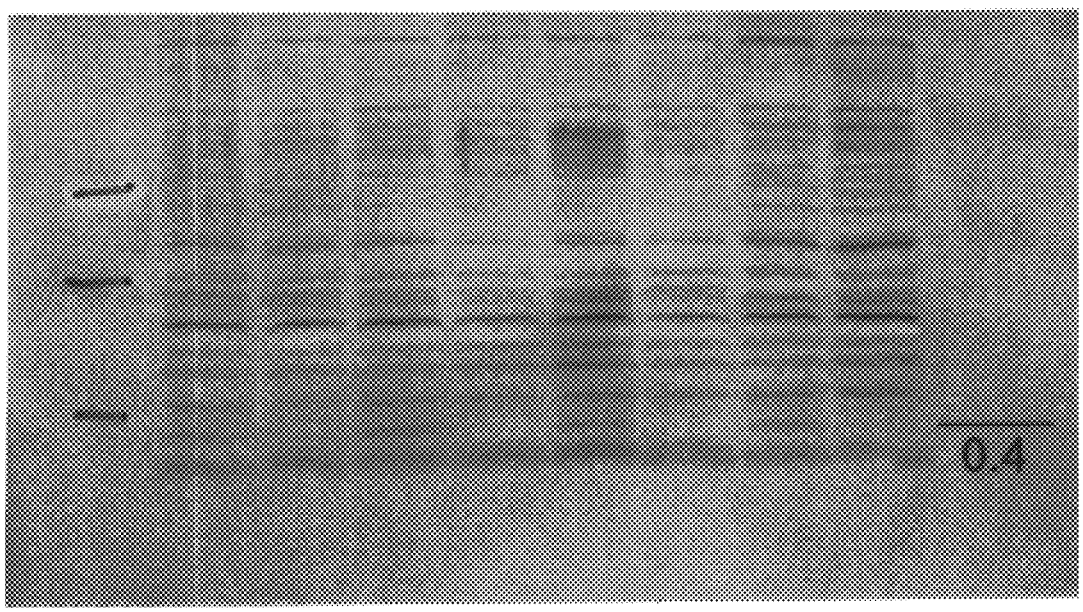
FIG. 15 is a photograph of a western blot showing the results of an expression experiment carried out using an MS2 based system into which the 0.4 early gene of T7 had been cloned. Lanes 2, 4, 6 and 8 represent four different 0.4 containing cultures after 4 hours of induction at 42° C.; Lanes 3, 5, 7 and 9 are the uninduced samples of the same cultures. Lane 1 is the low range Biorad molecular weight marker.
Figure 16:
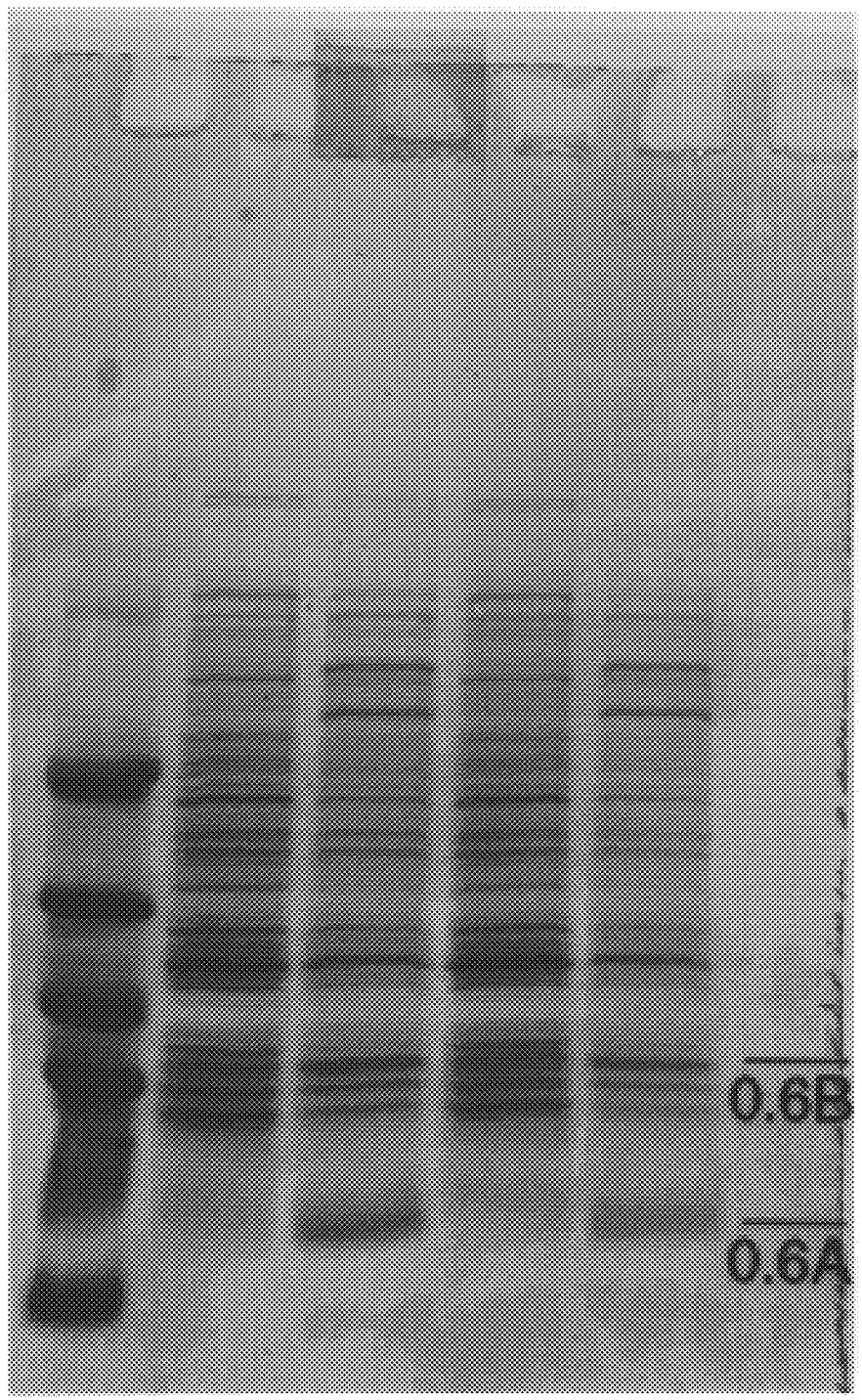
FIG. 16 is a photograph of an SDS gel showing the results of an expression experiment carried out using an MS2 based system into which the 0.6 early gene of T7 had been cloned. Lanes 2 and 4 represent two different 0.6 containing cultures uninduced; Lanes 3 and 5 are the same samples after 4 hours of induction at 42° C. Lane 1 is the low range Biorad molecular weight marker.

Protein was then electrophoretically transferred to nitrocellulose. The blots were blocked overnight in blotto-tween with 2% non-fat dry milk. The blots were probed for 1 hour with a rabbit derived polyclonal antibody to synthetic peptide based on expected protein sequence. This sera was diluted 1 to 2000. After washing the blots were probed with donkey anti-rabbit horse radish peroxidase conjugated antibody (Amersham) for 1 hour. This was washed and treated with ECL reagents (Amersham) and exposed to X-ray film. The exposure was for 4 minutes. The film was developed using a Kodak film processor. As depicted in FIG. 15, expression of the 0.4 gene was obtained using the MS2 controlled system. Likewise, the expression of the 0.6 gene was obtained (FIG. 16).

Two versions of the 0.7 gene were constructed: 1) oligonucleotides 1053–66 and 1266–73 (See Table 1) were used to construct the full-length version of the gene; and 2) oligonucleotides 1053–66 and 1266–72 (See Table 1) were used to construct a truncated version of the gene. The truncation was based on a mutant version that had been isolated while trying to clone the full-length version without an MS2 site in a single copy vector, and has an ochre mutation at codon 242. This early stop is similar to a mutation isolated from the phage in codon 243; Studier, F. W., *J. Mol. Biol.*, 79:227–236 (1973), and that mutant was shown to have lost host shut-off activity but retained kinase activity; Michalewicz and Nicholson, *Virology*, 186:452–462 (1992).

An operon of the early genes was also constructed by sequential PCR. Oligonucleotides 1511–32, 1539–60, 1803–86, 1319–59, 1577–83, 1577–84, 1539–65, 1066–72 and 1435–93 (See Table 1) were designed to have sequence overlapping the adjacent genes to each individual early gene and also to introduce an MS2 site adjacent to the start site of each coding region. Each gene was PCR amplified individually using these oligonucleotides. The early genes were then added together sequentially. The 0.4 and 0.5 genes were first linked by using both as template and only using the outside primers. This yielded a 0.4–0.5 fragment which was then used as a half template with the 0.3 fragment and so on until a complete 0.3 to 0.7 construct, named 3-7t operon, was generated (SEQ ID NO:2)(FIG. 17). To further reduce the leakage of the early genes in the operon the "downstream box" sequences were mutated in the 0.3, 0.6 and 0.7 genes. Most of the base changes made to reduce "downstream box" homology were silent though one conservative amino acid substitution did occur in each of the genes.

EXAMPLE 8

This example describes the results of experiments wherein the 3-7t operon constructed and described in Example 7 was used to enhance the expression of heterologous proteins in *E. coli*. The expression characteristics of the following systems were compared: 1) NDF alpha/beta cloned in pAMG33, and expressed in *E. coli* GM221, or with 3-7t operon in pRIN10 expressed in *E. coli* GM221; 2) 301–941 TP2 cloned in pAMG22 and expressed in *E. coli* GM221 or with 3-7t operon in pRIN10 and expressed in *E. coli* GM221.

For each experiment, single colonies were picked from plates and grown up in two 5 ml portions of LB with Kanamycinor LB with Kanamycin and Chloramphenicol. The tubes shook overnight at 28° C. Four liter flasks containing 1 L of 2XYT with Kanamycin or 2XYT with Kanamycin and Chloraphenicol were set up. These were inoculated with the 10 mls of starter culture. These were grown with shaking at 28° C. to an O.D. of 0.8. The cultures were then shifted to 37° C. with shaking for 1 hour. They were then shifted back to 28° C. and taken to 0.4 mM with IPTG. These were grown for an additional 3 hours with samples removed each hour. The 1 ml samples were centrifuged for 5 minutes at 15K and 4° C. The supernatant was decanted and the pellet was frozen. 500 µl of each culture was diluted into 500 µl of 2XYT and the optical density was taken. Pellets were then thawed and resuspended in 0.01 OD unit/µl cracking buffer. 6 µl of these cracked pellets were then loaded onto an SDS polyacrylamide gel (4–20%). After running at 150V for 1.3 hours, the gels were stained with coomassie blue to visualize the proteins.

Figure 18:
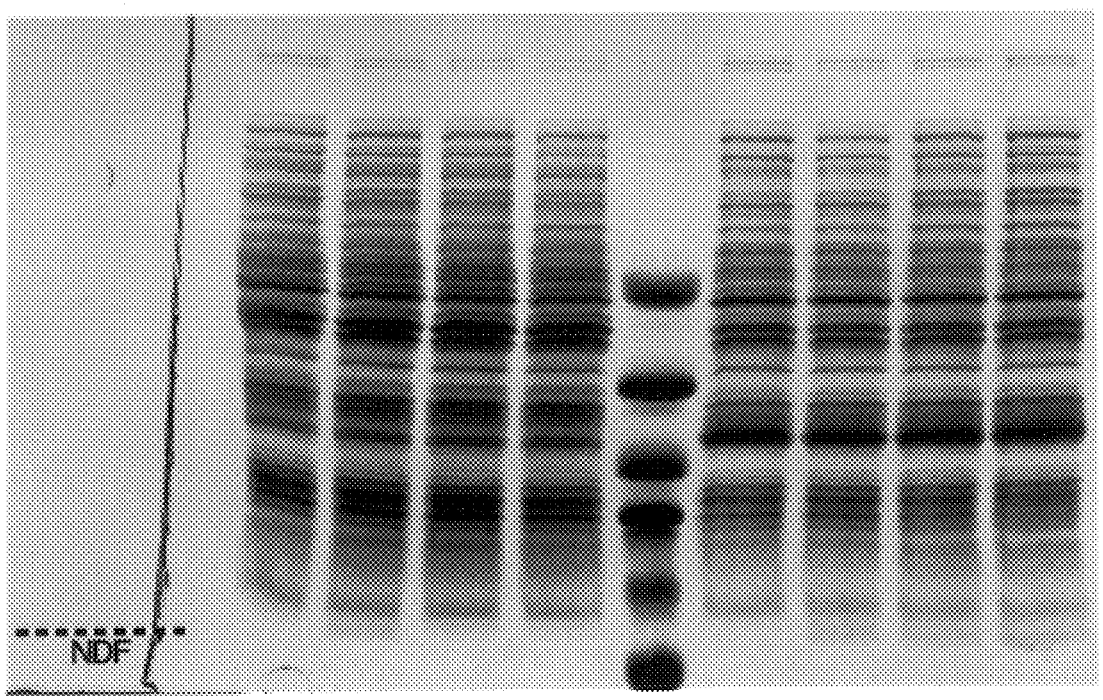
FIG. 18 is a picture of an SDS gel which compares the expression of NDF alpha/beta in the absence and presence of the T7 early proteins. The 3-7t operon was in pRIN 10 and was induced by a shift in temperature from 28° C. to 37° C. NDF alpha/beta was in plasmid pAMG33 and is induced by the addition of IPTG when the temperature is shifted back to 28° C. The left half of the gel is a time course of NDF alpha/beta in the absence of the T7 early genes. Lane 1 is after induction of the early proteins but prior to induction of NDF alpha/beta. Lanes 2–4 are the culture after additional hours of growth in the presence of inducer (IPTG), e.g., lane 2 is after 1 hour, lane 3 is after 2 hours, etc. Lane 5 is Amersham low molecular weight rainbow markers. The right half of the gel is a time course of NDF alpha/beta expression in the presence of the T7 early proteins. Lane 6 is after induction of the early proteins but prior to induction of NDF alpha/beta. Lanes 7–9 are the culture after an additional hour of growth in the presence of inducer (IPTG).

As shown in FIG. 18 the presence of the T7 early proteins protects NDF alpha/beta from proteolysis. When there are no T7 early proteins present, NDF alpha/beta is produced by 1 hour of induction (lane 2) but is no longer detectable by 2 hours of induction (lane 3). When the T7 early proteins are present, there is more NDF alpha/beta detectable and it continues to accumulate throughout the 3 hours of the induction (lanes 7–9).

Figure 19:
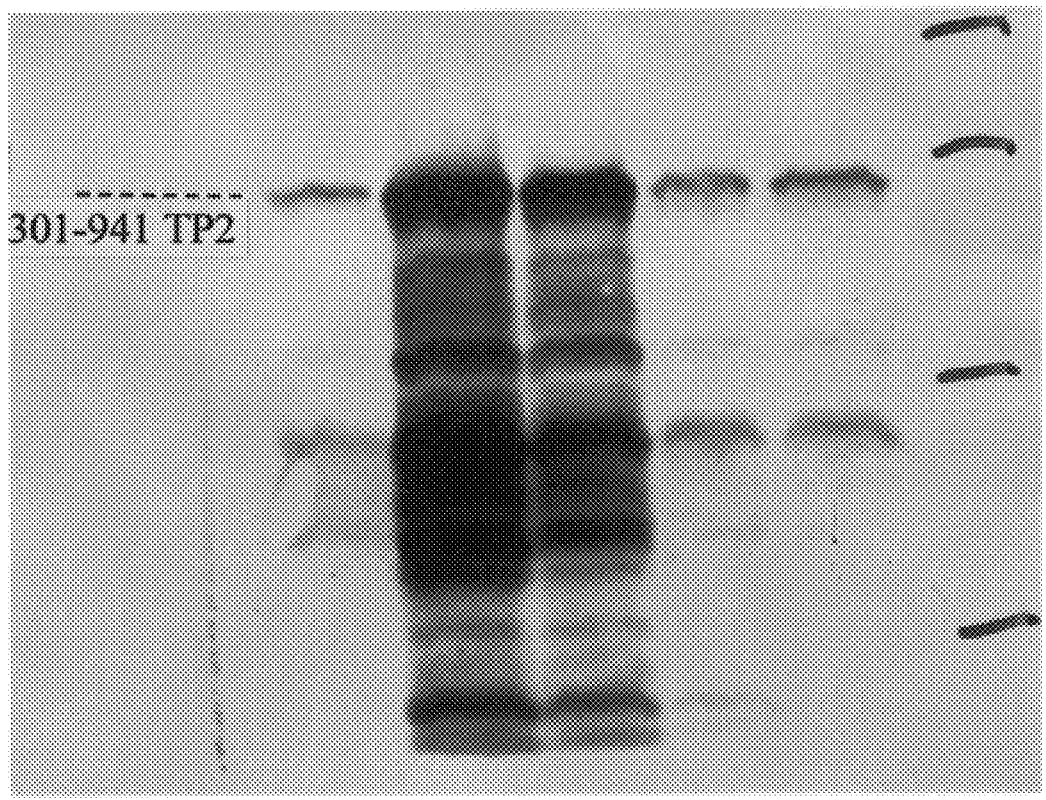
FIG. 19 is a picture of a western blot of a gel comparing the expression of a truncated version of human telomerase subunit TP2 (301–941 TP2) in the presence and absence of T7 early proteins. The 3-7t operon was in pRIN10 and was induced by a shift in temperature from 28° C. to 37° C. 301–941 TP2 was in plasmid pAMG22 and is induced by the addition of IPTG when the temperature is shifted back to 28° C. Lane 1 is a preinduction sample from 301–941 TP2 in the presence of the T7 early proteins. Lane 2 is the expression of 301–941 TP2 after 2 hours of induction in the presence of T7 early proteins at 28° C. Lane 3 is the expression of 301–941 TP2 after 2 hours of induction in the presence of T7 early proteins at 37° C. Lane 4 lane is a preinduction sample from 301–941 TP2 in the absence of the T7 early proteins. Lane 5 is the expression of 301–941 TP2 after 2 hours of induction in the absence of T7 early proteins at 37° C.

As shown in FIG. 19 the host cell does not produce 301–941 TP2 after induction in the absence of the T7 early proteins (lane 5). When the T7 early proteins are present production of the protein after induction increases dramatically (lanes 2 and 3).

EXAMPLE 9

This example describes the construction and testing of a series of prokaryotic host strains that have been engineered to produce different concentrations of MS2CP. The host strains have the MS2CP linked to a modified TET promoter inserted into their chromosome.

Construction of strains A cassette of the MS2CP-14 variant linked to the TET promoter was constructed using oligonucleotides 1674–96 and 1674–97 (See Table 1). This cassette was cloned into the NotI and BamHI sites of MMebg to generate MMebg-MS2CP-14. The TET promoter was then optimized in stages: 1) the −10 region was taken to consensus by overlapping PCR. The mutant halves were constructed using oligonucleotides 1011–96 with 1784–89 and 1758–66 with 1674–97. The halves were then PCRed together using oligonucleotides 1674–96 and 1674–97. This was then recloned into MMebg from NotI to BamHI to yield MMebg-MS2CP14 (−10); 2) the −35 region was brought to consensus to produce a fully optimized TET promoter. This was again done using half reaction PCR where MMebg-MS2CP14 (−10) served as template. Mutant halves were constructed using oligonucleotide pairs 1011–96 with 1784–88 and 1803–15 with 1674–97 (See Table 1). The two halves were then PCRed together using oligonucleotides 1674–96 and 1674–97. This was recloned into MMebg from NotI to BamHI to yield MMebg-MS2CP14 (fully optimized). MMebg-MS2CP14 (−10) and MMebg-MS2CP14 (fully optimized) both displayed increased production of MS2 coat protein over the wild type promoter construct (small increase for the (−10) and a very large increase for the fully optimized).

To construct mutant promoter versions that would deliver levels of MS2 coat protein intermediate to the previously described mutants a strategy for randomizing the sequence of the ribosome binding site (RBS) was employed. The sequence of the promoter region containing the −10 consensus change and MS2 coat protein gene up to the KpnI site were used to design oligonucleotides 1822–01, 1822–02 and 1863–81. These oligonucleotides were phosphorylated and annealed with oligonucleotides 1821–99, 1822–03, 1822–04 and 1822–05. The product of ligation then served as a PCR template using oligonucleotides 1822–06 and 1822–07. This fragment which is now randomized in the ribosome binding sequence was able be ligated from NotI to BamHI.

To determine the effect of the ribosome binding site changes on protein production, a beta galactosidase assay was employed. Specifically, a MS2CP-14-LacZ fusion was constructed by producing a LacZ fragment with oligonucleotides 1803–52 and 1803–53 and ligating this into MMebg-MS2CP-14 from KpnI to BamHI. This construct contains the wild type TET promoter linked to the beginning of the MS2 coat protein gene which is fused in frame with the beta galactosidase gene LacZ. The randomized RBS fragments described in the previous paragraph were then ligated into this construct from NotI to KpnI. The initial fusion and the randomized fusion ligations were integrated into the chromosome following the protocol described in Example 5. The host strain used was F'tet/393AlacZ145N which is deficient in beta galactosidase activity. Resolved lysogens were assayed for beta galatosidase activity as described; Miller, *Experiments in molecular genetics*, Cold Spring Harbor Laboratory Press, pgs.352–355 (1972). A series of mutants with varying levels of activity were identified. Three of these mutants, numbers 1, 3 and 15 were selected for the production of strains. The MMebg-MS2CP-14-LacZ that had given rise to these particular strains were digested KpnI to BamHI to remove the LacZ fusion. The MS2CP-14 gene was then regenerated by ligation of the KpnI to BamHI fragment into these vectors. Strains were constructed from these three mutants and the MMebg-MS2CP-14 (fully optimized) by integration into host strain 393. The resultant strains were named GM315 (mutant 1), GM320 (mutant 3), GM340 (mutant 15) and GM350 (fully optimized).

Figure 20:
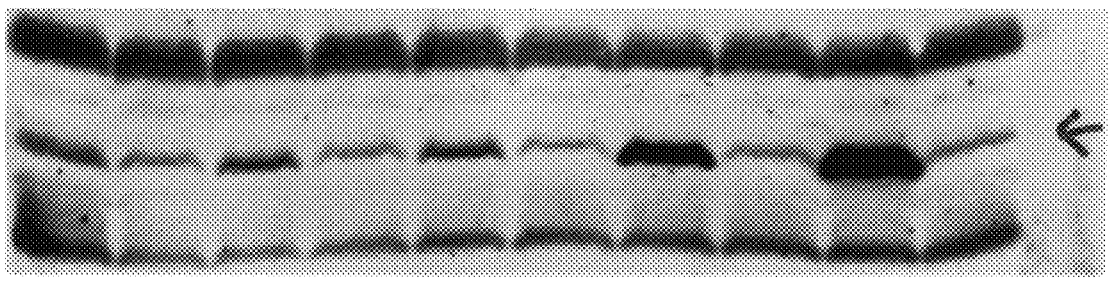
FIG. 20 is a picture of a western blot of a gel showing the passive production of varying levels of MS2 coat protein by strains GM315, GM320, GM340 and GM350. The strains are compared against the parent strain from which they were constructed. Lane 1 represents a log phase culture of GM315. Lanes 2, 4, 6, 8 and 10 are parent strain 393. Lanes 3 and 5 are GM320, lane 7 is GM340, and lane 9 is GM350.

Testing of strains to produce MS2CP The ability of these strains to produce MS2 coat protein was determined by western analysis of exponential cultures. Colonies of each strain were picked from plates and used to inoculate 5 mls of LB. These were grown with shaking at 30° C. to an optical density of 0.7. One ml samples were taken. All samples were pelleted by centrifugation and the pellets were resuspended in cracking buffer. After boiling for 5 minutes, a 6 $\mu$l aliquot of each was run on a 4–20% SDS polyacrylamide gel (Novex). Protein was then electrophoretically transferred to nitrocellulose. The blots were blocked overnight in blotto-tween with 2% non-fat dry milk; Harlow & Lane, *Immunoblotting in Antibodies, A Laboratory Manual*, Chapter 12, Cold Spring Harbor Laboratory Press, (1988). The blots were probed for 1 hour with a rabbit derived polyclonal antibody to MS2 coat protein. After washing the blots were probed with donkey anti-rabbit horse radish peroxidase conjugated antibody (Amersham) for 1 hour. This was washed and treated with ECL reagents (Amersham) and exposed to X-ray film. The film was developed using a Kodak film processor. As shown in FIG. 20, the level of MS2 coat protein passively expressed during log phase growth is detectable over background at low levels in GM315 and GM320 and increases considerably in GM340 and GM350.

Cloning heterologous genes using the strains Using conventional techniques, N-terminal his tag fusions of the ns5b gene of hepatitis C (the Hep C polymerase) were found to be very difficult to clone. When full-length versions of the gene were isolated they contained mutations that led to early stops of translation or that were in the ATG and prevented translational initiation altogether. To facilitate the cloning of this gene, an MS2 recognition sequence was linked to it, and the ligations used to first transform strain GM350. Full-length inserts were detected, sequenced, and determined to be correct.

The recombinant his-tagged ns5b gene obtained from GM350 was then placed in pAMG21 and used to transform GM221, GM315 and GM320 (GM221 does not contain MS2 coat protein while GM315 and GM320 produce lower levels than GM350). The gene was found to be stable in all three cell lines.

The ability of the various strains to produce the his-tagged hepC polymerase was then determined. Overnight cultures were used to inoculate 50 ml of 2XYT in 250 ml erlenmeyer flasks at a 1 to 100 dilution. These were grown with shaking at 30° C. to an optical density of 0.6. The pAMG21 vector contains a lux promoter and so the production of the hepC polymerase is accomplished by the addition of autoinducer at a final concentration of 30 ng/ml. Incubation is continued for 4 hours and samples are taken. Cells are pelleted by centrifugation. The pellets were resuspended in 10 ml PBS and this was microfluidized. The samples were centrifuged to separate the soluble and insoluble fractions. These were mixed with cracking buffer and samples were run on 4–20% SDS gels. After running at 150V for 1.3 hours the gels were stained with coomassie blue to visualize the proteins.

Figure 21:
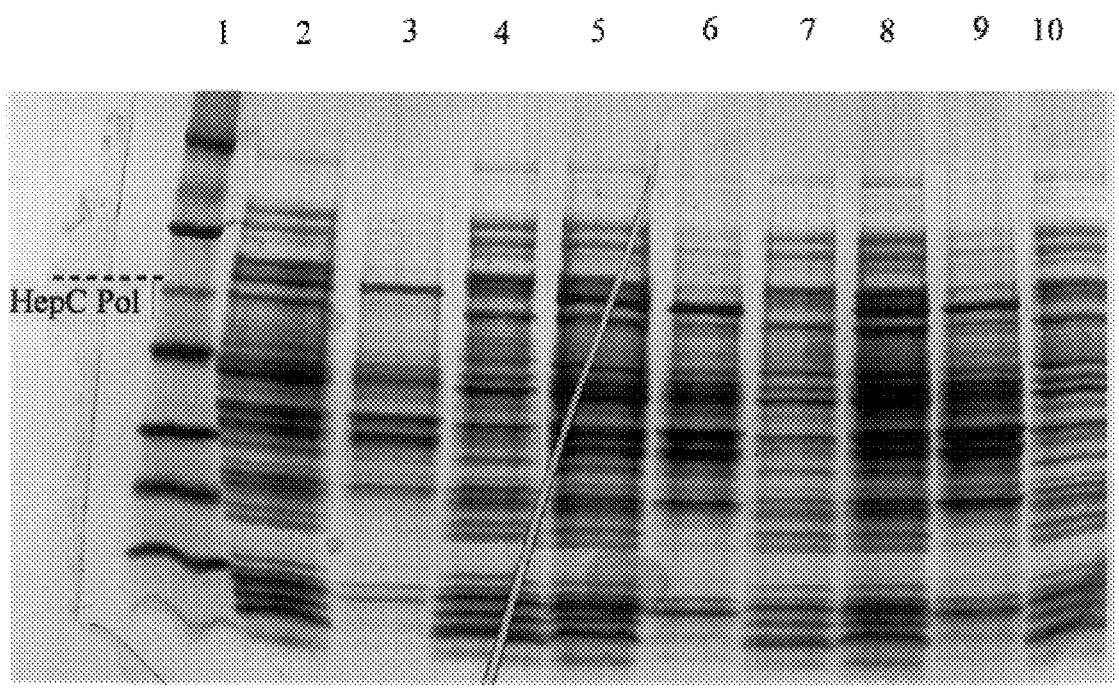
FIG. 21 is a picture of a gel showing the expression of the Hepatitis C polymerase (HepCpol) in strains having varying levels of MS2 coat protein (the soluble and insoluble fractions from each expression experiment are also compared). Lane 1 is molecular weight markers. Lane 2 is whole cell extract of an induced culture of HepCpol in pAMG21 expressed in strain GM221 which contains no MS2 coat protein. Lane 3 is the insoluble fraction from this experiment and lane 4 is the soluble fraction. Lane 5 is whole cell extract of an induced culture of HepCpol in pAMG21 expressed in strain GM315 which contains MS2 coat protein. Lane 6 is the insoluble fraction from this experiment and lane 7 is the soluble fraction. Lane 8 is whole cell extract of an induced culture of HepC in pAMG21 expressed in strain GM320 which contains more MS2 coat protein than that in GM315. Lane 9 is the insoluble fraction from this experiment and lane 10 is the soluble fraction.
Figure 24:
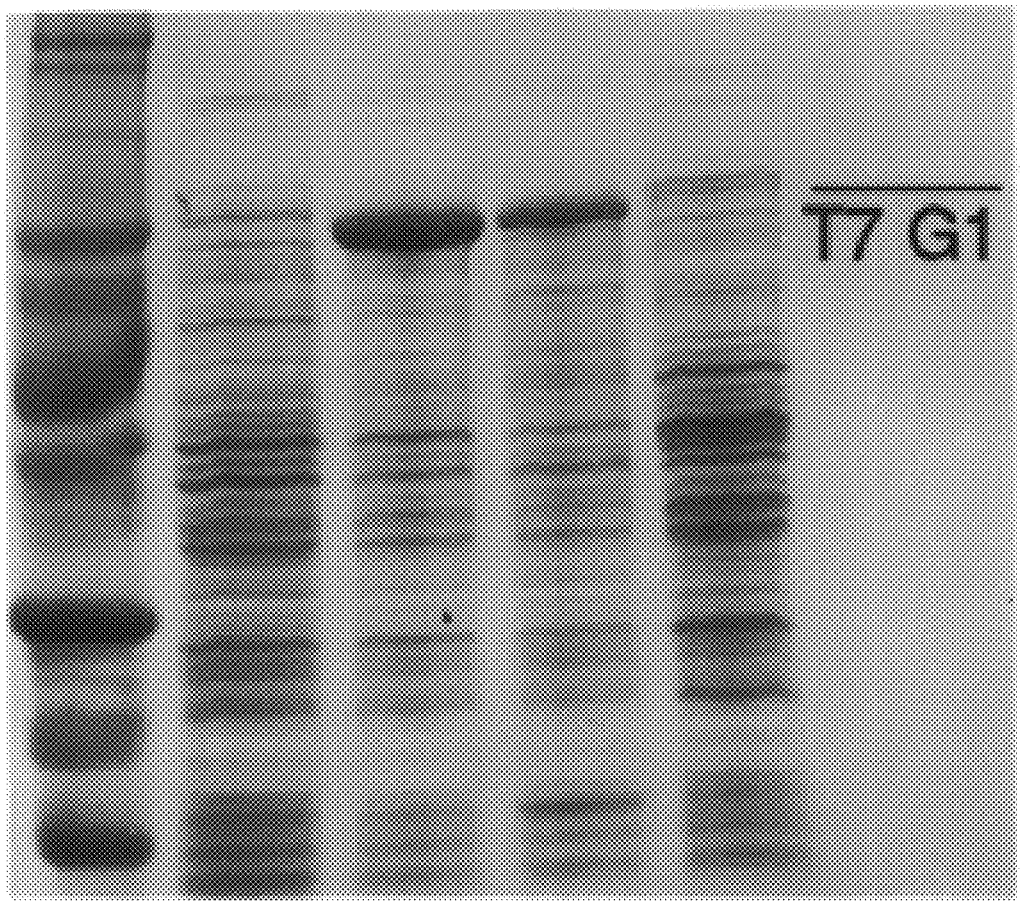
FIG. 24 is a picture of an SDS gel which shows the leakage and expression characteristics of pAMG13 using expression of T7 gene 1 (under the control of a lambda promoter) as the target product gene. Lane 5 represents a stationary sample which grew overnight at 28° C., lane 4 represents a sample which was induced for 4 hours at 42° C., lane 3 represents a sample which was induced for 4 hours at 37° C., lane 2 represents an uninduced sample which grew at 28° C. to an O.D. of 0.6, and lane 1 is the low range Biorad molecular weight marker.
Figure 25:
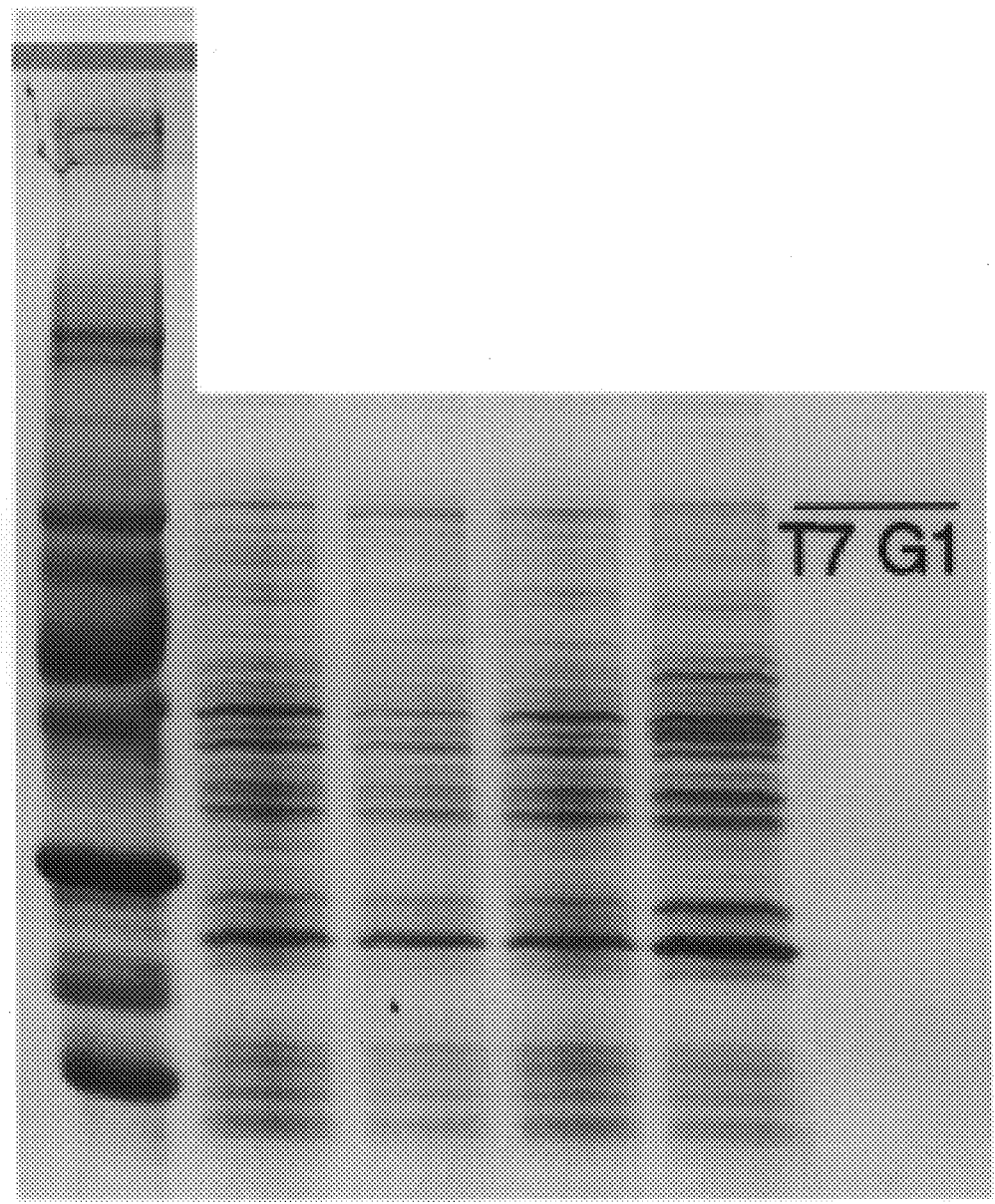
FIG. 25 is a picture of an SDS gel which shows the leakage and expression characteristics of pAMG13 in which T7 gene 1 was coexpressed with T4 operon pRIN10. Lane 4 represents a stationary sample which grew overnight at 28° C., lane 3 represents a sample which was induced for 4 hours at 42° C., lane 2 represents a sample which was induced for 4 hours at 37° C., and lane 1 represents an uninduced sample which grew at 28° C. to an O.D. of 0.6.

As depicted in FIG. 21, the hepC polymerase is produced in all three strains. The majority of the protein produced is insoluble. There may be somewhat higher expression in the MS2 coat protein containing strains. This example thus demonstrates a way in which these strains may be employed: the highest producer, GM350, is used to initially clone the unstable gene; and, once a stable clone is obtained and confirmed as correct, it may be transformed into the remaining strains and the ability to produce the protein product as well as the sustainable stability of the gene may be determined.

EXAMPLE 10

This example describes the construction of the pAMGuvxs plasmid vector, the pAMGX plasmid vector, and the T4 operon pRIN plasmid vectors used to develop the T4 middle promoter based system.

Bacteriophage T4 middle promoters were constructed synthetically using the published sequences of PuvsX and PX; Hinton, D. M., *J. Biol. Chem.*, 266(27):18034–18044 (1991)(uvsX: oligonucleotides 1084–66 and 1084–67 (See Table 1), X: oligonucleotides 1084–68 and 1084–69)(See Table 1). The PuvsX promoter was reconstructed to remove the NdeI site it contains (oligonucleotides 1202–11 and 1550–85)(See Table 1). Each construct was designed to have AatII and ClaI restriction sites. The complete base sequence of the PuvsX promoter construct is depicted in FIG. 22, and the complete gene sequence of the PX promoter construct is depicted in FIG. 23. The plasmid pAMG13 was digested with AatII and ClaI to remove the synthetic lambda promoter and the vector was gel purified. The T4 middle promoters were then each ligated with this plasmid to create plasmid vectors pAMGuvsX and pAMGX.

The motA/asiA operon was constructed such that each gene was preceded by an MS2 coat protein recognition sequence. The published sequence of motA; Uzan et al., *Mol. Microbiol.*, 4(9):1487–1496 (1990), and asiA; Orsini et al., *Jour. Bacteriology*, 175(1):85–93 (1993) were used for the construction. At the beginning of the fragment was an XbaI site and at the end was a XhoI site (oligonucleotides 1084–63, 1528–19, 1528–20, and 1703–53)(See Table 1). This fragment was digested with XbaI and XhoI and then ligated with several pRIN plasmid vectors to provide, for example, T4 operon pRIN10 plasmid vector, T4 operon pRIN11 plasmid vector, etc.

EXAMPLE 11

This example describes the testing of the pAMGuvxs, pAMGX and T4 operon pRIN plasmid vectors prepared and described in Example 10. Specifically, expression experiments were carried out to test the ability of the systems to prevent leakage and allow for expression of product gene. The expression and leakage characteristics of the following systems were compared: 1) T7 gene 1 cloned and expressed in *E. coli* host GM221 (ATCC Accession No. 202077) containing the pAMG13 vector (i.e., T7 gene 1 under the control of the lambda promoter); 2) T7 gene 1 cloned and coexpressed with T4 operon pRIN10 in *E. coli* host GM221 containing pAMG13; 3) T7 gene 1 cloned and coexpressed with T4 operon PRIN10 in *E. coli* host GM221 containing pAMGuvsX (i.e., T7 gene 1 under control of uvsX T4 middle promoter; 4) T7 gene 1 cloned and coexpressed with T4 operon pRIN11 in *E. coli* host GM221 containing pAMGuvsx; 5) NT-3 cloned and coexpressed with T4 operon pRIN10 in *E. coli* host GM225 containing pAMGuvsX; and 6) BDNF cloned and coexpressed with T4 operon pRIN10 in *E. coli* host GM225 containing pAMGuvsX.

For each experiment, single colonies were picked from plates and grown up in 5 ml 2XYT with Chloramphenicol and Kanamycin. The tubes shook overnight at 28° C. 50 ml tubes were set up with 5 ml 2XYT with Chloramphenicol and Kanamycin. The fresh tubes were inoculated with 50 µl of the starter cultures. These tubes were grown with shaking at 28° C. to an O.D. of 0.6–1.2. The PS4 promoter containing cultures (pRIN11) were induced with 20 µl IPTG, while the lambda promoter containing cultures (pAMG) were induced by shifting to either 37° C. or 42° C. Induction time for all of these expression experiments was 4.0 hours. 1 ml of each culture was centrifuged for 10 minutes. The supernatant was decanted and the pellet was frozen. 500 µl of each culture was diluted into 500 µl of 2XYT and the optical density was taken. Pellets were then thawed and resuspended in 0.01 OD unit/µl cracking buffer. 6 µl of these cracked pellets were then loaded onto an SDS polyacrylamide gel (4–20% or 16%). After running at 150V for 1.3 hours the gels were stained with coomassie blue to visualize the proteins.

Figure 26:
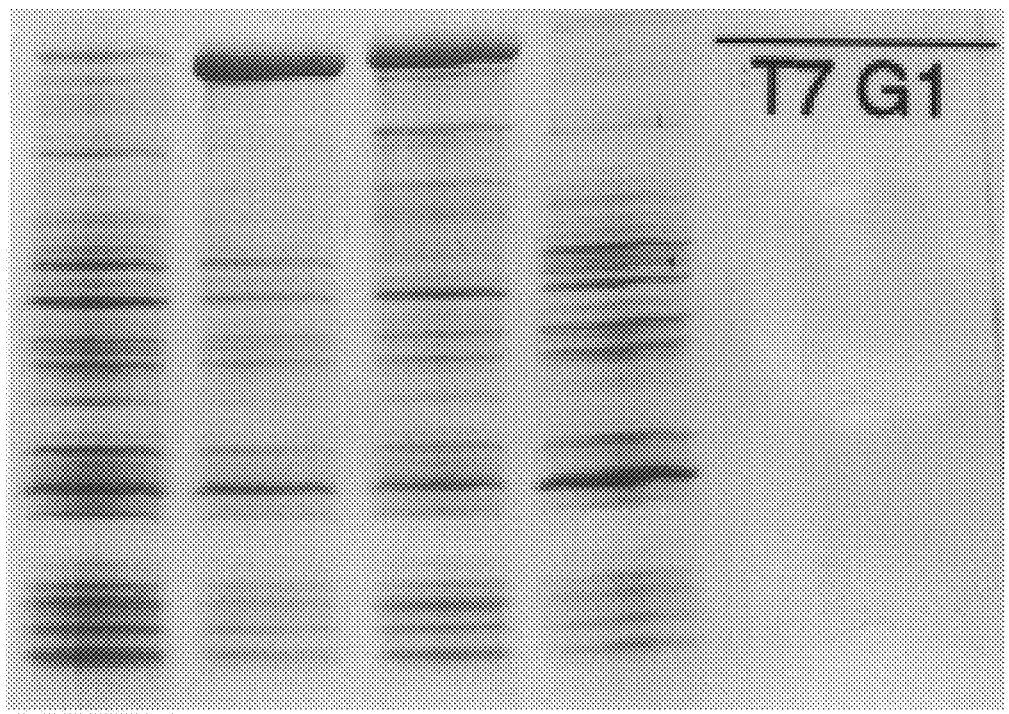
FIG. 26 is a picture of an SDS gel which shows the leakage and expression characteristics of pAMGuvsX in which T7 gene 1 (under the control of the uvsX T4 middle promoter) was coexpressed with T4 operon pRIN10. Lane 4 represents a stationary sample which grew overnight at 28° C., lane 3 represents a sample which was induced for 4 hours at 42° C., lane 2 represents a sample which was induced for 4 hours at 37° C., and lane 1 represents an uninduced sample which grew at 28° C. to an O.D. of 0.6.
Figure 27:
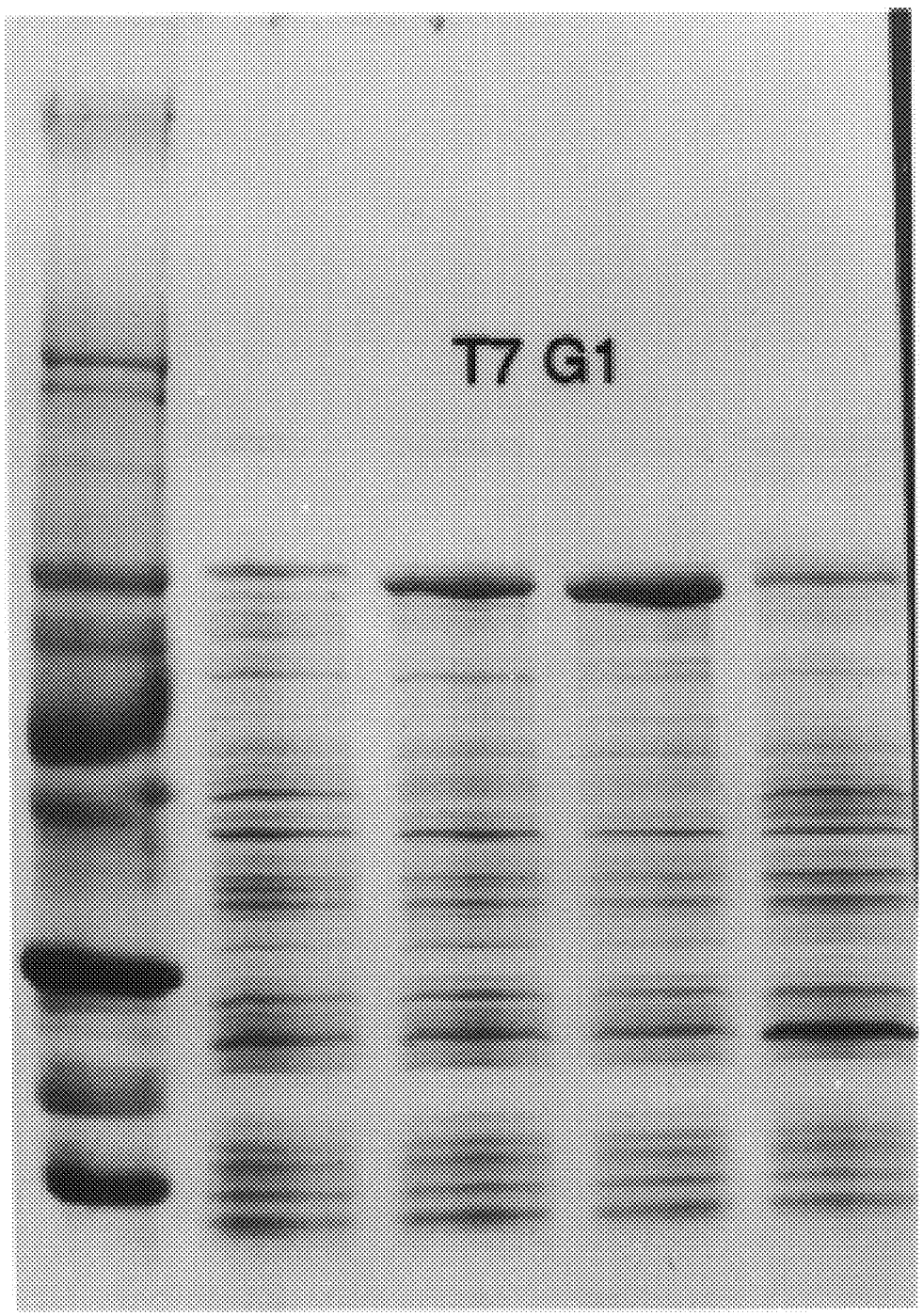
FIG. 27 is a picture of an SDS gel which shows the leakage and expression characteristics of pAMGuvsX in which T7 gene 1 was coexpressed with T4 operon pRIN11. Lane 5 represents a stationary sample which grew overnight at 28° C., lane 4 represents a sample which was induced for 4 hours at 37° C., lane 3 represents a sample which was induced for 4 hours at 28° C., lane 2 represents an uninduced sample which grew at 28° C. to an O.D. of 0.6, and lane 1 is the low range Biorad molecular weight marker.
Figure 28:
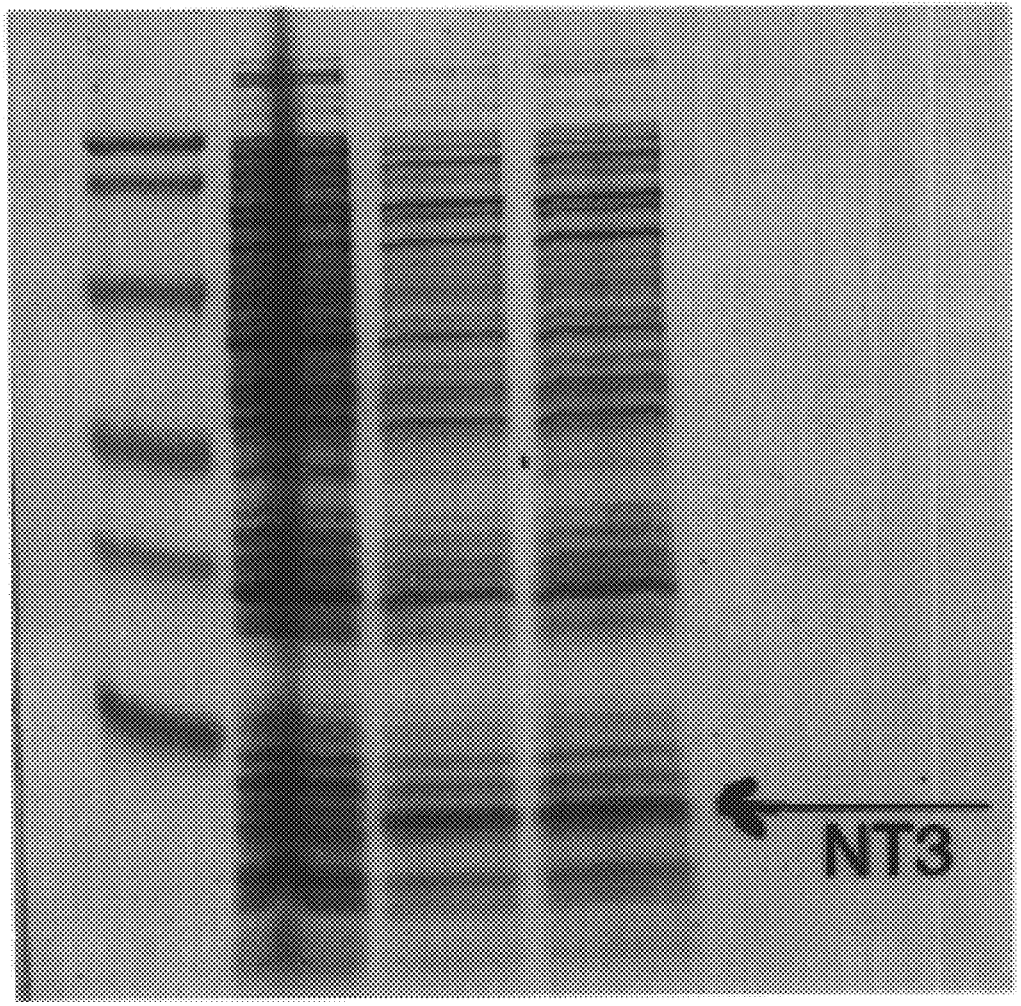
FIG. 28 is a picture of an SDS gel which shows the leakage and expression characteristics of pAMGuvsX in which NT-3 (under the control of the uvsX T4 middle promoter) was coexpressed with T4 operon pRIN10. Lane 4 represents a sample which was induced for 4 hours at 42° C., lane 3 represents a sample which was induced for 4 hours at 37° C., lane 2 represents an uninduced sample which grew at 28° C. to an O.D. of 0.6, and lane 1 is the low range Biorad molecular weight marker.

The data from FIGS. 24–29 can be summarized as follows: 1) the pAMG13 vector is capable, upon induction, to produce abundant levels of T7 RNA polymerase when the T7 gene 1 is under the control of the lambda promoter (see lanes 3 and 4, FIG. 24); 2) T4 operon protein products sufficiently abolish the recognition of the lambda promoter by the *E. coli* RNA polymerase (compare lanes 2 and 3 of FIG. 25 with lanes 3 and 4 of FIG. 24); 3) abundant levels of T7 RNA polymerase can be obtained in pAMGuvsX wherein T7 gene 1 is cloned and coexpressed with T4 operon pRIN10 (compare lanes 3 and 4 of FIG. 24 with lanes 2 and 3 of FIG. 26); 4) coexpression with T4 operon pRIN11 is as effective in producing T7 gene 1 as is T4 operon pRIN10 (compare lanes 3 and 4 of FIG. 27 with lanes 2 and 3 of FIG. 26); and 5) abundant levels of NT-3 and BDNF can also be obtained from pAMGuvsX wherein the NT-3/BDNF is cloned and coexpressed with T4 operon pRIN10 (compare FIGS. 28 and 29 with FIG. 26).

EXAMPLE 12

This example describes the cloning of the motA/asiA operon into single copy plasmids containing the MS2 system.

Figure 30:
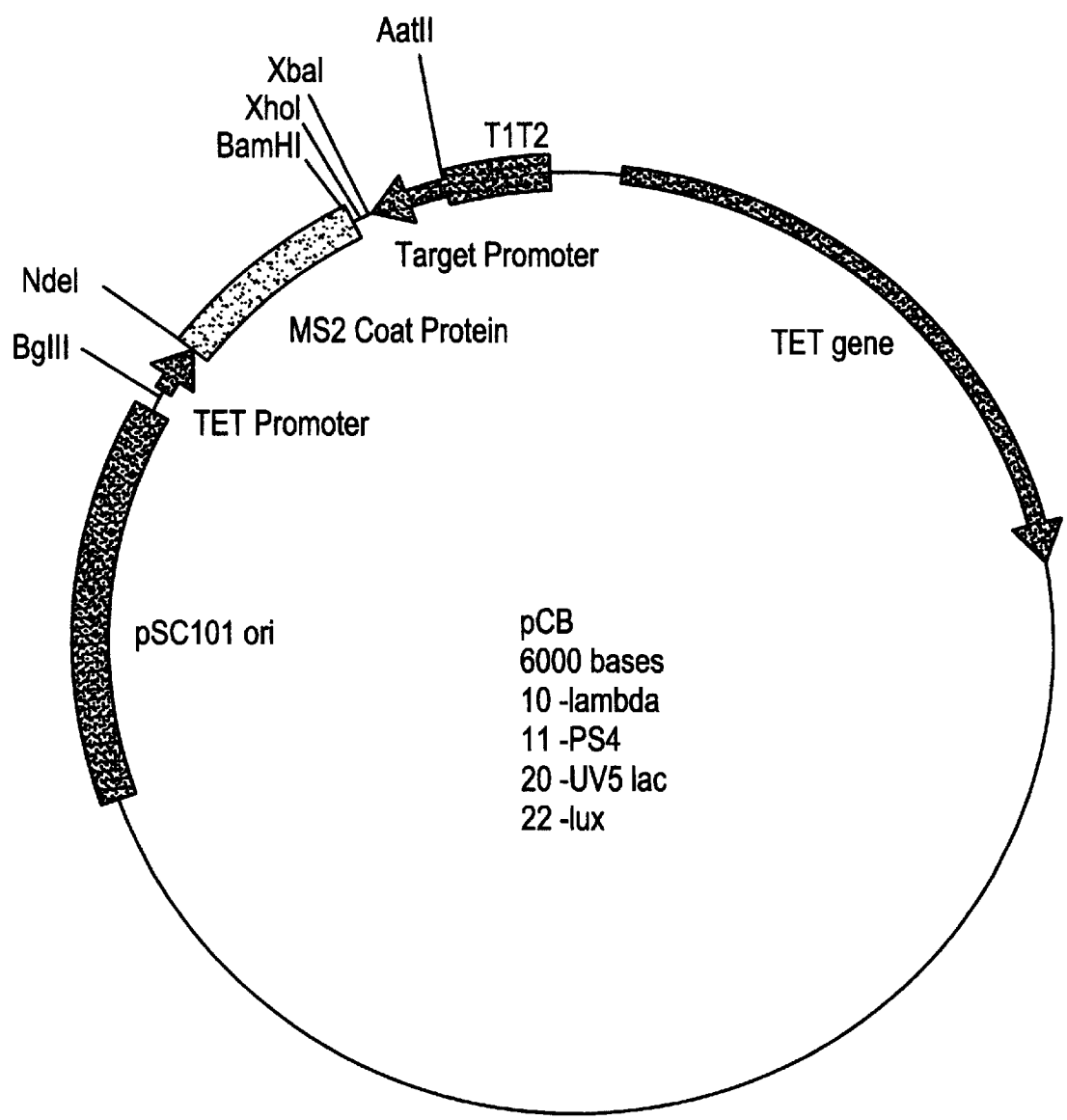
FIG. 30 is a schematic diagram of the pCB plasmid vectors developed in the present invention.
Figure 31:
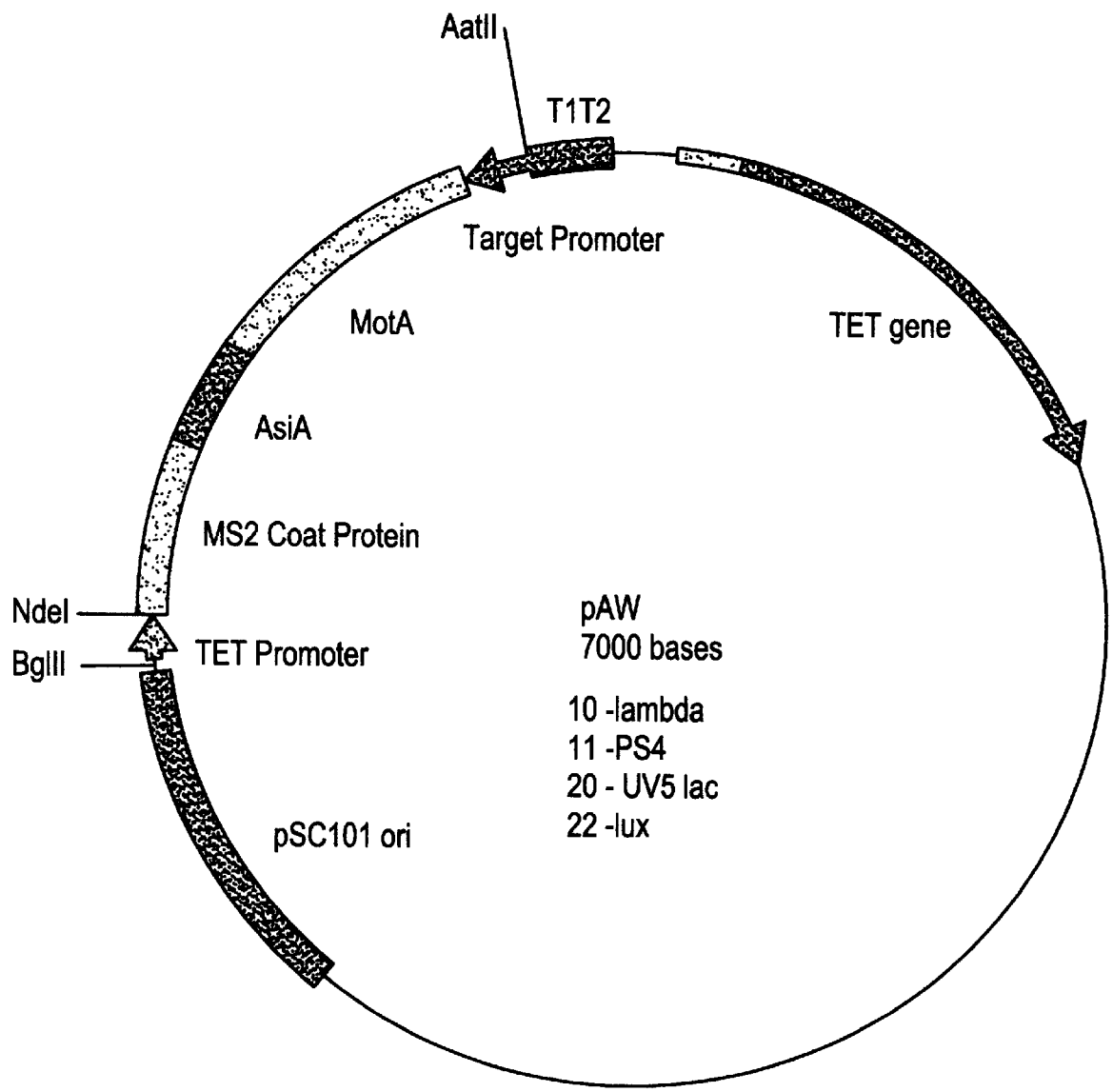
FIG. 31 is a schematic diagram of the pAW plasmid vectors developed in the present invention.

Single copy vectors were derived from pSC101; Bernardi and Bernardi, *Nuc. Acids Res.*, 12:9415–9426. This vector was digested with NdeI and then recircularized to yield plasmid pSC101dNde. A DNA linker containing BglII and NsiI sites was introduced into the EcoRI site of this plasmid. A fragment of pAMG22 from NsiI to BglII which contains the T1T2, PS4 promoter and the multiple cloning site was then cloned in to create plasmid pTS2. pTS2 was then cut with MluI and XmnI, the ends were blunted using Klenow fragment; Sambrook et al., *Molecular cloning, a laboratory manual*, Second edition, Cold Spring Harbor Laboratory Press, pgs. 5.40–5.41 (1989), and the plasmid was recircularized to yield pTS2d. Fragments of the pRIN plasmid vectors containing the target promoter, MS2 recognition site, MS2CP gene and TET promoter were generated by PCR using oligonucleotides 828–31 and 1553–72 (See Table 1). These fragments were digested with AatII and BglII and then ligated into pTS2d to create pCB plasmid vectors (see FIG. 30). The motA/asiA operon described in Example 10 was then cloned into these pCB plasmid vectors from XbaI to XhoI to create pAW plasmid vectors (see FIG. 31).

Another single pCB plasmid was constructed using the mutated TET promoter for the control of the MS2 coat protein. A cassette of the MS2 coat protein gene linked to the TET promoter was PCR constructed using oligonucleotides 1870–97 and 1906–27(See Table 1). This fragment was digested XhoI to BglII and ligated into pTS2d to create pCB11. The motA/asiA operon described in Example 10 was then cloned into this vector from XbaI to XhoI to create pAW11 (Ps4 promoter).

EXAMPLE 13

This example describes the testing of the pAW plasmid vectors prepared and described in Example 12. Expression experiments were carried out in which product genes were cloned under either the T4 uvsX or X promoters. The expression and leakage characteristics of the following systems were compared: 1) T7 gene 1 cloned and coexpressed with pAW20 in *E. coli* GM221 containing pAMGX (i.e., T7 gene 1 under control of T4 X promoter; 2) SPI cloned and coexpressed with pAW20 in *E. coli* GM225 containing pAMGX (i.e., SPI under control of T4 X promoter; 3) OPG cloned and coexpressed with pAW20 in *E. coli* GM225 containing pAMGuvsX (i.e., OPG under control of T4 uvsX promoter); 4) BDNF cloned and coexpressed with pAW11 in *E. coli* GM225 containing pAMGuvsX (i.e., BDNF under control of T4 uvsX promoter; 5) OPG cloned and coexpressed with pAW11 in *E. coli* GM225 containing pAMGuvsX (i.e., OPG under control of T4 X promoter; 6) NT3 cloned and coexpressed with pAW11 in *E. coli* GM225 containing pAMGuvsX (i.e., NT3 under control of T4 uvsX promoter; and 7) 3MNDF cloned and coexpressed with pAW11 in *E. coli* GM225 containing pAMGX (i.e., 3MNDF under control of T4 X promoter.

For each experiment, single colonies were picked from plates and grown up in 5 ml 2XYT with Tetracycline and Kanamycin. The tubes shook overnight at 28° C. 50 ml tubes were set up with 5 ml 2XYT with Tet and Kan. The fresh tubes were inoculated with 50 µl of the starter cultures. These tubes were grown with shaking at 28° C. to an O.D. of 0.6–1.2. The PS4 promoter containing cultures and UV5 lac promoter containing cultures were induced with 20 µl IPTG, while the lambda promoter containing cultures were induced by shifting to either 37° C. or 42° C. Induction time for all of these expression experiments was 4.0 hours. 1 ml of each culture was centrifuged for 10 minutes. The supernatant was decanted and the pellet was frozen. 500 µl of each culture was diluted into 500 µl of LB and the optical density was taken. Pellets were then thawed and resuspended in 0.01 OD unit/µl cracking buffer. 6 µl of these cracked pellets were then loaded onto an SDS polyacrylamide gel (4–20% or 16%). After running at 150V for 1.3 hours the gels were stained with coomassie blue to visualize the proteins.

Figure 32:
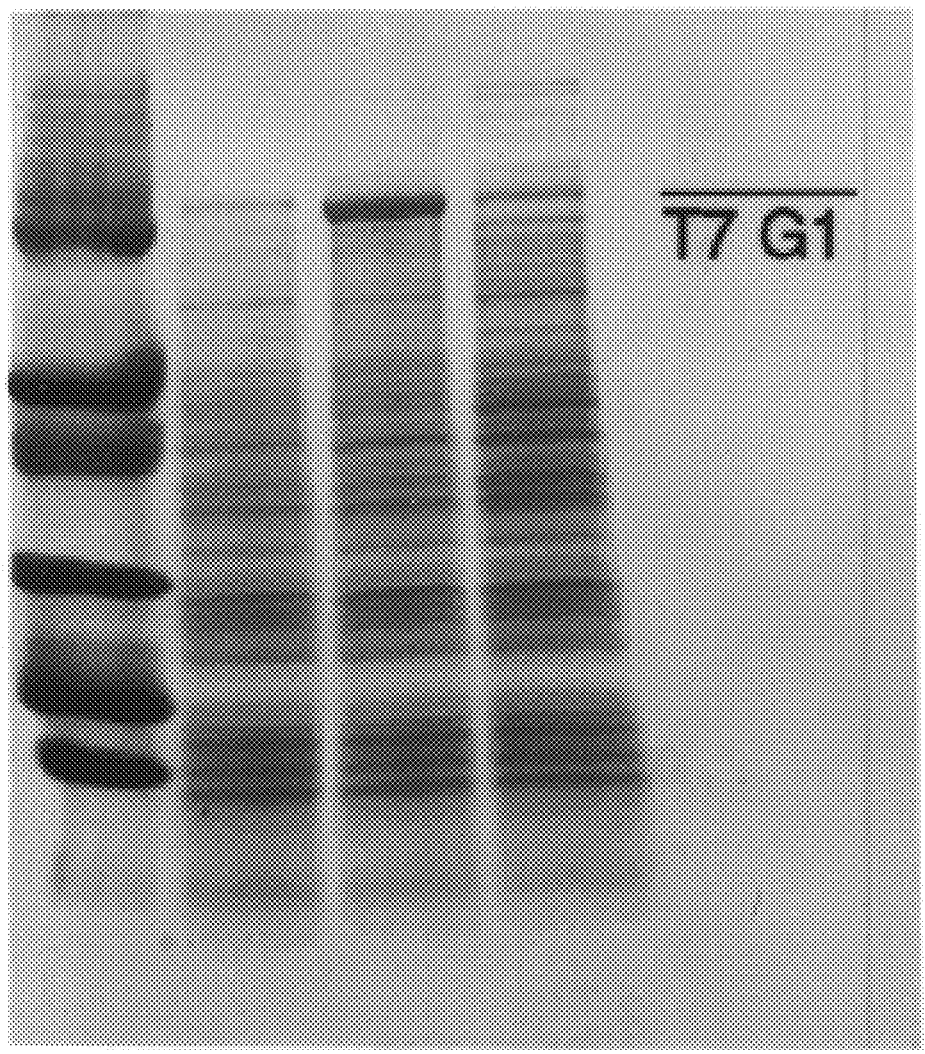
FIG. 32 is a picture of an SDS gel which shows the leakage and expression characteristics of pAMGX in which T7 gene 1 (under the control of the T4 X middle promoter) was coexpressed with pAW20. Lane 4 represents a stationary sample which grew overnight at overnight 28° C., lane 3 represents a sample which was induced for 4 hours at 28° C., lane 2 represents an uninduced sample which grew at 28° C. to an O.D. of 0.6, and lane 1 is the low range Biorad molecular weight marker.
Figure 33:
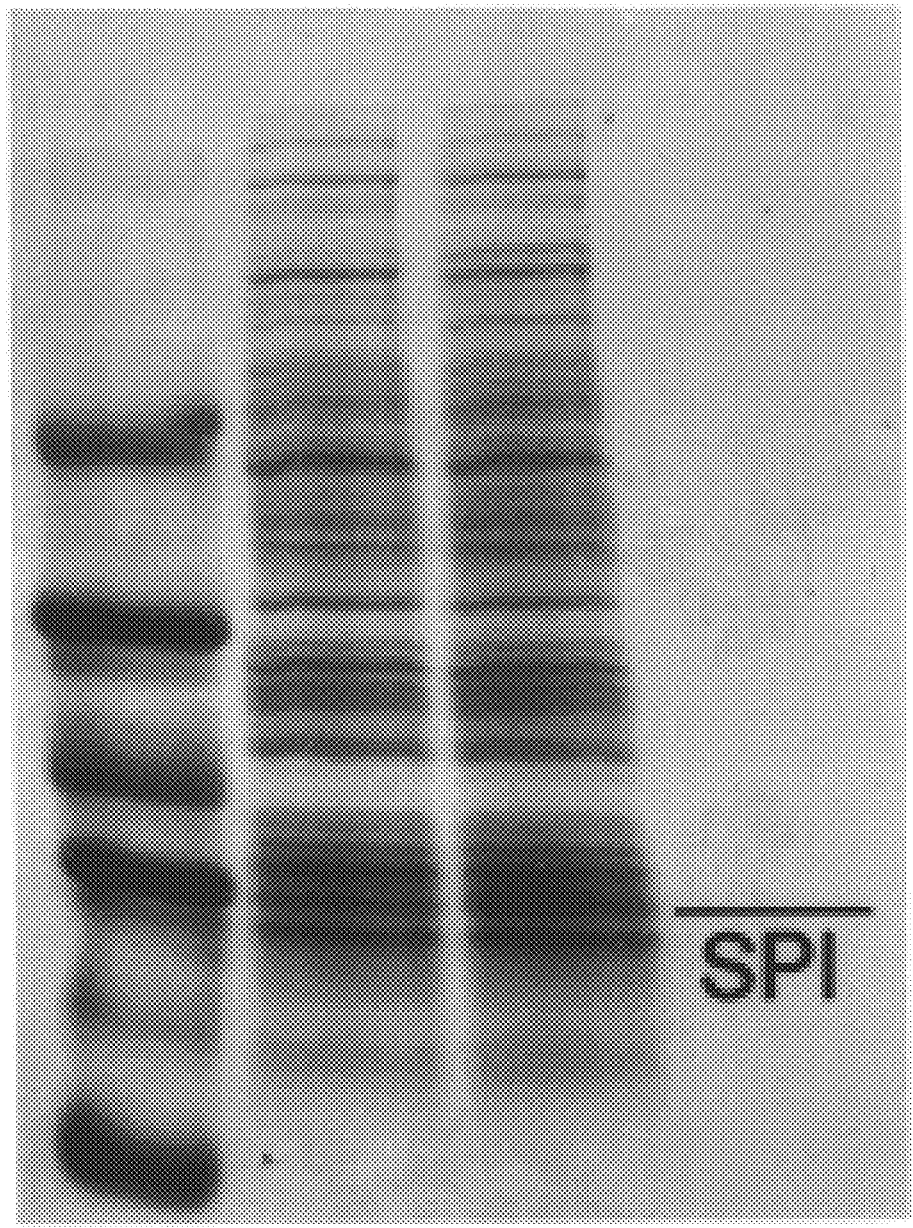
FIG. 33 is a picture of an SDS gel which shows the leakage and expression characteristics of pAMGX in which SPI (under the control of the T4 X middle promoter) was coexpressed with pAW20. Lane 3 represents a sample which was induced for 4 hours at 28° C., lane 2 represents an uninduced sample which grew at 28° C. to an O.D. of 0.6, and lane 1 is the low range Biorad molecular weight marker.
Figure 34:
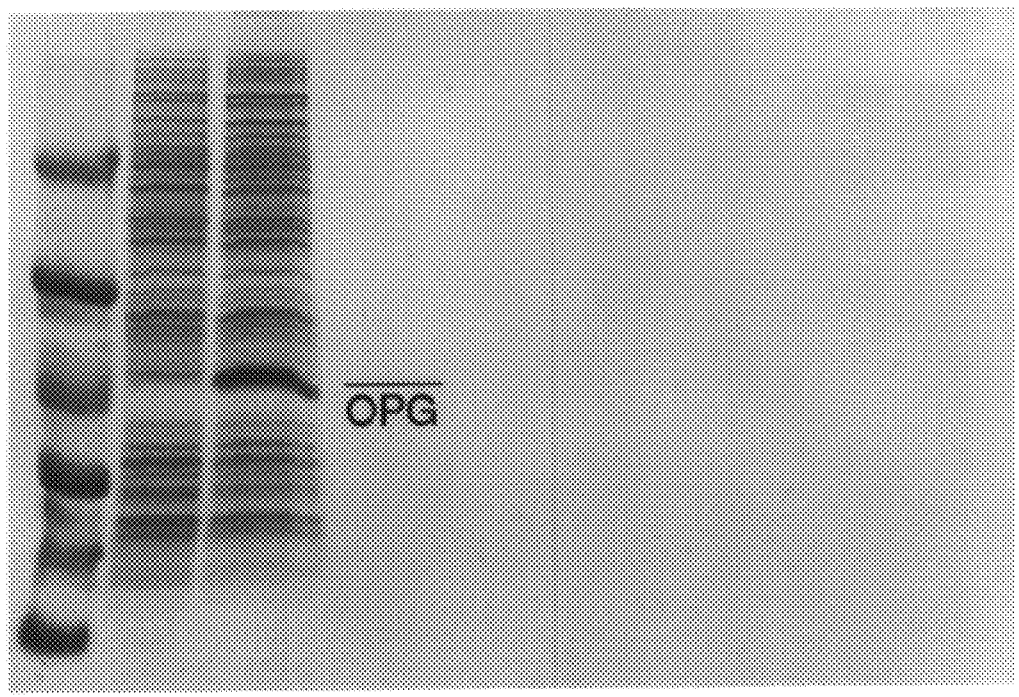
FIG. 34 is a picture of an SDS gel which shows the leakage and expression characteristics of pAMGuvsX in which OPG (under the control of the T4 uvsX middle promoter) was coexpressed with pAW20. Lane 4 represents a sample which was induced for 4 hours at 28° C., lane 2 represents an uninduced sample which grew at 28° C. to an O.D. of 0.6, and lane 1 is the low range Biorad molecular weight marker.
Figure 35:
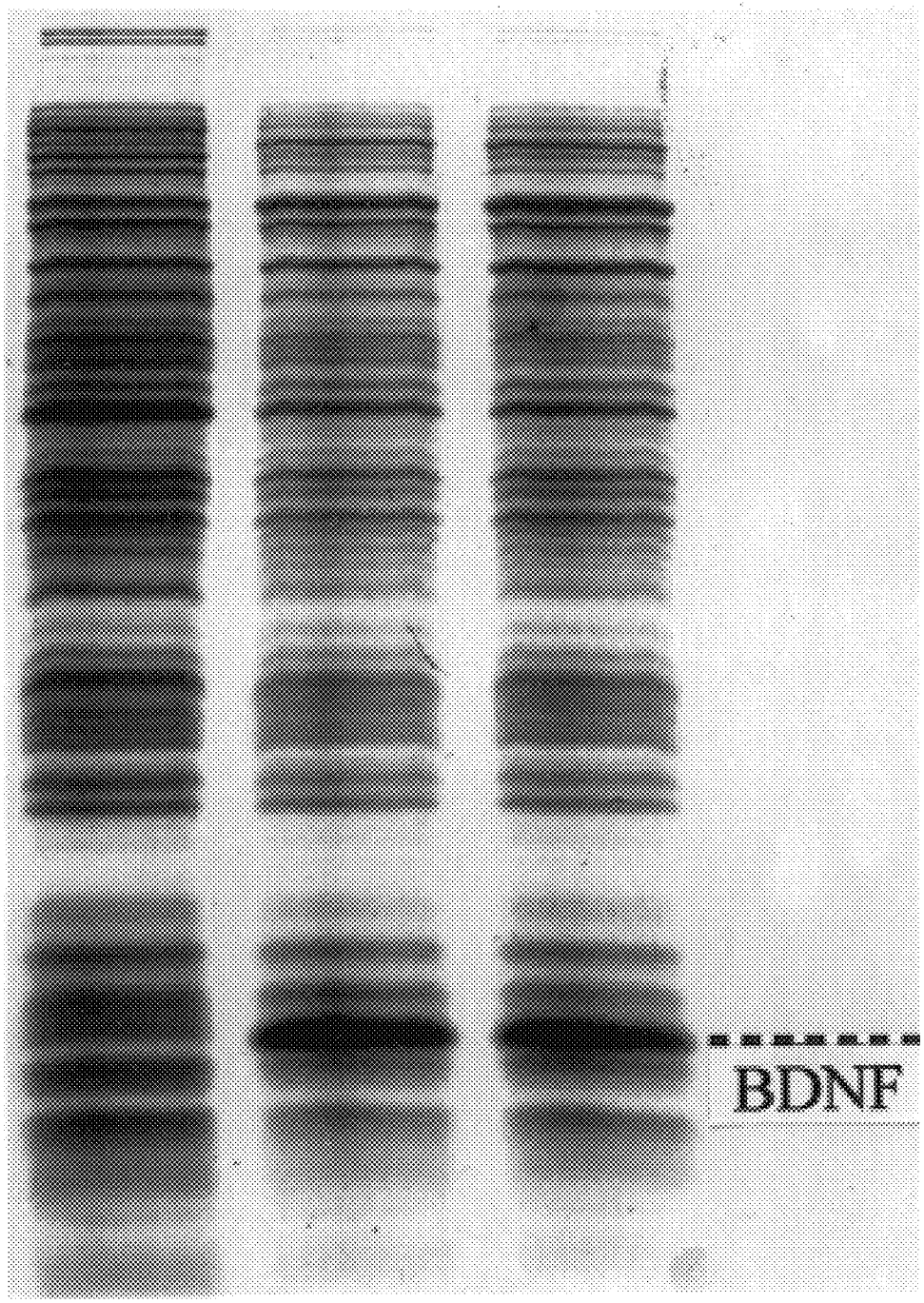
FIG. 35 is a picture of an SDS gel which shows leakage and expression characteristics of pAMGuvsX in which BDNF (under the control of the T4 uvsX middle promoter) was coexpressed with pAW11. Lane 1 represents an uninduced sample, lane 2 represents a sample induced at 28° C. for 4 hours and lane 3 represents a sample induced at 37° C. for 4 hours.
Figure 36:
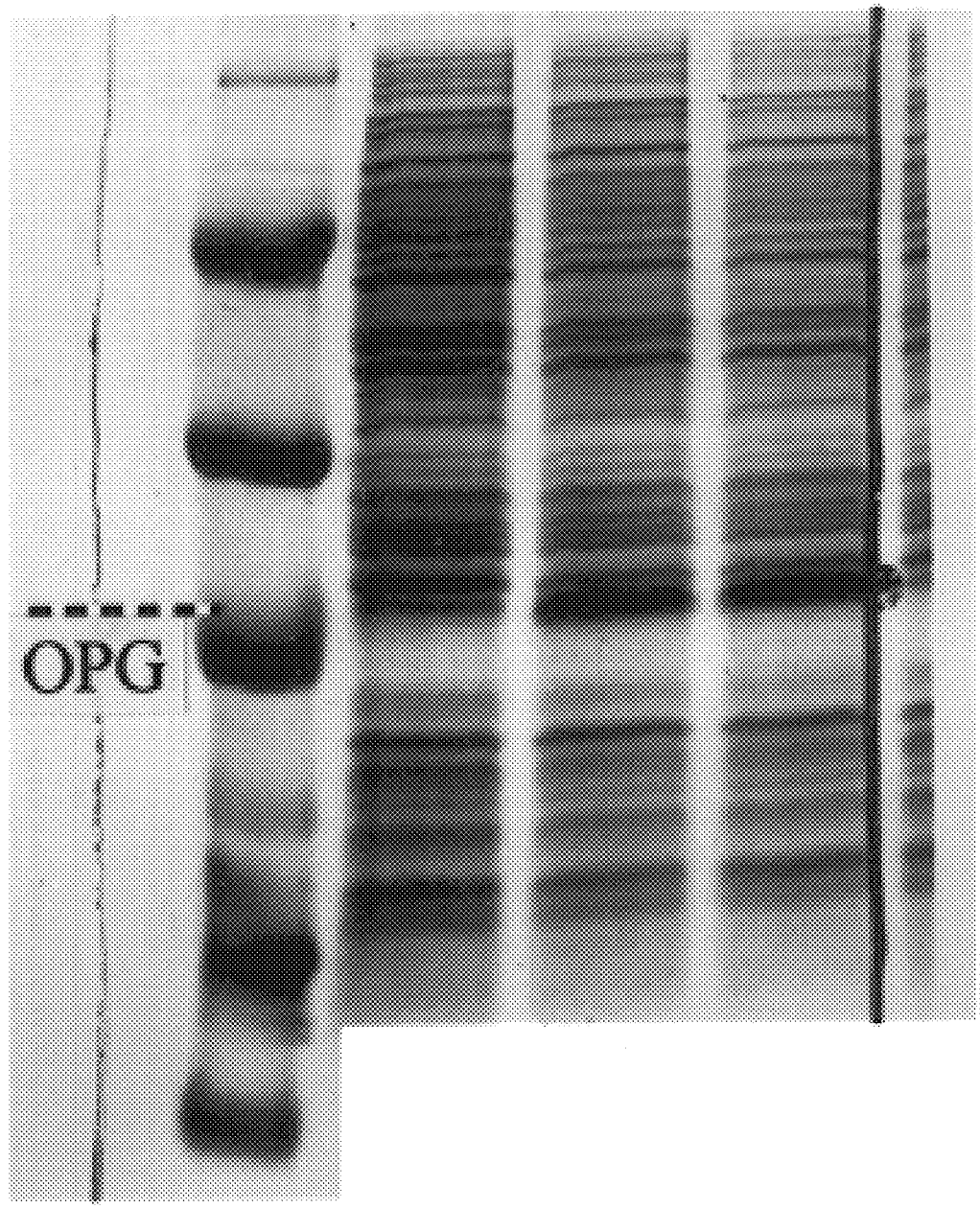
FIG. 36 is a picture of an SDS gel which shows leakage and expression characteristics of pAMGuvsX in which OPG (under the control of the T4 uvsX middle promoter) was coexpressed with pAW11. Lane 1 lane is Amersham low molecular weight rainbow markers, Lane 2 represents an uninduced sample, lane 3 represents a sample induced at 28° C. for 4 hours and lane 4 represents a sample induced at 37° C. for 4 hours.
Figure 37:
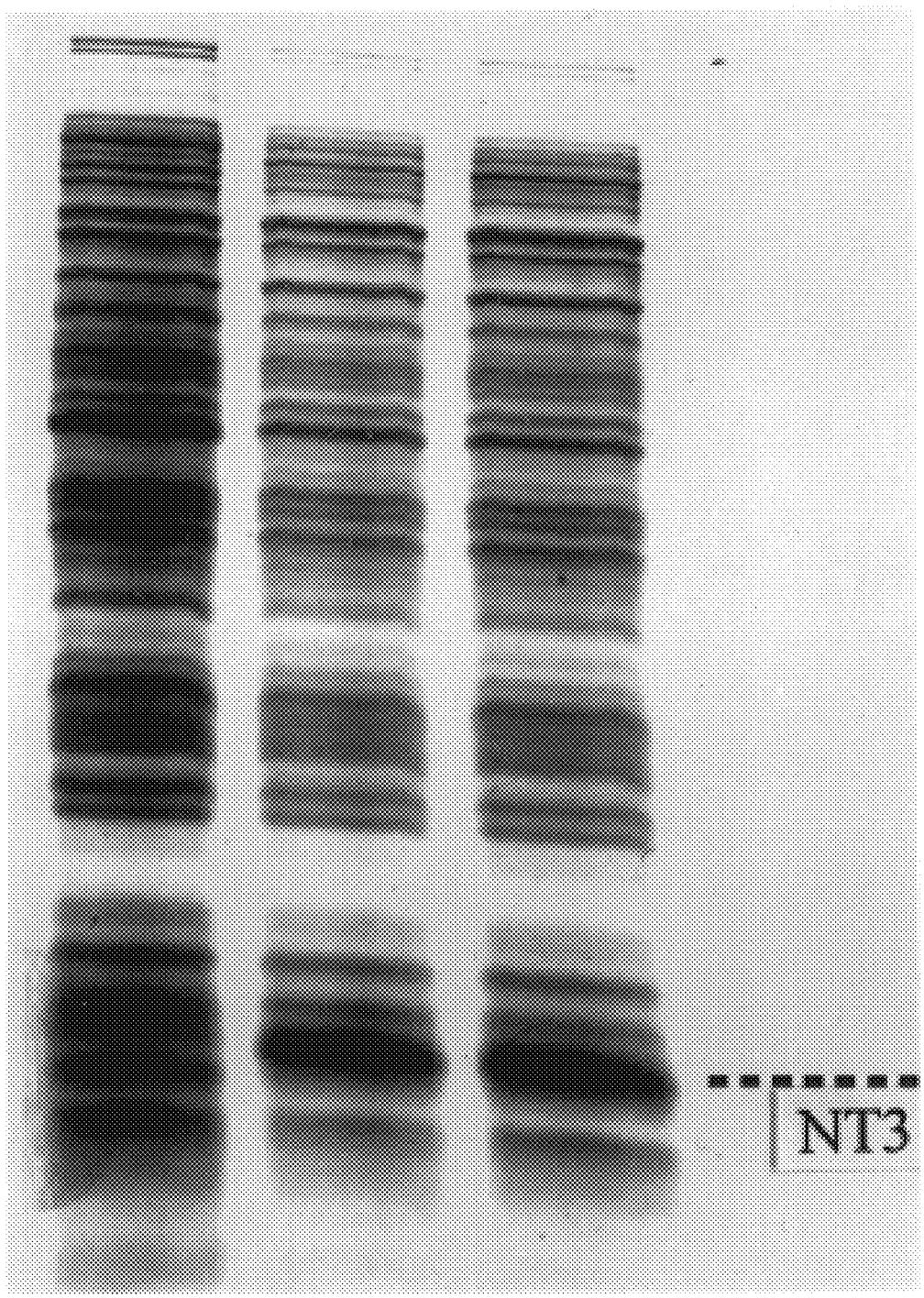
FIG. 37 is a picture of an SDS gel which shows leakage and expression characteristics of pAMGuvsX in which NT3 (under the control of the T4 uvsX middle promoter) was coexpressed with pAW11. Lane 1 represents an uninduced sample, lane 2 represents a sample induced at 28° C. for 4 hours and lane 3 represents a sample induced at 37° C. for 4 hours.

The data from FIGS. 32–34 can be summarized as follows: 1) abundant levels of T7 gene 1 can be obtained in pAMGX wherein T7 gene 1 is cloned and coexpressed with pAW20 (FIG. 32); 2) abundant levels of SPI can be obtained in pAMGX wherein SPI is cloned and coexpressed with pAW20 (FIG. 33); and 3) abundant levels of OPG can be obtained in pAMGuvsX wherein OPG is cloned and coexpressed with pAW20 (FIG. 34).

Figure 38:
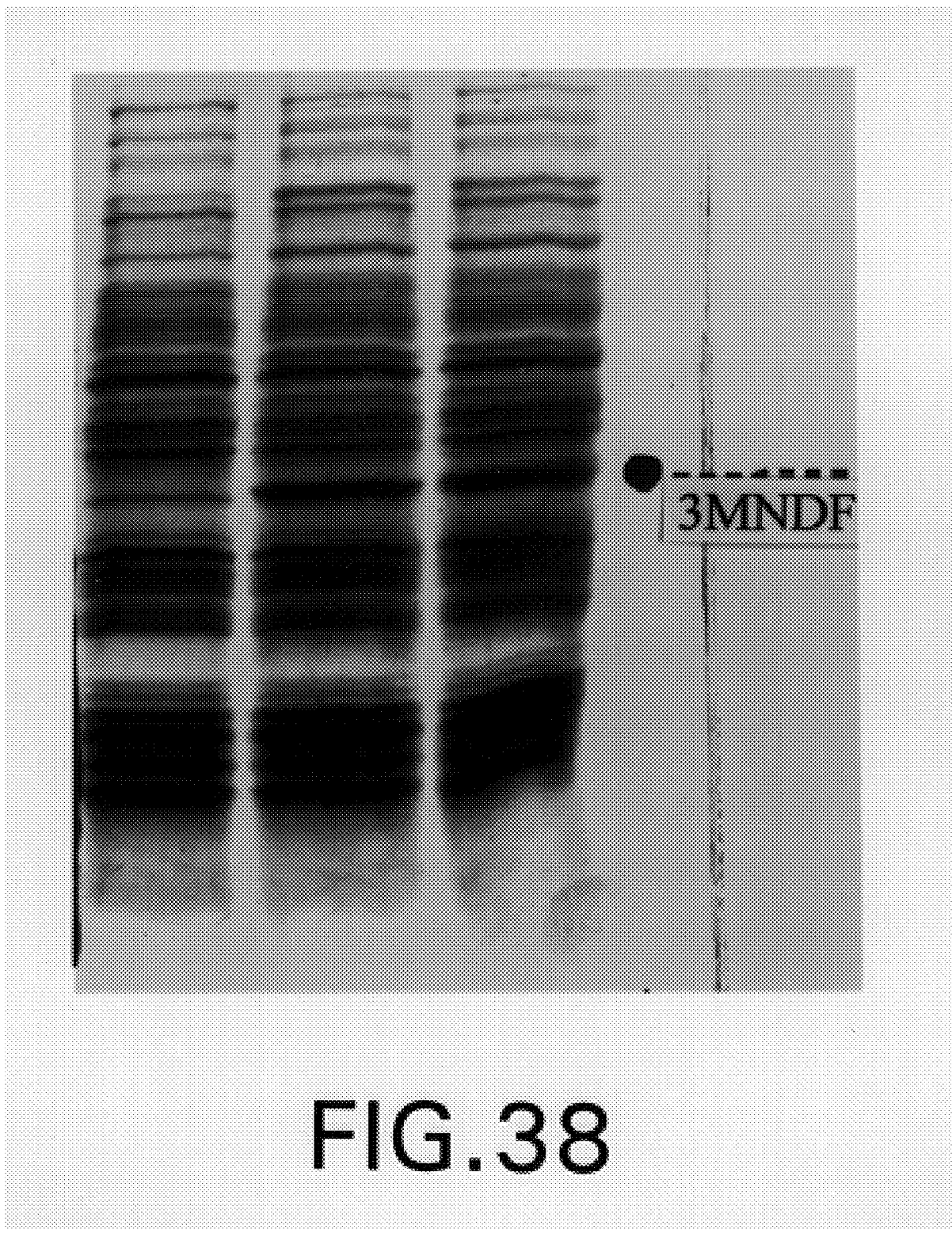
FIG. 38 is a picture of an SDS gel which shows leakage and expression characteristics of pAMGX in which 3MNDF (under the control of the T4 X middle promoter) was coexpressed with pAW11. Lane 1 represents an uninduced sample, lane 2 represents a sample induced at 28° C. for 4 hours and lane 3 represents a sample induced at 37° C. for 4 hours.

The data from FIGS. 35–38 can be summarized as follows: 1) abundant levels of BDNF can be obtained in pAMGuvsX wherein BDNF is cloned and coexpressed with pAW11 (FIG. 35); 2) abundant levels of OPG can be obtained in pAMGuvsX wherein OPG is cloned and coexpressed with pAW11 (FIG. 36); 3) abundant levels of NT3 can be obtained in pAMGuvsX wherein NT3 is cloned and coexpressed with pAW11 (FIG. 37); 4) abundant levels of 3MNDF can be obtained in pAMGX wherein 3MNDF is cloned and coexpressed with pAW11 (FIG. 38).

Because testing with the single copy pAW plasmids provides a system similar to that which would occur if the MS2-based T4 cassette were placed on the chromosome, it is contemplated by the present invention that each of the required MS2-T4 middle promoter elements could be placed on the chromosome of the host cell to provide an effective, tightly controlled system.

EXAMPLE 14

This example describes the use of the MS2-based T4 system to effectively express an accessory protein and thereby enhance expression of a target protein.

A T4 operon containing motA and asiA was PCR constructed to have a XhoI site at the start, followed by an MS2 recognition site, and a BamHI site at the end of the asiA gene which is also preceded by an MS2 recognition site (oligonucleotides 1351–01 and 1260–86)(See Table 1) This fragment was then cloned into the corresponding sites of pRIN10 (giving T4 operon PRIN10).

The 0.6 gene of T7 was constructed to have an XbaI site followed by an MS2 recognition site and ending with a XhoI site (oligonucleotides 1443–41 and 1465–31)(See Table 1). This 0.6 fragment was then put into the T4 operon pRIN10 using the corresponding sites. This yields a plasmid (0.6 T4 operon pRIN10) that can express both the 0.6 gene and the T4 transcription factors. Expression experiments were then carried out (following the same experimental protocol as described in Example 11) using a system wherein BDNF was cloned and coexpressed with 0.6 T4 operon pRIN10 in *E. coli* host GM225 containing pAMGuvsX (i.e., BDNF under the control of the T4 uvsX middle promoter).

Figure 29:
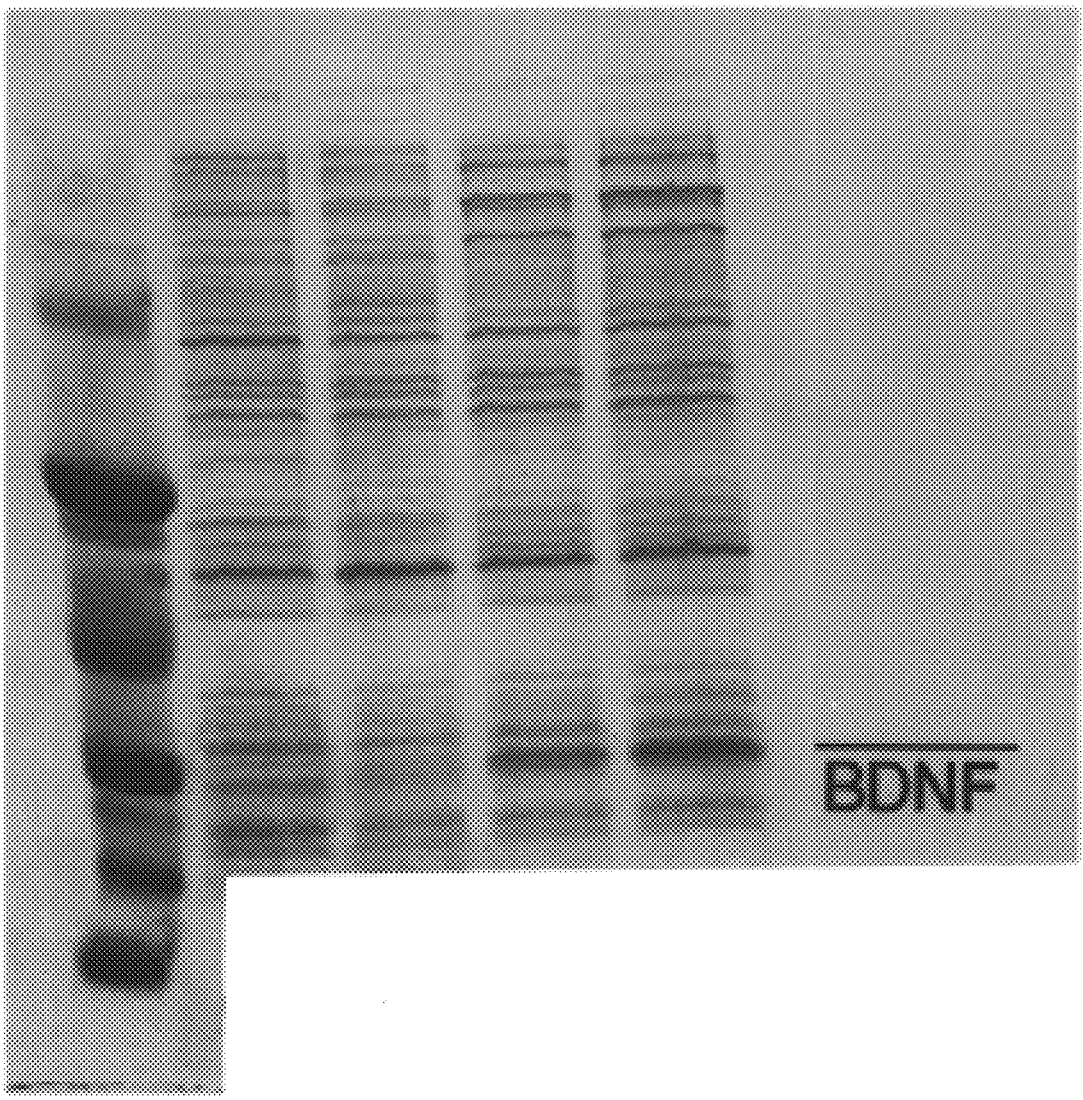
FIG. 29 is a picture of an SDS gel which shows the leakage and expression characteristics of pAMGuvsX in which BDNF (under the control of the uvsX T4 middle promoter) was coexpressed with T4 operon PRIN10. Lane 5 represents a sample which was induced for 4 hours at 42° C., lane 4 represents a sample which was induced for 4 hours at 37° C., lane 3 represents a sample which was induced for 4 hours at 28° C., lane 2 represents an uninduced sample which grew at 28° C. to an O.D. of 0.6, and lane 1 is the low range Biorad molecular weight marker.
Figure 39:
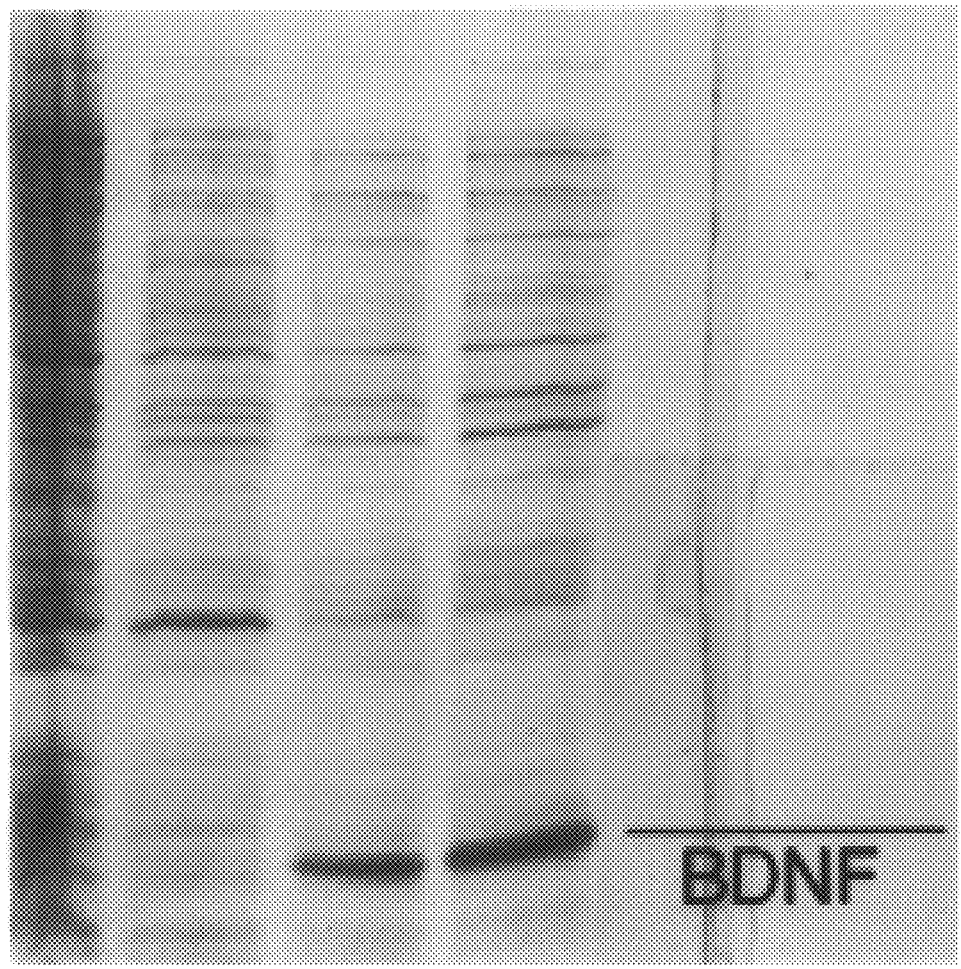
FIG. 39 is a picture of an SDS gel which shows the leakage and expression characteristics of pAMGuvsX in which BDNF (under the control of the T4 uvsX middle promoter) was coexpressed with a T4 operon pRIN10 which also contained 0.6 gene as an accessory protein. Lane 5 represents a sample which was induced for 4 hours at 42° C., lane 4 represents a sample which was induced for 4 hours at 37° C., lane 3 represents a sample which was induced for 4 hours at 28° C., lane 2 represents an uninduced sample which grew at 28° C. to an O.D. of 0.6, and lane 1 is the low range Biorad molecular weight marker.

As depicted in FIG. 39, abundant levels of BDNF could be obtained using this system, and the levels obtained were superior to those obtained using a T4 operon pRIN10 system lacking the 0.6 gene (compare lanes 4 and 5, FIG. 29 to lanes 4 and 5, FIG. 39). Therefore, the accessory protein (0.6) enhanced expression of target protein in a staged promoter expression system.

Provided in Table 1 below are the oligonucleotides utilized in the examples described herein.

TABLE 1

| | | |
|---|---|---|
| 909-34 | (SEQ ID NO:5) | TATGGCTTCTAACTTCACTCAGTTCGTACTGGTTGAC |
| 909-35 | (SEQ ID NO:6) | GCCTTGTCAACCAGTACGAACTGAGTGAAGTTAGAAGCCA |
| 909-36 | (SEQ ID NO:7) | AACGGCGGTACCGGCGATGTAACTGTTGCACCGTCCAACTTC |
| 909-37 | (SEQ ID NO:8) | ATTTGCGAAGTTGGACGGTGCAACAGTTACATCGCCGGTACC |
| 909-38 | (SEQ ID NO:9) | GCAAATGGCGTTGCTGAATGGATTTCTTCCAACTCT |
| 909-39 | (SEQ ID NO:10) | GCTGCGAGAGTTGGAAGAAATCCATTCAGCAACGCC |
| 909-40 | (SEQ ID NO:11) | CGCAGCCAGGCTTACAAAGTAACTTGCAGCGTTCGCCAGTCC |
| 909-41 | (SEQ ID NO:12) | TGCAGAGGACTGGCGAACGCTGCAAGTTACTTTGTAAGCCTG |
| 909-42 | (SEQ ID NO:13) | TCTGCACAAAACCGAAAATACACCATCAAGGTAGAA |
| 909-43 | (SEQ ID NO:14) | CGGGACTTCTACCTTGATGGTGTATTTTCGGTTTTG |
| 909-44 | (SEQ ID NO:15) | GTCCCGAAAGTTGCGACCCAGACTGTAGGCGGTGTCGAACTG |
| 909-45 | (SEQ ID NO:16) | AACCGGCAGTTCGACACCGCCTACCGTCTGGGTCGCAACTTT |
| 909-46 | (SEQ ID NO:17) | CCGGTTGCTGCATGGCGCAGCTACCTGAACATGGAA |
| 909-47 | (SEQ ID NO:18) | CGTCAGTTCCATGTTCAGGTAGCTGCGCCATGCAGC |
| 909-48 | (SEQ ID NO:19) | CTGACTATCCCGATTTTCGCAACCAACTCTGACTGTGAACTG |
| 909-49 | (SEQ ID NO:20) | TACGATCAGTTCACAGTCAGAGTTGGTTGCGAAAATCGGGAT |
| 909-50 | (SEQ ID NO:21) | ATCGTAAAAGCTATGCAGGGTCTGCTAAAAGAT |
| 909-51 | (SEQ ID NO:22) | ATTGCCATCTTTTAGCAGACCCTGCATAGCTTT |
| 909-52 | (SEQ ID NO:23) | GGCAATCCAATTCCGTCCGCAATCGCTGCAAACTCTGGTATCTACTAATAG |
| 909-53 | (SEQ ID NO:24) | GATCCTATTAGTAGATACCAGAGTTTGCAGCGATTGCGGACGGAATTGG |
| 1456-55 | (SEQ ID NO:25) | CGCAAATGGCATTGCTGAATGG |
| 1456-56 | (SEQ ID NO:26) | CCATTCAGCAATGCCATTTGCG |
| 1456-61 | (SEQ ID NO:27) | CCAACTCTGACCGTGAACTGATCG |
| 1456-62 | (SEQ ID NO:28) | CGATCAGTTCACGGTCAGAGTTGG |
| 940-29 | (SEQ ID NO:29) | AGCTGGTGAGCTCGATCATTGGGCATACGCATGCTGCAGCGC |
| 940-30 | (SEQ ID NO:30) | TCTAGGCGCTGCAGCATGCGTATGCCCAATGATCGAGCTCACC |
| 941-43 | (SEQ ID NO:31) | GGCCAATCGCGAATTGACGTCACGTTCAGAATT |
| 941-44 | (SEQ ID NO:32) | GGCCAATTCTGAACGTGACGTCAATTCGCGATT |

TABLE 1-continued

| | | |
|---|---|---|
| 1036-99 | (SEQ ID NO:33) | ATGCATCGAGCTCGATTAGGACATGGGGCCTCGCT |
| 1016-20 | (SEQ ID NO:34) | |
| | GCCCGCGCGAGCTCGTTGTAATTCTCATGTTTGACAGCTT ATCATCGATAAGCTTTAATGCGGTAGTT | |
| 1016-21 | (SEQ ID NO:35) | |
| | GGGAATTCCATATGCGGTGCCTGACTGCGTTAGCAATTTA ACTGTGATAAACTACCGCATTAAAGC | |
| 1036-6 | (SEQ ID NO:36) | |
| | GATTCCCCCGGGCAAATAAAACGAAAGGCTCAGTCGAAAG AC | |
| 1053-71 | (SEQ ID NO:37) | |
| | CTGATCGCGACGTCTTGTAGAAACGCAAAAAGGCCATCCG TCAG | |
| 949-1 | (SEQ ID NO:38) | |
| | GCTCTAGAAACATGAGGATTACCCATGAACACGATTAACA TCGCTAAGAACGACTTCTCTGAC | |
| 949-2 | (SEQ ID NO:39) | CGGGATCCGTCATTACGCGAACGCGAAGTCCGACTC |
| 1477-84 | (SEQ ID NO:40) | |
| | GCGCGCTCTAGAAAACATGAGGATTACCCATGAATACCAT CAATATCGCTAAGAACGACTTCTCTGACATC | |
| 1553-73 | (SEQ ID NO:41) | GGCCCAGTGCATGCCTACGTGGGTCCTAGTCGC |
| 1553-74 | (SEQ ID NO:42) | GATCGCGACTAGGACCCACGTAGGCATGCACTG |
| 305-3 | (SEQ ID NO:43) | CTGAATACGCTGAGGCTA |
| 305-14 | (SEQ ID NO:44) | TCAGCCAGTAGTAACCTT |
| 1049-5 | (SEQ ID NO:45) | |
| | GCGCGCGAATTCTTTCGATCTACTACCAACGTGCAATACG GTCTGACC | |
| 1049-7 | (SEQ ID NO:46) | |
| | GCGCGCGAATTCTTTCGAATGAAGCACTACGTTATGCCAA TCCACACG | |
| 1035-7 | (SEQ ID NO:47) | |
| | CTAGAGCAAACATGAGGATTACCCATGAAACATCACCATC ACCATCACCATACCGGTGGCG | |
| 1035-31 | (SEQ ID NO:48) | |
| | AATTCGCCACCGGTATGGTGATGGTGATGGTGATGTTTCA TGGGTAATCCTCATGTTTGCT | |
| 1482-18 | (SEQ ID NO:49) | |
| | GCGCGCTCTAGAAAACATGAGGATTACCCATGTCTACTAC CAACGTGCAATACGGTCTGACC | |
| 1266-69 | (SEQ ID NO:50) | GCGCGCGGATCCCGAGTCTATCACTCAGCAGATTCTA |
| 1266-71 | (SEQ ID NO:51) | |
| | GCGCGCGGATCCCTATTATGAGATAGCGTTCAGTGTGTTG GC | |
| 1053-66 | (SEQ ID NO:52) | |
| | GCGCGCCTCAGAAAACATGAGGATTACCCATGAACATTAC CGACATCATGAACGCTATCGACGCAATCA | |
| 1266-73 | (SEQ ID NO:53) | GCGCGCGGATCCCTATCAGCCCATTAACATTGCGTC |
| 1266-72 | (SEQ ID NO:54) | GCGCGCGGATCCCTATCATGCGACTTCCTCGACTTC |
| 1511-32 | (SEQ ID NO:55) | |
| | GCGCGCTCTAGAAAACATGAGGATTACCCATGGCTATGTC TAATCTCACATATAACAACGTTTTCGAC | |
| 1539-60 | (SEQ ID NO:56) | |
| | CACGTTGGTAGTAGACATGGGTAATCCTCATGTTTTTACT CTTCATCCTCCTCGTACTCC | |
| 1539-65 | (SEQ ID NO:57) | GTCGGTAATGTTCATGGGTAATCCTCATGTTTTTATGAGA TAGCGTTCAGTGTGTTGG |
| 1803-86 | (SEQ ID NO:58) | AGCATATACATGGGTAATCCTCATGTTTGAGTCTATCACT CAGCAGATTCTAAAGC |
| 1319-59 | (SEQ ID NO:59) | |
| | CTGCTGAGTGATAGACTCAAACATGAGGATTACCCATGTA TATGC | |
| 1577-83 | (SEQ ID NO:60) | CATAACGTAATGCCGCATGGGTAATCCTCATGTTTTCATC ATTTGCGTAGTGCCCCTTTGATG |
| 1577-84 | (SEQ ID NO:61) | |
| | CATCAAAGGGGCACTACGCAAATGATGAAAACATGAGGAT TCCCATGCGGCATTACGTTATG | |
| 1066-72 | (SEQ ID NO:62) | |
| | GAACGCTATCTCATAACGAAACATGAGGATTACCCATGAA CATTACCG | |
| 1435-93 | (SEQ ID NO:63) | GCGCGGATCCCTATCATGCGACTTC |
| 1084-66 | (SEQ ID NO:64) | |
| | GCGCGCGACGTCGGCAAAAAGCAGTCAGAAGAAACTAAAG CAGCAAAACGAAAAGAAGCTTTGCTT | |
| 1084-67 | (SEQ ID NO:65) | GCGCGCATCGATTGATGGTTTATTTCTATTATAACCATAT CGATTATTAAGCAAAGCTTCTT |
| 1084-68 | (SEQ ID NO:66) | |
| | GCGCGCGACGTCTGATAGAGTCAATGAGTTAAAACACAGT GATGTTTTGCGTAAAGAGAT | |
| 1084-69 | (SEQ ID NO:67) | |
| | GCGCGCATCGATGCACGGGTTTTATTTAAAATATCATGTT GAATAGAAAGCATCTCTTTACGC | |

TABLE 1-continued

| | |
|---|---|
| 1202-11 | (SEQ ID NO:68)<br>GCGCGCGACGTCGGCAAAAAGCAGTCAGAAGAAACTAAAG<br>CAAAACGAAAAGAAGCTTTGCTT |
| 1550-85 | (SEQ ID NO:69) GCGCGCATCGATTGATGGTTTATTTCTATTATAACGATAT<br>AGATTATTAAGCAAAGCTTCTTT |
| 1084-63 | (SEQ ID NO:70)<br>GCGCGCTCTAGAAAACATGAGGATTACCCATGTCTAAAGT<br>AACTTACATCATCAAAGCTTCTA |
| 1528-19 | (SEQ ID NO:71) TGTATCAATGTTTTTATTCATGGGTGATCCTC |
| 1528-20 | (SEQ ID NO:72) ATGAATAAAAACATTGATACAGTTCGTG |
| 1703-53 | (SEQ ID NO:73)<br>GCGCGCCTCGAGCTATTATTTGTTCGTATACATCTCCAGG<br>TATCGATA |
| 828-31 | (SEQ ID NO:74) GGATGGCCTTTTTGCGTTTCT |
| 1553-72 | (SEQ ID NO:75)<br>GCGCGCAGATCTGAAGATCTTATTAATCAGATAAAATATT<br>TCTAGGCG |
| 1351-01 | (SEQ ID NO:76)<br>GCGCGCCTCGAGAAACATGAGGATTACCCATGTCTAAAGT<br>AACTTACATCATCAAAGCTTCTA |
| 1260-86 | (SEQ ID NO:77) GCGCGCGGATCCCTATTATTTGTTCGTATACATCTCCAGG<br>TATCGATA |
| 1443-41 | (SEQ ID NO:78)<br>GCGCGCTCTAGAAAACATGAGGATTACCCATGATGAAGCA<br>CTACGTTATGCCAATCCACACGTCC |
| 1465-31 | (SEQ ID NO:79) GCGCGCCTCGAGCTATTATGAGATAGCGTTCAG |
| 1870-97 | (SEQ ID NO:80)<br>GCGCGCGCATGCAGATCTGTATGCCCAATGATCGAGCTGTT<br>GTAATTCTC |
| 1906-27 | (SEQ ID NO:81)<br>GCGCGCCTCGAGCCGCGGCTATTAGTAGATACCAGAGTT<br>TGC |
| 1674-96 | (SEQ ID NO:82)<br>CAACACCCAGCGGCCGCTGCGTATCAATGATCGAGCTGT |
| 1674-97 | (SEQ ID NO:83) AAGCTTACTCGAGGATCCCTATTAGTAGATACCAGAGT |
| 1011-96 | (SEQ ID NO:84) GCTGCCGCTGTTAGTCTTCGTTCC |
| 1784-89 | (SEQ ID NO:85) CTACCGCATTATAGCTTATCGATGATAAGCT |
| 1758-66 | (SEQ ID NO:86) CGATAAGCTATAATGCGGTAGTTTACAGTTAAA |
| 1784-88 | (SEQ ID NO:87) TTATTCCTCCTTGCGTTAGCAATTTAACTGTGATAAACTA<br>CCGCATTATAGCTTATCG |
| 1803-15 | (SEQ ID NO:88)<br>CGATAAGCTATAATGCGGTAGTTTATCACAGTTAAATTGC<br>TAACGCAAGGAATAACATATGGCTTCTAACTTCACTCAG |
| 1803-52 | (SEQ ID NO:89)<br>CCACCACCGGGTACCGTCGTTTTACAACGTCGTGACTGG |
| 1803-53 | (SEQ ID NO:90) CCACCACACGGATCCTTATTTTTGACACCAGACCAACT |
| 1822-01 | (SEQ ID NO:91) AGTTAAATTGCTAACGCA(AG)(AG)(AG)(AG)GGCACC<br>GCATATGCTTCTAACTTCACTCA |
| 1822-02 | (SEQ ID NO:92)<br>GTTCGTACTGGTTGACAACGGCGGTACCCACAGTGACTATA<br>TGGGTGGCA |
| 1822-03 | (SEQ ID NO:93) ATCGATGATAAGCTGTCAATAATGAGAATT |
| 1822-04 | (SEQ ID NO:94) GTTAGCAATTTAACTGTGATAAACTACCGC |
| 1822-05 | (SEQ ID NO:95) TCAACCAGTACGAACTGAGTGAAGTTAGAA |
| 1863-81 | (SEQ ID NO:96) CAGCTTATCATCGATAAGCTATAATGCGGTAGTTAATCAC |
| 1822-06 | (SEQ ID NO:97) TGACACACGGTCAATGGTTGG |
| 1822-07 | (SEQ ID NO:98) TGCCACCCATATAGTCACTGTGG |

Deposits of DNA/Host Cells

E. coli K-12/GM350 host cells were deposited with the ATCC (American Type Culture Collection, 12301 Parklawn Drive Rockville, Md., USA) on Jan. 20, 1999.

E. coli K-12/GM225 host cells have been deposited with the ATCC (American Type Culture Collection, 10801 University Blvd. Manassas, Va., USA) on Jan. 27, 1998, and assigned accession No. 20281.

E. coli K-12/GM225 host cells containing plasmid vector pAMG13 have been deposited with the ATCC (American Type Culture Collection, 10801 University Blvd., Manassas, Va., USA) on Jan. 27, 1998, and assigned accession No. 98641.

E. coli K-12/GM225 host cells containing plasmid vector pAMG25 have been deposited with the ATCC (American Type Culture Collection, 10801 University Blvd., Manassas, Va., USA) on Jan. 27, 1998, and assigned accession No. 98642.

E. coli K-12/GM225 host cells containing plasmid vector 3002 nahG have been deposited with the ATCC (American Type Culture Collection, 10801 University Blvd., Manassas, Va., USA) on Jan. 27, 1998, and assigned accession No. 98645.

E. coli K-12/GM225 host cells containing plasmid vector pRIN10(wt) have been deposited with the ATCC (American Type Culture Collection, 10801 University Blvd., Manassas, Va., USA) on Jan. 27, 1998, and assigned accession No. 98639.

E. coli EE11-11M host cells have been deposited with the ATCC (American Type Culture Collection, 10801 University Blvd., Manassas, Va., USA) on Jan. 27, 1998, and assigned accession No. 202083.

E. coli EE11-20 host cells have been deposited with the ATCC (American Type Culture Collection, 10801 University Blvd., Manassas, Va., USA) on Jan. 27, 1998, and assigned accession No. 202082.

E. coli K-12/GM225 host cells containing plasmid vector pAMGuvsX have been deposited with the ATCC (American Type Culture Collection, 10801 University Blvd., Manassas, Va., USA) on Jan. 27, 1998, and assigned accession No. 98644.

E. coli K-12/GM225 host cells containing plasmid vector pAMGX have been deposited with the ATCC (American Type Culture Collection, 10801 University Blvd., Manassas, Va., USA) on Jan. 27, 1998, and assigned accession No. 98643.

E. coli K-12/GM225 containing plasmid vector T4 operon pRIN10 have been deposited with the ATCC (American Type Culture Collection, 10801 University Blvd., Manassas, Va., USA) on Jan. 27, 1998, and assigned accession No. 98640.

E. coli K-12/GM225 host cells containing plasmid vector pAW20 have been deposited with the ATCC (American Type Culture Collection, 10801 University Blvd., Manassas, Va., USA) on Jan. 28, 1998, and assigned accession No. 98638.

E. coli K-12/FM-15 host cells containing plasmid vector pAMG21 were deposited with the ATCC (American Type Culture Collection, 10801 University Blvd., Manassas, Va., USA) and assigned accession No. 98113.

E. coli K-12/GM221 host cells containing plasmid vector pAMG33 were deposited with the ATCC (American Type Culture Collection, 10801 University Blvd., Manassas, Va., USA) on Jan. 20, 1999.

Plasmid vector pAMG22 has been deposited with the ATCC (American Type Culture Collection, 10801 University Blvd., Manassas, Va., USA) on Jan. 28, 1998, and assigned accession No. 98646.

The present invention has been described in terms of particular embodiments found or proposed to comprise preferred modes for the practice of the invention. It will be appreciated by those of ordinary skill in the art that, in light of the present disclosure, numerous modifications and changes can be made in the particular embodiments exemplified without departing from the intended scope of the invention.

What is claimed is:

1. A translational repression vector system for use in cloning or expressing a specific heterologous gene in bacteria, said system comprising a DNA sequence encoding a translational repressor operably linked to a constitutive promoter, and said heterologous gene operably linked to an inducible promoter and a translational repressor recognition sequence; wherein pre-induction leakage of said inducible promoter is abolished without the loss of inducibility.

2. The system of claim 1, wherein said translational repressor is bacteriophage MS2 coat protein (MS2CP).

3. An process for cloning or expressing a heterologous gene in bacteria, said process comprising:
   culturing host cells transformed with a plasmid vector, said vector comprising a DNA sequence encoding an inducible promoter, a DNA sequence encoding said heterologous gene linked to a translational repressor recognition site and to said inducible promoter, and a DNA sequence encoding a translational repressor operably linked to a constitutive promoter; wherein said translational repressor controls expression of said heterologous gene.

4. An process for cloning or expressing a heterologous gene in bacteria, said process comprising:
   culturing host cells which have been co-transformed with a first plasmid vector comprising a DNA sequence encoding an inducible promoter and said heterologous gene linked to a translational repressor recognition site and to said inducible promoter, and a second plasmid vector comprising a DNA sequence encoding a translational repressor operably linked to a constitutive promoter; wherein said translational repressor controls expression of said heterologous gene.

5. An process for cloning or expressing a heterologous gene in bacteria, said process comprising:
   culturing host cells harboring a DNA sequence encoding a translational repressor operably linked to a constitutive promoter, transformed with a plasmid vector, said vector comprising a DNA sequence encoding an inducible promoter, and a DNA sequence encoding said heterologous gene linked to a translational repressor recognition site and to said inducible promoter; wherein said translational repressor controls expression of said heterologous gene.

6. An process for cloning or expressing a heterologous gene in bacteria, said process comprising:
   culturing host cells harboring a DNA sequence encoding an inducible promoter, a DNA sequence encoding said heterologous gene linked to a translational repressor recognition site and to said inducible promoter, and a DNA sequence encoding a translational repressor operably linked to a constitutive promoter; wherein said translational repressor controls expression of said heterologous gene.

7. A process as in one of claims 3–6, wherein said translational repressor is bacteriophage MS2 coat protein.

8. A process as in one of claims 3–5, wherein said vector further comprises SEQ ID NO:2.

9. An MS2 controlled T7 gene 1 cassette, said cassette comprising a DNA sequence encoding an inducible promoter and the MS2 recognition site each linked to T7 gene 1, and the MS2 coat protein gene under the control of a weak constitutive promoter.

10. A bacterial host cell capable of expressing a heterologous gene and harboring an MS2 controlled T7 gene 1 cassette.

11. An process for expressing a heterologous gene in bacteria, said process comprising:
   culturing host cells harboring an MS2 controlled T7 gene 1 cassette and transformed with a plasmid vector containing a DNA sequence encoding said heterologous gene under the control of a T7 promoter.

12. A process of claim 11, wherein said heterologous gene is a T7 early gene.

13. A staged inducible promoter system for cloning or expressing a heterologous gene in bacteria, said system comprising DNA encoding motA and asiA gene sequences that direct transcription from specific promoters, while inhibiting general transcription from bacterial host promoters.

14. An process for cloning or expressing a heterologous gene in bacteria, said process comprising:
   culturing host cells which have been co-transformed with a first plasmid vector comprising a DNA sequence encoding said heterologous gene under the control of a T4 middle promoter, and a second plasmid vector comprising a DNA sequence encoding an inducible promoter, motA and asiA gene sequences each linked to a translational repressor recognition site and to said inducible promoter, and a translational repressor operably linked to a constitutive promoter; wherein said translational repressor controls expression of said motA and asiA genes, and wherein said motA and asiA genes direct transcription from the T4 middle promoter while inhibiting transcription from said inducible promoter.

15. A process of claim 14, wherein said second plasmid vector further comprises a DNA sequence encoding an accessory protein.

16. An process for cloning or expressing a heterologous gene, said process comprising:

culturing host cells harboring a DNA sequence encoding an inducible promoter, motA and asiA gene sequences each linked to a translational repressor recognition site and to said inducible promoter, and a translational repressor operably linked to a constitutive promoter, transformed with a plasmid vector comprising a DNA sequence encoding said heterologous gene linked under the control of a T4 middle promoter; wherein said translational repressor controls expression of said motA and asiA genes, and wherein said motA and asiA genes direct transcription from the T4 middle promoter while inhibiting transcription from said inducible promoter.

17. A process as in one of claims 14–16, wherein said translational repressor is bacteriophage MS2 coat protein.

18. An MS2-based T4 cassette, said cassette comprising a DNA sequence encoding an inducible promoter, motA and asiA gene sequences each linked to an MS2 recognition sequence and to said inducible promoter, and the MS2 coat protein gene under the control of a constitutive promoter.

19. A prokaryotic host cell capable of expressing a heterologous gene and harboring an MS2-based T4 cassette.

20. An improved process for cloning or expressing a heterologous gene, said process comprising:

culturing host cells harboring an MS2-based T4 cassette and transformed with an expression vector containing a DNA sequence encoding said heterologous gene under the control of a T4 promoter.

21. A DNA comprising the sequence of SEQ ID NO: 1.

22. A DNA comprising the sequence of SEQ ID NO:2.

\* \* \* \* \*

UNITED STATES PATENT AND TRADEMARK OFFICE
CERTIFICATE OF CORRECTION

PATENT NO. : 6,180,391 B1
DATED : January 30, 2001
INVENTOR(S) : William C. Brown It is certified that error appears in the above-identified patent and that said Letters Patent is hereby corrected as shown below:

Column 24,
Line 64, F'tet/393AlacZ145N should be corrected to read: -- F'tet/393ÆlacZ145N --

Column 31, Table 1, Seq. ID No. 47,
Example 1035-7 should read: -- Example 1035-30 --.

Column 31, Table 1, Seq. ID NO. 65,
Should read: -- GCGCGCATCGATTGATGGTTTATTTCTA
TTATAACCATATGGATTATTAAGCAAAGCTTCTTT --

Column 63, claim 1,
Should read:

1. A translational repression vector system for use in cloning or expressing a DNA sequence encoding a specific heterologous gene in bacteria, said system comprising a translational repressor operably linked to a constitutive promoter, and said heterologous gene operably linked to an inducible promoter and a translational repressor recognition sequence; wherein pre-induction leakage of said inducible promoter is abolished without the loss of inducibility.

Signed and Sealed this

Sixth Day of November, 2001

*Attest:*

NICHOLAS P. GODICI
*Attesting Officer*     *Acting Director of the United States Patent and Trademark Office*